US009133431B2

(12) United States Patent
Peterson et al.

(10) Patent No.: US 9,133,431 B2

(45) Date of Patent: Sep. 15, 2015

(54) SYSTEMS, METHODS AND COMPOSITIONS FOR OPTIMIZING TISSUE AND CELL ENRICHED GRAFTS

(75) Inventors: Alvin Peterson, Jamul, CA (US); Lucas Fornace, La Jolla, CA (US)

(73) Assignee: BIMINI TECHNOLOGIES LLC, San Diego, CA (US)

(*) Notice: Subject to any disclaimer, the term of this patent is extended or adjusted under 35 U.S.C. 154(b) by 0 days.

(21) Appl. No.: 12/771,985

(22) Filed: Apr. 30, 2010

(65) Prior Publication Data

US 2010/0279405 A1 Nov. 4, 2010

Related U.S. Application Data

(60) Provisional application No. 61/174,860, filed on May 1, 2009.

(51) Int. Cl.

| | |
|---|---|
| ***C12M 1/12*** | (2006.01) |
| ***C12N 5/071*** | (2010.01) |
| ***C12M 1/00*** | (2006.01) |
| ***A61K 35/35*** | (2015.01) |

(52) U.S. Cl.

CPC ................ *C12M 47/04* (2013.01); *A61K 35/35* (2013.01)

(58) Field of Classification Search

None

See application file for complete search history.

(56) References Cited

U.S. PATENT DOCUMENTS

| | | | | |
|---|---|---|---|---|
| 4,000,275 | A | | 12/1976 | Lunn |
| 4,418,691 | A | | 12/1983 | Yannas et al. |
| 4,458,678 | A | | 7/1984 | Yannas et al. |
| 4,734,269 | A | * | 3/1988 | Clarke et al. .................... 96/156 |
| 4,820,626 | A | | 4/1989 | Williams et al. |
| 4,834,703 | A | | 5/1989 | Dubrul et al. |
| 4,883,755 | A | | 11/1989 | Carabasi et al. |
| 4,897,185 | A | | 1/1990 | Schuyler et al. |
| 4,963,489 | A | | 10/1990 | Naughton et al. |
| 5,034,135 | A | | 7/1991 | Fischel |
| 5,035,708 | A | | 7/1991 | Alchas et al. |
| 5,079,160 | A | | 1/1992 | Lacy et al. |
| 5,087,244 | A | | 2/1992 | Wolinsky et al. |
| 5,092,883 | A | | 3/1992 | Eppley et al. |
| 5,131,907 | A | | 7/1992 | Williams et al. |
| 5,143,063 | A | | 9/1992 | Fellner |
| 5,158,867 | A | | 10/1992 | McNally et al. |
| 5,226,914 | A | | 7/1993 | Caplan et al. |
| 5,234,608 | A | | 8/1993 | Duff |
| 5,261,612 | A | | 11/1993 | Ftaiha |
| 5,312,380 | A | | 5/1994 | Alchas et al. |
| 5,372,945 | A | | 12/1994 | Alchas et al. |
| 5,409,833 | A | | 4/1995 | Hu et al. |
| 5,436,135 | A | | 7/1995 | Tayot et al. |
| 5,470,307 | A | | 11/1995 | Lindall |
| 5,486,359 | A | | 1/1996 | Caplan et al. |
| 5,521,087 | A | | 5/1996 | Lee et al. |
| 5,562,646 | A | * | 10/1996 | Goldman et al. ............. 604/368 |
| 5,591,625 | A | | 1/1997 | Gerson et al. |
| 5,641,622 | A | | 6/1997 | Lake et al. |
| 5,653,689 | A | | 8/1997 | Buelna et al. |
| 5,654,186 | A | | 8/1997 | Cerami et al. |
| 5,686,262 | A | | 11/1997 | Fink et al. |
| 5,686,289 | A | | 11/1997 | Humes et al. |
| 5,688,531 | A | | 11/1997 | Benayahu |
| 5,713,860 | A | | 2/1998 | Kaplan et al. |
| 5,728,739 | A | | 3/1998 | Ailhaud et al. |
| 5,736,396 | A | | 4/1998 | Bruder et al. |
| 5,744,360 | A | | 4/1998 | Hu et al. |
| 5,783,408 | A | | 7/1998 | Hamilton et al. |
| 5,785,965 | A | | 7/1998 | Pratt et al. |
| 5,786,207 | A | | 7/1998 | Katz et al. |
| 5,811,094 | A | | 9/1998 | Caplan et al. |
| 5,817,050 | A | | 10/1998 | Klein |
| 5,827,735 | A | | 10/1998 | Young et al. |
| 5,827,740 | A | | 10/1998 | Pittenger |
| 5,827,897 | A | | 10/1998 | Ailhaud et al. |
| 5,830,714 | A | | 11/1998 | Swaminathan et al. |
| 5,830,741 | A | | 11/1998 | Dwulet et al. |
| 5,837,235 | A | | 11/1998 | Mueller et al. |
| 5,837,444 | A | | 11/1998 | Shah et al. |
| 5,837,539 | A | | 11/1998 | Caplan et al. |
| 5,851,832 | A | | 12/1998 | Weiss et al. |
| 5,854,292 | A | | 12/1998 | Ailhaud et al. |
| 5,869,037 | A | | 2/1999 | Crystal et al. |
| 5,906,934 | A | | 5/1999 | Grande et al. |
| 5,908,784 | A | | 6/1999 | Johnstone et al. |
| 5,916,743 | A | | 6/1999 | Lake et al. |

(Continued)

FOREIGN PATENT DOCUMENTS

| | | |
|---|---|---|
| CN | 1287166 | 3/2001 |
| EP | 0 418 979 | 3/1991 |

(Continued)

OTHER PUBLICATIONS

Abbate, A., Biondi-Zoccai, G.G. and Baldi, A. (2002) "Pathophysiologic role of myocardial apoptosis in post-infarction left ventricular remodeling" J Cell Physiol 193, 145-33.

Aharinejad, S., Mars, S.C., Jr., Bock P., Mason-Savas, A., MacKay, C.A. Larson, E.K., Jackson, M.E., Luftensteiner, M. and Weisbauer, E. (1995) "CSF-1 treatment promotes angiogenesis in the metaphysics of osteopetrotic (toothless, tl) rats" Bone 16, 315-324.

Ahrens, Patricia Buckley et al., "Stage-Related Capacity for Limb Chondrogenesis in Cell Culture," *Developmental Biology,* 1977, 60:69-82.

Ailhaud, et al., 1983, "Hormonal requirements for growth and differentiation of OB17 preadipocyte cells in vitro," *Diabete & Metabolisme,* vol. 9:125-133.

(Continued)

*Primary Examiner* — Catherine S. Hibbert

*Assistant Examiner* — Channing S Mahatan

(74) *Attorney, Agent, or Firm* — DLA Piper LLP (US)

(57) ABSTRACT

Disclosed herein are methods and systems for the concentration of cells from a cell suspension into unprocessed tissue, such as adipose tissue. Also disclosed herein are systems for optimizing hydration of tissue and cell enriched grafts.

20 Claims, 15 Drawing Sheets

(56) References Cited

U.S. PATENT DOCUMENTS

| | | | |
|---|---|---|---|
| 5,952,215 | A | 9/1999 | Dwulet et al. |
| 5,968,356 | A | 10/1999 | Morsiani |
| 5,980,887 | A | 11/1999 | Isner et al. |
| 6,001,642 | A | 12/1999 | Tsao |
| 6,010,696 | A | 1/2000 | Caplan et al. |
| 6,020,196 | A | 2/2000 | Hu et al. |
| 6,030,836 | A | 2/2000 | Thiede et al. |
| 6,043,066 | A | 3/2000 | Mangano et al. |
| 6,086,582 | A | 7/2000 | Altman et al. |
| 6,090,121 | A | 7/2000 | Weber et al. |
| 6,139,757 | A | 10/2000 | Ohmura |
| 6,197,325 | B1 | 3/2001 | MacPhee et al. |
| 6,200,606 | B1 | 3/2001 | Peterson et al. |
| 6,206,873 | B1 | 3/2001 | Paolini et al. |
| 6,221,315 | B1 | 4/2001 | Giesler et al. |
| 6,238,908 | B1 | 5/2001 | Armstrong et al. |
| 6,251,295 | B1 | 6/2001 | Johnson |
| 6,261,549 | B1 | 7/2001 | Fernandez et al. |
| 6,277,060 | B1 | 8/2001 | Neumann |
| 6,316,247 | B1 | 11/2001 | Katz et al. |
| 6,322,784 | B1 | 11/2001 | Pittenger et al. |
| 6,355,239 | B1 | 3/2002 | Bruder et al. |
| 6,368,356 | B1 | 4/2002 | Zhong et al. |
| 6,387,369 | B1 | 5/2002 | Pittenger et al. |
| 6,429,013 | B1 | 8/2002 | Halvorsen et al. |
| 6,436,639 | B1 | 8/2002 | Kiefer et al. |
| 6,451,207 | B1 | 9/2002 | Sterman et al. |
| 6,475,764 | B1 | 11/2002 | Burtscher et al. |
| 6,517,526 | B1 * | 2/2003 | Tamari .......................... 604/403 |
| 6,576,464 | B2 | 6/2003 | Gold et al. |
| 6,589,728 | B2 | 7/2003 | Csete et al. |
| 6,623,959 | B2 | 9/2003 | Harris |
| 6,669,905 | B1 * | 12/2003 | Mathias et al. ............... 604/406 |
| 6,689,352 | B2 | 2/2004 | Achen et al. |
| 6,777,231 | B1 | 8/2004 | Katz et al. |
| 6,804,558 | B2 | 10/2004 | Haller et al. |
| 7,078,230 | B2 | 7/2006 | Wilkison |
| 7,390,484 | B2 * | 6/2008 | Fraser et al. ................. 424/93.7 |
| 7,514,075 | B2 | 4/2009 | Hedrick et al. |
| 7,585,670 | B2 | 9/2009 | Hedrick et al. |
| 7,651,684 | B2 * | 1/2010 | Hedrick et al. .............. 424/93.7 |
| 7,767,452 | B2 | 8/2010 | Kleinsek |
| 7,771,716 | B2 | 8/2010 | Hedrick et al. |
| 7,887,795 | B2 * | 2/2011 | Fraser et al. ................. 424/93.7 |
| 7,901,672 | B2 * | 3/2011 | Fraser et al. ................. 424/93.7 |
| 8,053,248 | B2 * | 11/2011 | Bakaltcheva et al. ......... 436/176 |
| 8,105,580 | B2 | 1/2012 | Fraser et al. |
| 8,119,121 | B2 | 2/2012 | Fraser et al. |
| 8,163,276 | B2 | 4/2012 | Hedrick et al. |
| 8,246,947 | B2 | 8/2012 | Hedrick et al. |
| 8,404,229 | B2 | 3/2013 | Fraser et al. |
| 2001/0000802 | A1 | 5/2001 | Soykan et al. |
| 2001/0009757 | A1 | 7/2001 | Bischof et al. |
| 2002/0103542 | A1 | 8/2002 | Bilbo |
| 2002/0111694 | A1 | 8/2002 | Ellingsen et al. |
| 2002/0182211 | A1 | 12/2002 | Peach et al. |
| 2003/0014126 | A1 | 1/2003 | Patel et al. |
| 2003/0026759 | A1 | 2/2003 | Ferrell et al. |
| 2003/0054331 | A1 | 3/2003 | Fraser et al. |
| 2003/0069168 | A1 | 4/2003 | Xu et al. |
| 2003/0075516 | A1 * | 4/2003 | Rothman et al. .............. 210/806 |
| 2003/0082152 | A1 | 5/2003 | Hedrick et al. |
| 2003/0100105 | A1 | 5/2003 | Poo et al. |
| 2003/0152558 | A1 | 8/2003 | Luft et al. |
| 2003/0161816 | A1 | 8/2003 | Fraser et al. |
| 2003/0161817 | A1 | 8/2003 | Young et al. |
| 2003/0162707 | A1 | 8/2003 | Fraser et al. |
| 2003/0211085 | A1 | 11/2003 | Sanberg et al. |
| 2003/0211602 | A1 | 11/2003 | Atala |
| 2003/0212024 | A1 | 11/2003 | Keating et al. |
| 2004/0067218 | A1 | 4/2004 | Casteilla et al. |
| 2004/0197304 | A1 | 10/2004 | Chen et al. |
| 2005/0008626 | A1 | 1/2005 | Fraser et al. |
| 2005/0025755 | A1 * | 2/2005 | Hedrick et al. ............ 424/93.21 |
| 2005/0084961 | A1 | 4/2005 | Hedrick et al. |
| 2005/0271636 | A1 | 12/2005 | Oliver et al. |
| 2006/0025338 | A1 | 2/2006 | Alitalo et al. |
| 2006/0088532 | A1 | 4/2006 | Alitalo et al. |
| 2007/0111935 | A1 | 5/2007 | Franco et al. |
| 2007/0148766 | A1 | 6/2007 | Yoshimura et al. |
| 2007/0212676 | A1 | 9/2007 | Takakura et al. |
| 2007/0233038 | A1 | 10/2007 | Pruitt et al. |
| 2009/0104159 | A1 | 4/2009 | Prosper et al. |
| 2010/0015104 | A1 | 1/2010 | Fraser et al. |

FOREIGN PATENT DOCUMENTS

| | | |
|---|---|---|
| EP | 0 446 450 | 9/1991 |
| EP | 0 448 770 | 10/1991 |
| EP | 0 512 769 | 11/1992 |
| EP | 0 515 726 | 12/1992 |
| EP | 0 570 331 | 11/1993 |
| EP | 0 987 325 | 3/2000 |
| EP | 1 077 254 | 2/2001 |
| EP | 1 011 752 | 10/2004 |
| EP | 1 712 616 | 10/2006 |
| JP | 59-090649 | 5/1984 |
| JP | 01-141583 | 6/1989 |
| JP | 02-002884 | 1/1990 |
| JP | 02-295484 | 12/1990 |
| JP | 04-183381 | 6/1992 |
| JP | 04-267873 | 9/1992 |
| JP | 7-255469 | 10/1995 |
| JP | 08-208401 | 8/1996 |
| JP | 08-259604 | 10/1996 |
| JP | 9-255588 | 9/1997 |
| JP | 10-17310 | 1/1998 |
| JP | 11-4682 | 1/1999 |
| JP | 11-57731 | 3/1999 |
| JP | 2000-325068 | 11/2000 |
| JP | 2003-024040 | 1/2003 |
| JP | 2001-231539 | 8/2003 |
| JP | 2004-272762 | 9/2004 |
| WO | WO 86/01111 | 2/1986 |
| WO | WO 87/03812 | 7/1987 |
| WO | WO 94/02156 | 2/1994 |
| WO | WO 94/27698 | 12/1994 |
| WO | WO 96/38482 | 12/1996 |
| WO | WO 97/18299 | 5/1997 |
| WO | WO 97/26326 | 7/1997 |
| WO | WO 97/39104 | 10/1997 |
| WO | WO 97/40137 | 10/1997 |
| WO | WO 97/41208 | 11/1997 |
| WO | WO 97/49827 | 12/1997 |
| WO | WO 98/04682 | 2/1998 |
| WO | WO 98/20731 | 5/1998 |
| WO | WO 98/32333 | 7/1998 |
| WO | WO 98/51317 | 11/1998 |
| WO | WO 99/01145 | 1/1999 |
| WO | WO 99/02654 | 1/1999 |
| WO | WO 99/03973 | 1/1999 |
| WO | WO 99/11789 | 3/1999 |
| WO | WO 99/28444 | 6/1999 |
| WO | WO 00/53795 | 9/2000 |
| WO | WO 01/21767 | 3/2001 |
| WO | WO 01/62901 | 8/2001 |
| WO | WO 02/055678 | 7/2002 |
| WO | WO 02/064157 | 8/2002 |
| WO | WO 02/068010 | 9/2002 |
| WO | WO 02/075302 | 9/2002 |
| WO | WO 02/081007 | 10/2002 |
| WO | WO 03/001329 | 1/2003 |
| WO | WO 03/022988 | 3/2003 |
| WO | WO 03/024215 | 3/2003 |
| WO | WO 03/039481 | 5/2003 |
| WO | WO 03/053346 | 7/2003 |
| WO | WO 03/053362 | 7/2003 |
| WO | WO 03/080801 | 10/2003 |
| WO | WO 2004/013275 | 2/2004 |
| WO | WO 2004/029230 | 4/2004 |
| WO | WO 2004/052418 | 6/2004 |
| WO | WO 2004/072828 | 8/2004 |
| WO | WO 2004/074457 | 9/2004 |
| WO | WO 2004/093934 | 11/2004 |

(56) References Cited

FOREIGN PATENT DOCUMENTS

| | | |
|---|---|---|
| WO | WO 2004/101015 | 11/2004 |
| WO | WO 2005/012480 | 2/2005 |
| WO | WO 2005/034843 | 4/2005 |
| WO | WO 2005/035738 | 4/2005 |
| WO | WO 2005/035742 | 4/2005 |
| WO | WO 2005/063967 | 7/2005 |

OTHER PUBLICATIONS

Ailhaud, et al., 1985, "Lipoprotiene lipase et differenciation adipocytaire," *Reprod. Nutr. Develop.*, vol. 25:153-158.
Alameddine, Hala S. et al., "Regeneration of Skeletal Muscle Fibers from Autologous Satellite Cells Multiplied In Vitro. An Experimental Model for Testing Cultured Cell Myogenicity," *Muscle & Nerve*, 1989, 12:544-55.
Alhadlaq et al. "Engineered adipose tissue from human mesenchymal stem cells maintains predefined shape and dimension: implications in soft tissue augmentation and reconstruction." *Tissue Eng* 11, 556-566 (2005).
Anderson, Apr. 30, 1998, Human Gene Therapy, Nature, 392 Supp (6679):25-30.
Angele, P. et al., "Engineering of Osteochondral Tissue with Bone Marrow Mesenchymal Progenitor Cells Derivatized Hyaluronan-Gelatin Composite Sponge," *Tissue Engineering*, 1999, 5:545-53.
Ankrom, Michael A., "Age-related changes in human oestrogen receptor function and levels in osteoblasts," Biochem J. 333:787-794.
Aragona, F., L. D'Urso et al (1998) "Immunologic aspects of bovine injectable collagen in humans. A review" Eur Urol 33(2): 129-33.
Arts et al., 2002, Contaminants from the Transplant Contribute to Intimal Hyperplasia Associated with Microvascular Endothelial Cell Seeding, Eur. J. Endovasc. Surg. 23:29-38.
Arvidsson, A., Collin, T., Kirik, D., Kokaia, Z., and Lindvall, O. (2002) "Neuronal replacement from endogenous precursors in the adult brain after stroke" Nat Med 8, 963-70.
Ashjian, P.H. Elbarbary, A.S., Edmonds, B., DeUgarte, D., Zhu, M., Zuk, P.A., Lorenz, H.P., Benhaim, P., and Hedrick, M.H. (2003). "In vitro differentiation of human processed lipoaspirate cells into early neural progenitors" Plast Reconstr Surg 111 1922-31.
Asken, S. (1990) "Microliposuction and autologous fat transplantation for aesthetic enhancement of the aging face" J Dermatol Surg Oncol 16(10): 965-72.
Aso, Hisashi, et al., "A Preadipocyte Clonal Line from bovine Intramuscular Adipose Tissue: Nonexpression of GLUT-4 protein during Adipocyte Differentiation," *Biochem. Biophys. Res. Commun.* 213:369-375.
Asou, Y., Rittling, S.R., Yoshitake, H., Tsuji, K., Shinomiya, K., Nifuji, A., Denhardt, D.T., and Noda, M. (2001) "Osteopontin facilitates angiogenesis, accumulation of osteoclasts, and resorption in ectopic bone" Endocrinology 142, 1325-1332.
Assady, S., Maor, G., Amit, M., Itskovitz-Eldor, J., Skorecki, K.L., and Tzukerman, M. (2001) "Insulin production by human embryonic stem cells" Diabetes 50, 1691-7.
Assmus, B., Schachinger, V., Teupe, C., Britten,M., Lehmann, R., Dobert, N., Grunwald, F., Aicher, A., Urbich, C., Martin, H., Hoelzer, D., Dimeler, S., and Zeiher, A.M. (2002) Transplantation of Progenitor Cells and Regeneration Enhancement in Acute Myocardial Infarction (TOPCARE-AMI) Circulation 106, 3009-17.
Athanasopoulos, T., Fabb, S., and Dickson, G. (2000) "Gene therapy vectors based on adeno-associated virus: characteristics and applications to acquired and inherited diseases (review)" Int J Mol Med 6, 363-75.
ATTC Preservation Methods: Freezing and Free-Drying, ATCC, 2nd Edition, 1991.
Avital, I., D. Inderbitzin, et al. (2001) "Isolation, characterization and transplantation of bone marrow-derived hepatocyte stem cells" Biochem Biophys Res Commun 288(1): 156-64.
Badiavas, et al. "Participation of bone marrow derived cells in cutaneous would healing." Journal of Cellular Physiology. 196(2): 245-250 (2003).
Bagnato et al., Jan. 2002, Emerging role of endothelin-1 in tumor angiogenesis, Trends in Endocrinology and Metabolism, 14(1):44-50.
Bailey, A. J. et al., "Age-Related Changes in the Biochemical Properties of Human Cancellous Bone Collagen: Relationship to Bone Strength," *Calcified Tissue International*, 1999, 65:203-10.
Banerji et al., Feb. 22, 1999, LYVE-1, a New Homologue of the CD44 Glycoprotein, Is a Lymph-specific Receptor for Hyaluronan, J. Cell Biology, 144(4):789-801.
Banfi, A., Bianchi, G., Galotto, M., Cancedda, R., and Quarto, R. (2001) "Bone marrow stromal damage after chemo/radiotherapy: occurrence, consequences and possibilities of treatment" Leuk Lymphoma 42, 863-70.
Barghorn, A. et al., "A-Smooth Muscle Actin Distribution in the Pulmonary Vasculature Comparing Hypoplastic and Normal Fetal Lungs," *Pediatric Pathology & Laboratory Medicine*, 1998, 18:5-22.
Barker, J.N., Davies, S.M., DeFor, T., Ramsay, N.K., Weisdorf, D.J. and Wagner, J.E. (2001) "Survival after transplantation of unrelated donor umbilical cord blood is comparable to that of huan leukocyte antigen-matched unrelated donor bone marrow: results of a matched-pair analysis" Blood 97, 2957-61.
Baron et al., 1999, Acute Necrotizing Pancreatitis, The New Engl. J. Med. 340:1412-1417.
Barry, F.P., Boynton, R.E., Haynesworth, S., Murphy, J.M., and Zaia, J. (1999) "The monoclonal antibody SH-2, raised against human mesenchymal stem cells, recognizes an epitope on endoglin (CD105)" Biochem Biophys Res Commun 265, 134-9.
Bartynski, J.M., S. Marion et al. (1990) "Histopathologic evaluation of adipose autografts in a rabit ear model" Otolaryngol Hea Neck Surg 102(4): 314-21.
Bastard, J. P. et al., "A Mini-Liposuction Technique Adapted to the Study of Human Adipocyte Glucose Transport System," *Diabetologia*, 36(Suppl. 1):A135, 1993.
Baylink, David J., "Glucocorticoid-Induced Osteoporosis," *The New England Journal of Medicine*, 1983, 309:306-8.
Becerra, José et al., "Demineralized Bone Matrix Mediates Differentiation of Bone Marrow Stromal Cells In Vitro: Effect of Age of Cell Donor," *Journal of Bone and Mineral Research*, 1996, 11:1703-14.
Beecken, W.D., Kramer, W., and Jonas, D. (2000) "New molecular mediators in tumor angiogenesis" J Cell Mol Med 4, 262-269.
Beiser, Ian H. and Irvin O. Kanat, "Subchondral Bone Drilling: A Treatment for Cartilage Defects," *Journal of Foot Surgery*, 1990, 29:595-601.
Bender et al., 1991, Identification and comparison of CD34-positive cells and their subpopulations from normal peripheral blood and bone marrow using multicolor flow cytometry, Blood 77(12): 2591-2596.
Bennett, JH, et al., 1991 *J. Cell Sci.* "Adipocytic cells cultured from marrow have osteogenic potential," 99(Pt1):131-139.
Berdel, W.E., Fink, U., Thiel, E., Stunkel, K., Greiner, E., Schwarzkopf, G., Reichert, A. and Rastetter, J. (1982) "Purification of human monocytes by adherence to polymeric fluorocarbon. Characterization of the monocyte-enriched cell fraction" Immunobiology 163, 511-520.
Beresford, et al., 1986 *Endo.* "1,25-Dihydroxyvitamin D3 and Human Bone-Derived Cells in Vitro: Effects on Alkaline Phosphatase, Type I Collagen and Proliferation," 119:1776-1785.
Bergeon, M.T. (1967) "Collagen: a review" J Okla State Med Assoc 60(6): 330-2.
Bernlohr, David A. et al., "Tissue Specific Expression of p422 protein , A putative Lipid Carrier, In Mouse Adipocytes," *Biochem. Biophys. Res. Comun.* 1985 132:850-855.
Berry et al., 2005, The Establishment of a Predictive Mutational Model of the Forkhead Domain through the Analyses of FOXC2 Missense Mutations Identified in Patients with Hereditary Lymphedema with Distichiasis, Human Molecular Genetics 14(18):2619-2627.
Bianco et al., Apr. 2008, Mesenchymal stem cells: revisiting histo, concepts, and assays, Cell Stem Cell, 2:313-319.
Bickenbach, J.R. and Dunnwald, M. (2000) "Epidermal stem cells: characteristics and use in tissue engineering and gene therapy" Adv Dermatol 16, 159-83.

(56) References Cited

OTHER PUBLICATIONS

Bjornson, et al., 1999 *Science* "Turning Brain into Blood: A Hematopoetic Fate Adopted by Adult Neural Stem Cells in Vivo," 283:534-537.
Bjorntorp et al., 1980 Differentiation and function of rat adipocyte precursor cells in primary culture, J. Lipid Research 21:714-723.
Björntrop, et al. "Isolation and characterization of cells from rat adipose tissue developing into adipocytes." J. Lipid Res. 19:316-324 (1978).
Block, C.A., C.S. Cooper (2003) "Long-term Efficacy of periurethral collagen injection for the treatment of urinary incontinence secondary to myelomeningocele" J Urol 169(1): 327-329.
Boering, G. and A.J. Huffstadt (1967) "The use of derma-fat grafts in the face" Br J Plast Surg 20(2): 172-8.
Boerner, C.F. (1988) "Allergic response to a porcine collagen corneal shield. Case report" Arch Opthalmol 106(2): 171.
Boghossian et al, 2005, Suppression of fat deposition for the life time with gene therapy, Peptides 26(8):1512-1519.
Bond et al., 1999, "Human Subcutaneouspreadipocytes Differentiate Into osteoblasts," *FASEB Journal* 13:600A.
Bonner-Weir, S. and Sharma, A. (2002) "Pancreatic stem cells" J Pathol 197, 519-526.
Boskey, et al., 1985, "The Effect of Osteocalcin on In Vitro Lipid-Induced Hydroxyapatite Formation and Seeded Hydroxyapatite Growth," *Calc. Tiss. Int.* 37:75.
Breen, Ellen C. et al., "TGFb Alters Growth and Differentiation Related Gene Expression in Proliferating Osteoblasts In Vitro, Preventing Development of the Mature Bone Phenotype," *Journal of Cellular Physiology,* 1994, 160:323-35.
Breiteneder-Geleff et al., Feb. 1999, Angiosarcomas Express Mixed Endothelial Phenotypes of Blood and Lymphatic Capillaries, Am. J. Path. 154(2): 385-394.
Bruder, et al., 1997 J. Cell Biochem. "Growth Kinetics, Self-Renewal, and the Osteogenic Potential of Purified Human Mesenchymal Stem Cells During Extensive Subcultivation and Following Cryopreservation," 64:278-294.
Bruder, Scott P. et al., "Bone Regeneration by Implantation of Purified, Culture-Expanded Human Mesenchymal Stem Cells," *Journal of Orthopaedic Research,* 1998, 16:155-62.
Bulleid, J.J., D.C. John et al (2000) "Recombinant expression systems for the production of collagen" Biochem Soc Trans 28(4): 350-3.
Burres, S. (2001) "Soft-tissue augmentation with fascian" Clin Plast Surg 28(1): 101-10.
Buschmann, I.R. Busch, H.J., Mies, G., and Hossmann, K.A. (2003) "Therapeutic induction of arteriogenesis in hypoperfused rat brain via granulocyte-macrophage colony-stimulating factor" Circulation 108, 610-615.
Butler-Browne, et al., 1990 *Anat. Embryol.* (*Berl*) "Myosin heavy and light chain expression during human skeletal muscle development and precocious muscle maturation induced by thyroid hormone," 181:513-522.
Butnariu-Ephrat, Miriam et al., "Resurfacing of Goat Articular Cartilage by Chondrocytes Derived From Bone Marrow," *Clinical Orthopaedics and Related Research,* 1996, 330:234-43.
Campion, Dennis R., "The Muscle Satellite Cell: A Review," *Internationals Review of Cytology,* 1984, 87:225-51.
Caplan, A.I. and Bruder, S.P. (2001) "Mesenchymal stem cells: building blocks for molecular medicine in the 21st century" Trends Mol Med 7, 259-64.
Caplan, Arnold I., "Mesenchymal Stem Cells," *Journal of Orthopaedic Research,* 1991, 9:641-50.
Caplan, Arnold I., "The Mesengenic Process," *Clinics in Plastic Surgery,* 21:429-35, 1994.
Carano, R.A. and Filvaroff, E.H. (2003) "Angiogenesis and bone repair" Drug Discov. Today 8, 980-989.
Carmeliet, P. (2000) "Mechamisms of angiogenesis and arteriogenesis" Nat Med 6, 389-395.
Carmeliet, P. and A. Luttun (2001) "The emerging role of the bone marrow-derived stem cells in (therapeutic angiogenesis" Thromb Haemost 86(1): 289-97.
Carpandena, C.A. "Collagen alterations in adipose autograft's." Aesthetic Plastic Surgery vol. 18, 11-15 (1994).
Carranza-Bencano, A. et al., "Comparative Study of the Reconstruction of Articular Cartilage Defects with Free Costal Perichondrial Grafts and Free Tibial Periosteal Grafts: An Experimental Study on Rabbits," *Calcified Tissue International,* 1999, 65:402-7.
Casteilla et al., Apr. 26, 2011, Adipose-derived stromal cells: their identity and uses in clinical trials, an update, World J. Stem Cells, 3(4):25-33.
Castro, et al. "Failure of Bone Marrow Cells to Transdifferentiate into Neural Cells in Vivo." Science. 297:1299 (2002).
Castro, et al. "Response to Comment on 'Failure of Bone Marrow Cells to Transdifferentiate into Neural Cells in Vivo.'" Science. 299:1184c (2003).
Castro-Malaspina, H., W. Ebell, et al. (1984) "Human bone marrow fibroblast colony-forming units (CFU-F" Prog Clin Ciol Res 154: 209-36.
Cavallini, 2007, Autologous Fibroblasts to Treat Deep and Complicated Leg Ulcers in Diabetic Patients, Wound Repair Regen. 15(1):35-8.
Chang et al., Jan. 2006, Characterization of two populations of mesenchymal progenitor cells in umbilical cord blood, Cell Biology International, 40:495-499.
Cheifetz, S. et al., "Endoglin is a Component of the Transforming Growth Factor-β Receptor System in Human Endothelial Cells," *J. Biol. Chem.,* 1992 267:19027-19030.
Chen et al., Dec. 2005, Novel Expression and Characterization of Lymphatic Vessel Endothelial Hyaluronate Receptor 1 (LYVE-1) by Conjunctival Cells, Invest. Ophthalmol. Vis. Sci. 46(12):4536-4540.
Chen, J. et al. Intravenous Administration of Human Bone Marrow Stromal Cells Induces Angiogenesis in the Ischemic Boundary Zone After Stroke in Rats, Circulation Research, Apr. 2003, vol. 92, pp. 692-699.
Chen, J. et al. Intravenous Bone Marrow Stromal Cell Therapy Reduces Apoptosis and Promotes Endogenous Cell Proliferation After Stroke in Femal Rat, J. Neuroscience Research, Sep. 2003, vol. 73 pp. 778-786.
Chen, Theresa L. et al., "1α,25-Dihydroxyvitamin D3 Receptors in Cultured Rat osteoblast-like Cells," J. Biol. Chem. 1983 258:4350-4355.
Chen, Xiaoli et al., "Differentiation-dependent expression of obese (ob) gene by preadipocytes and adipocytes in primary cultures of porcine stromal-vascular cells," *Biochimica et Biophysica Acta,* 1997, 1359:136-42.
Cheng S-L., et al., 1994 *Endo* "Differentiation of Human Bone Marrow Osteogenic Stromal Cells in Vitro: Induction of the Osteoblast Phenotype by Dexamethasone," 134: 277-286.
Chimal-Monroy, Jesús and Lino Diaz de León, "Expression of N-cadherin, N-CAM, fibronectin tenascin is stimulated by TGF-b1, b2, b3 and b5 during the formation of precartilage condensations," *The International Journal of Developmental Biology,* 1999, 43:59-67.
Cho,S.W. et al. "Engineering of volume-stable adipose tissues." *Biomaterials* 26, 3577-3585 (2005).
Cho,S.W. et al. "Enhancement of adipose tissue formation by implantation of adipogenic-differentiated preadipocytes." *Biochem Biophys Res Commun* 345, 588-594 (2006).
Choi et al. "Adipose tissue engineering using mesenchymal stem cells attached to injectable PLGA spheres." *Biomaterials* 26, 5855-5863 (2005).
Choi,Y.S. et al. "Adipogenic differentiation of adipose tissue derived adult stem cells in nude mouse." *Biochem Biophys Res Commun* 345, 631-637 (2006).
Chyun, et al., 1984 *Endo.* "Cortisol Decreases Bone Formation by Inhibiting Periosteal Cell Proliferation," 114:477-480.
Civin, C.I., Strauss, L.C., Fackler, M.J., Trischmann, T.M., Wiley, J.M., and Loken, M.R. (1990) "Positive stem cell selection-basic science" Prog Clin Biol Res 333, 387-401.
Clarke, D. and Frisen, J. (2001) "Differentiation potential of adult stem cells" Curr Opin Genet Dev 11, 575-80.

(56) References Cited

OTHER PUBLICATIONS

Clavijo-Alvarez,J.A. et al. "A novel perfluoroelastomer seeded with adipose-derived stem cells for soft-tissue repair." *Plast Reconstr Surg* 118, 1132-1142 (2006).
Coleman III, et al. "Autologous Collagen? Lipocytic Dermal Augmentation. A Histopathologic Study". J. Dermatol Surg Oncol. vol. 19, 1032-1040 (1993).
Coleman, S.R. (1995) "Long-term survival of fat transplants: controlled demonstrations" Aesthetic Plast Surg 19(5): 421-5.
Coleman, S.R. (2001). "Structural fat grafts: the ideal filler?" Clin Plast Surg 28(1): 111-9.
Coleman, W.P., 3rd (1991) "Autologous fat transplantation" Plast Reconstr Surg 88(4): 736.
Colombo et al., Feb. 7, 2003, Opposite effects of background genotype on muscle and liver insulin sensitivity of lipoatrophic mice, J Biol Chern. 278(6):3992-3999.
Commons, G.W., Halperin, B., and Chang, C.C. (2001) "Large-volume liposuction: a review of 631 consecutive cases over 12 years" Plast Reconstr Surg 108, 1753-63.
Conget, PA and JJ Minguell 1999 *J. Cell. Physiol* "Phenotypical and Functional Properties of Human Bone Marrow Mesenchymal Progenitor Cells," 181:67-73.
Connolly, J.F. (1998) "Clinical use of marrow osteoprogenitor cells to stimulate osteogenesis" Clin Orthop(355 Suppl): S257-66.
Considine, et al., "Paracrine stimulation of preadipocyte-enriched cell cultures by mature adipocytes," *American Journal of Physiology* 1996 270(5) E895-E899.
Cooper, et al., 1999 *J. Endocrinol.* "Glucocorticoid activity, inactivity and the osteoblast," 163: 159-164.
Crandall, David L. et al., "Identification of Estrogen Receptor b RNA in Human Breast and Abdominal Subcutaneous Adipose Tissue," *Biochemical and Biophysical Research Communications,* 248:523-6, 1998.
Crevensten et al. "Intervertebral Disc Cell Therapy for Regeneration: Mesenchymal Stem Cell Implantation in Rat Intervertebral Discs." Annals of Biomedical Engineering. 32(3):430-434 (2004).
Cronin,K.J. et al. "New murine model of spontaneous autologous tissue engineering, combining an arteriovenous pedicle with matrix materials." *Plast Reconstr Surg* 113, 260-269 (2004).
Dani, et al., "Differentiation of embryonic stem cells into adipocytes in vitro," *J. Cell Sci.* 1997 110, 1279-1285.
Davis, P.F. and Z.M. Mackie (1981) "A simple procedure for the separation of insoluble collagen and elastin" Anal Biochem 115(1): 11-7.
Dawra et al., Apr. 2007, Development of a new mouse model of acute pancreatitis induced by administration of L-arginine, Am J Physiol Gastrointest Liver Physiol. 292(4):G1009-1018.
de la Fuente et al., 2004, Dedifferentiated adult articular chondrocytes: a population of human multipotent primitive cells, Exp. Cell Res. 297(2): 313-28.
De Ugarte et al., 2003, Differential expression of stem cell mobilization-associated molecules on multi-lineage cells from adipose tissue and bone marrow, Immunology Letters, 89:267-270.
De Ugarte et al., 2003, Future of fat as raw material for tissue regeneration, Ann Plast Surg 50, 215-9.
Deng, Weiwen et al., "In Vitro Differentiation of Human Marrow Stromal Cells into Early Progenitors of Neural Cells by Conditions That Increase Intracellular Cyclic AMP," *Biochemical and Biophysical Research Communications,* 2001, 282:148-52.
Dengler T et al. 2002. Stem Cell Therapy for the Infarcted Heart ("Cellular Cardiomyoplasty"), Herz 27:598-610.
Denker, A.E., et al., 1995 *Differentiation* "Formation of cartilage-like spheroids by micromass cultures murine C3H101/2 cells upon treatment with transforming growth factor-b1," 59: 25-34.
Denker, et al., 1999 *Differentiation* "Chondrogenic differentiation of murine C3H10T1/2 multipotential mesenchymal cells: I. Stimulation by bone morphogenetic protein-2 in high-density micromass cultures," 64:67-76.
Dennis, James E. et al., "A Quadripotential Mesenchymal Progenitor Cell Isolated from the Marrow of an Adult Mouse," *Journal of Bone and Mineral Research,* 1999, 14:700-9.
Dias, Peter et al., "The Molecular Basis of Skeletal Muscle Differentiation," *Seminars in Diagnostic Pathology,* 1994, 11:3-14.
Diefenderfer, David L. and Carl T. Brighton, "Microvascular Pericytes Express Aggrecan Message Which is Regulated by BMP-2," *Biochemical and Biophysical Research Communications,* 2000, 269:172-8.
Dimri, et, al., 1995 *Proc. Natl. Acad. Sci. USA* "A biomarker that identifies a senescent human cells in culture and in aging skin in vivo," 92: 9363-9367.
D'Ippolito, G., Schiller, P.C., Ricordi, C., Roos, B.A., and Howard, G.A. (1999) "Age-related osteogenic potential of mesenchymal stromal stem cells from human vertebral bone marrow" J Bone Miner Res 14, 1115-22.
Donovan, D., Brown, N.J., Bishop, E.T. and Lewis, C.E. (2001) "Comparison of three in vitro human 'angiogenesis' assays with capillaries formed in vivo" Angiogenesis 4, 113-121.
Dragoo et al., 2003, Bone induction by BMP-2 transduced stem cells derived from human fat, J. Orth. Res., 21:622-629.
Dragoo et al. "Tissue-engineered cartilage and bone using stem cells derived from human infrapetellar fat pads." The Journal of Bone and Joint Surgery. 85(5):740-747 (2003).
Ducy, et, al., 1997 *Cell* "Osf2/Cbfa1: A Transcriptional Activator of Osteoblast Differentiation," 89:747-754.
Duxbury et al., 2004, Lymphangiogenesis in tissue-engineered small intestine, Transplantation 77(8):1162-6.
Eisenberg, Shlomo, "High density lipoprotein metabolism," *Journal of Lipid Research,* 1984, 25:1017-58.
El-Ghalbzouri et al., 2004, Cutaneous biology: human adipose tissue-derived cells delay re-epithelialization in comparison with skin fibroblasts in organotypic skin culture, British Journal of Dermatology, 150(3):444-454.
Engleholm, S.A., Spang-Thomsen, M., Brunner N., Nohr, I., and Vindelov, L.L. (1985) "Disaggregation of human solid tumors by combined mechanical and enzymatic methods" Br J Cancer 51, 93-8.
Enomoto, Hirayuki et al., "Cbfal Is a Positive Regulatory Factor in Chondrocyte Maturation," J. Biol. Chem. 2000 275:8695-8702.
Entenmann, et al., "Relationship between replication and differentiation cultured human adipocyte precursor cells," *American Phys. Soc.* 1996 270,C1011-C1016.
Eppley, B.L., Smith, P.G., Sadove, A.M., and Delvino, J.J. (1990) "Experimental effects of graft revascularization and consistency on cervicofacial fat transplant survival" J Oral Maxillofac Surg 48, 54-62.
Eremia, S. and N. Newman (2000). "Long-term follow-up after autologous fat grafting: analysis of results from 116 patients followed at least 12 months after receiving the last of a minimum of two treatments" Dermatol Surg 26(12): 1150-8.
Erickson et al. "Chondrogenic potential adipose tissue derived stromal cells in vitro and in vivo." Biochemical and Biophysical Research Communications. 290(2):763-769 (2002).
Ersek, Robert A. "Transplantation of Purified Autologous Fat: A 3-Year Follow-Up is Disappointing." Plast. Reconst. Surg. 87(2):219-228 (1991).
Eschenhagen, T., Didie, M., Muzel, FI, Schubert, P. Schneiderbanger, K., and Zimmermann, W.H. (2002) "3D engineered hear tissue for replacement therapy" Basic Res Cardiol 97 Suppl 1, 1146-1152.
Fain et al. "Comparison of the Release of Adipolines by Adipose Tissue, Adipose Tissue Matrix, and Adipocytes from Visceral and Subcutaneous Abdominal Adipose Tissues of Obese Humans." Endocrinology. 145(5):2273-2282, at 2278, col. 2 (2004).
Fajas, Lluis, et al., "Transcriptional control of adipogenesis," *Current Opinion in Cell Biology,* 1998, 10:165-73.
Falla, N., Van V., Bierkens, J., Borremans, B., Schoeters, G., and Van Gorp, J. (1993) "Characterization of a 5-flurorouracil-enriched osteoprogenitor population of the murine bone marrow" Blood 82, 3580-91.
Farndale, Richard W. et al., "Improved quantitation and discrimination of sulphated glycosaminoglycans by use of dimethylene blue," *Biochimica et Biophysica Acta,* 1986, 883:173-7.

(56) References Cited

OTHER PUBLICATIONS

Ferrari G., et al., 1998 *Science* "Muscle Regeneration by Bone Marrow-Derived Myogenic Progenitors," 279: 1528-1530.
Folkman, J. (1995) "Angiogenesis in cancer, vascular, rheumatoid and other disease" Nat Med 1, 27-31.
Ford, C.N., P.A. Staskowski et al. (1995) "Autologous collagen vocal fold injection: a preliminary clinical study" Laryngoscope 105(9 Pt 1): 944-8.
Formanek, M., Temmel, A., Knerer, B., Willheim, M., Millesi, W., and Kornfehl, J. (1998) "Magnetic cell separation for purification of human oral keratinocytes: an effective method for functional studies without prior cell subcultivation" Eur Arch Otorhinolaryngol 255, 211-215.
Fortier, Lisa, et al., 2000, "Isolation and chondrocytic differentiation of equine bone marrow-derived mesenchymal stem cells," *Am. J. Vet. Res.* 59:1182-1187.
Fraser et al. "Adult Stem Cell Therapy for the Heart." The International Journal of Biochemistry & Cell Biology. 36(4):658-666 (2004).
Fraser et al., Mar. 1992, Proliferation of totipotent hematopoietic stem cells in vitro with retention of long-term competitive in vivo reconstituting ability, Cell Biology, 89(5):1968-72.
Fraser JK. Adipose Tissue: Challenging the Marrow Monopoly. Cytotherapy. 4(6):509-510 (2002).
Frederikson and McKay 1988 *J. Neurosci.* "Proliferation and Differentiation of Rat Neuroepithelial Precursor Cells in vivo," 8:1144-1151.
Fridman, et al., 1992 *Int. J. Cancer* "Malignant Transformation of NIH-3T3 Cells After Subcutaneous co-Injection With a Reconstituted Basement Membrane (Matrigel)," 51(5), 740-44.
Friedmann, 1989, Progress toward human gene therapy, Science, 244(4910):1275-1281.
Fukuda, K. (2001). "Development of regenerative cardiomyocytes from mesenchymal stem cells for cardiovascular tissue engineering" Artif Organs 25(3): 187-93.
Fülöp, Csaba et al., "Expression of Alternatively Spliced Epidermal Growth Factor-like Domains in Aggrecans of Different Species," *The Journal of Biological Chemistry,* 1993, 268:17377-83.
Fulton et al., "Fat Grafting" *Fundamentals of Cosmetic Surgery.* 19(3):523-530 (Jul. 2001).
Ganey et al. "A potential role for cell-based therapeutics in the treatment of intervertebral disc herniation." Eur Spine J. 11(Suppl. 2):S206-214 (2002).
Ganey et al. "Intervertebral Disc Repair Using Adipose Tissue-Derived Stem and Regenerative Cells." 34(21):2297-2304 (2009).
Garcia-Olmo et al., "Autologous Stem Cell Transplantation for Treatment of Rectovaginal Fistula in Perianal Crohn's Disease: A New Cell-Based Therapy", Int. J Colorectal Dis (2003), 18:451-454.
Garrafa et al., 2006, Isolation and characterization of lymphatic microvascular endothelial cells from human tonsils, J Cell Physiol 207(1):107-113.
Gaustad, K.G., Boquest, A.C., Anderson, B.E., Gerdes, A.M., and Collas, P. (2004) "Differentiation of human adipose tissue stem cells using extracts of rat cardiomyocytes" Biochem. Biophys. Res Commun. 314, 420-427.
Geiselhart, A., Neu, S., Buchholz, F., Lang, P., Niethammer, D., and Handgretinger, R. (1996) "Postive selection of CD56+ lymphocytes by magnetic cell sorting" Nat Immun. 15, 227-233.
Gelse et al., Feb. 2003, Articular cartilage repair by gene therapy using growth factor-producing mesenchymal cells, Arthritis Rheum. 48:430-441.
Gimble et al. "Adipose-Derived Adult Stem Cells: Isolation, Characterization, and Differentiation Potential." Cytotherapy. 5(5):362-369 (2003).
Gimble, Jeffery M. et al., "Adipose tissue-derived therapeutics," *Expert Opin. Biol.,* 2003, 3(5)705-713.
Glowacki, J., "Influence of Age on Human Marrow," *Calcified Tissue International,* 1995, 56(Supp. 1):S50-1.
Goldman et al., 2005, Overexpression of VEGF-C causes transient lymphatic hyperplasia but not increased lymphangiogenesis in regenerating skin, Circ. Res. 96(11):1193-1199.
Greenberg, A.W. and Hammer, D.A. (2001) "Cell separation mediated by differential rolling adhesion" Biotechnol Bioeng 73 111-24.
Grigoradis A., et al., 1988 *J. Cell Biol.* "Differentiation of Muscle, Fat, Cartilage, and Bone from Progenitor Cells Present in a Bone-derived Clonal Cell Population: Effect of Dexamethasone," 106: 2139-2151.
Grigoriadis, Agamemnon E. et al., "Analysis of chondroprogenitor frequency and cartilage differentiation in a novel family of clonal chondrogenic rat cell lines," *Differentiation,* 1996, 60:299-307.
Groutz, A., J.G. Blavias et al (2000) "Outcome results of transurethral collagen injection for female stress incontinence: assessment by urinary incontinence score" J Urol 164(6): Sep. 2006.
Guerrerosantos, J., A. Gonzalez-Mendoza, et al. (1996). "Long-term survival of free fat grafts in muscle: an experimental study in rats." Aesthetic Plast Surg 20(5): 403-8.
Guerriero, V and JR Florini 1980 *Endocrinology* "Dexamethasone Effects on Myoblast Proliferation and differentiation," 106:1198-1202.
Haab, F., P.E. Zimmern et al (1997) Urinary stress incontinence due to intrinsic sphincteric deficiency: experience with fat and collagen periurethral injections: J Urol 157(4): 1283-6.
Hagege, A.A., Carrion, C., Menasche, P., Vilquin, J.T., Duboc, D., Marolleau, J.P., Desnos, M., and Bruneval, P. (2003) "Viability and differentiation of autologous skeletal myoblast grafts in ischaemic cardiomyopathy" Lancet 361, 491-2.
Hak et al., "Toxic effects of DMSO on cultured beating heart cells at temperatures above zero," Cryobiology, 1973, 10:244-250.
Hall, BK 1981 "Intracellular and extracellular control of differentiation of cartilage and bone," Histochem. J. 13:599-614.
Hamano et al. The induction of angiogenesis by the implantation of autologous bone marrow cells: A novel and simple therapeutic method. Surgery. 130(1):44-54 (2001).
Hamel, M., T. Shaarawy et al (2001) "Deep sclerectomy with collagen implant in patients with glaucoma and high myopia" J Cataract Refract Surg 27(9): 1410-7.
Hardingham, Tim et al., "Studies on the Synthesis, Secretion and Assembly of Proteoglycan Aggregates by Chondrocytes," *Matrices and Cell Differentiation,* 1984, 151:17-29.
Harvey et al., 2005, Lymphatic Vascular Defects Promoted by Prox1 Haploinsufficiency Cause Adult-Onset Obesity, Nature Genetics 37[10]:1072-1081.
Hauner et al. "Cultures of Human Adipose Precursor Cells." Methods in Molecular Biology. 155(1):239-247 (2001).
Hauner H. et al., "Glucocorticoids and Insulin Promote the Differentiation of Human Adipocyte Precursor Cells into Fat Cells," *Journal of Clinical Endocrinology and Metabolism,* 64:832-5, 1987.
Hauner, et al., "Endothelin-1 Inhibits the Adipose Differentiation of Cultured Human Adipocyte Precursor Cells," *Metabolism* 1994 43(2) pp. 227-232.
Hauner, Hans et al., "Promoting Effect of Glucocorticoids on the Differentiation of Human Adipocyte Precursor Cells Cultured in a Chemically Defined Medium," *Journal of Clinical Investigation,* 84:1663-70, 1989.
Hausman et al., 2001, The biology of white adipocyte proliferation, Obesity Reviews, 2(4):239-254.
Hausman et al., 2004, Adipose tissue angiogenesis, Journal of Animal Science 82:925-934.
Hausman, et al., "The Influence of Extracellular Matrix Substrata on Preadipocyte Development in Serum-Free Cultures of Stromal-Vascular Cells," *J. Anim.Sci.* 1996 74(9), 2117-2128.
Haynesworth, S. E. et al., "Cell Surface Antigen on Human Marrow-Derived Mesenchymal Cells are Detected by Monoclonal Antibodies," *Bone,* 1992, 13:69-80.
Hemmrich,K. et al. "Implantation of preadipocyte-loaded hyaluronic acid-based scaffolds into nude mice to evaluate potential for soft tissue engineering." *Biomaterials* 26, 7025-7037 (2005).
Hemstreet, G.P. 3, Enoch, P.G., and Pretlow, T.G. 2 (1980) "Tissue disaggregation of human renal cell carcinoma with further isopyknic and isokinetic gradient purification" Cancer Res 40, 1043-9.

(56) References Cited

OTHER PUBLICATIONS

Herman, Ira M. and Patricia D'Amore, "Microvascular Pericytes Contain Muscle and Nonmuscle Actins," *J. Cell Biol.* 1985 101:43-52.
Hess, D.C. et al. Hematopoietic Origin of Microglial and Perivascular Cells in Brain, Experimental Neurology, Apr. 2004, vol. 186, pp. 134-144.
Hewitson et al., 2006, Histochemical localization of cell proliferation using in situ hybridization for histone mRNA, Methods Mol. Biol. 326:219-26.
Hong et al. "Adipose tissue engineering by human adipose-derived stromal cells." *Cells Tissues Organs* 183, 133-140 (2006).
Horwitz et al., 2005, Clarification of the nomenclature for MSC: The International Society for Cellular Therapy position statement, 7(5):393-395.
Horwitz, E. M., D.J. Prockop, et al. (1999). "Transplantability and therapeutic effects of bone marrow-derived mesenchymal cells in children with osteogenesis imperfecta." Nat Med 5(3): 309-13.
Horwitz, E.M., Prockop, D.J., Gordon, P.L., Koo, W. W., Fitzpatrick, L.A., Neel, M.D., McCarville, M.E., Orchard, P.J., Pyeritz, R.E., and Brenner, M.K. (2001) "Clinical responses to bone marrow transplantation in children with severe osteogenesis imperfecta." Blood 97(5), 1227-31.
Hsiung, M. W., P. Woo et al (2000) "Fat augmentation for glottic insufficiency" Laryngoscope 110(6): 1026-33.
Huang, J.I., S.R. Beanes, et al. (2002) "Rat extramedullary adipose tissue as a source of osteochondrogenic progenitor cells" Plast Reconstr Surg 109(3): 1033-41; discussion 1042-3.
Huard et al, 2002, Muscle-derived cell-mediated ex vivo gene therapy for urological dysfunction, Gene Therapy, 9:1617-1626.
Huibregtse, Barbara, et al., 1998, "Effect of Age and Sampling Site on the Chondro-Osteogenic Potential of Rabbit Marrow-derived Mesenchymal Progenitor Cells," *Journal of Orthopaedic Research.* 18:18-24.
Hui-Ling et al., "Increased expression of G in mouse embryo stem cells promotes terminal differentiation to adipocytes," *American Physiological Society* 1993 265(6), C1729-C1735.
Hur et al. Akt Is a Key Modulator of Endothelial Progenitor Cell Trafficking in Ischemic Muscle. Stem Cells. 25:1769-1778 (2007).
Huss, Ralf, "Isolation of Primary and Immortalized CD34-Hematopoietic and Mesenchymal Stem Cells from Various Sources," *Stem Cells,* 2000, 18:1-9.
Hutley, L.J., A.C. Herington, et al. (2001) "Human adipose tissue endothelial cells promote preadipocyte proliferation" Am J. Physiol Endocrinol Metab 281(5): E1037-44.
Ito et al., 2001, A new continuous-flow cell separation method based on cell density: principle, apparatus, and preliminary application to separation of human buffy coat, Journal of Clinical Apheresis, 16(4):186-191.
Iwasaki, Motoki et al., "Regulation of Proliferation and Osteochondrogenic Differentiation of Periosteum-Derived Cells by Transforming Growth Factor-b and Basic Fibroblast Growth Factor," *Journal of Bone and Joint Surgery,* 1995, 77A:543-54.
Jackson et al. Regeneration of ischemic cardiac muscle and vascular endothelium by adult stem cells. Journal Clinical Investigation. 107(11): 1395-1402 (2001).
Jaiswal, et al., 1997 "Osteogenic Differentiation of Purified, Culture-Expanded Human Mesenchymal Stem Cells In Vitro," J. Cell Biochem. 64:295-312.
Jaiswal, R.K., Jaiswal, J., Bruder, S.P., Mbalaviele, G., Marshak, D.R., and Pittenger, M.F. (2000) "Adult human mesenchymal stem cell differentiation to the osteogenic or adipogenic lineage is regulated by mitogen-activated protein kinase" J Biol Chem 275, 9645-52.
Ji, 2006, Lymphatic Endothelial Cells, Lymphangiogenesis, and Extracellular Matrix, Lymphat. Res. Biol. 4(2):83-100.
Jiang, Y., Jahagirdar, B.N., Reinhardt, R.L., Schwartz, R.E., Keene, C.D., Ortiz-Gonzalez, X.R., Reyes, M. Lenvik, T., Lund, T., Blackstad, M., Du, J., Aldrich, S., Lisberg, A., Low, W.C., Largaespada, D.A., and Verfaillie, C.M. (2002a) "Pluripotency of mesenchymal stem cells derived from adult marrow" Nature 418, 41-9.
Jiang, Y., Vaessen, B., Lenvik, T., Blackstad, M., Reyes, M., and Verfaillie, C.M. (2002b) "Multipotent progenitor cells can be isolated from postnatal murine bone marrow, muscle, and brain" Exp Hematol 30, 896-904.
Johnson, P. R. et al., "Uncontrolled adipocyte proliferation is not the primary lesion in the genetically-obese obese Zucker rat," *International Journal of Obesity,* 5:563-70, 1981.
Johnstone B., et al., 1998 "In Vitro Chondrogenesis of Bone Marrow-Derived Mesenchymal Progenitor Cells," Exp. Cell Res. 238: 265-272.
Joyner, C.J., Triffitt, J., Puddle, B., and Athanasou, N.A. (1999) "Development of a monoclonal antibody to the aP2 protein to identify adipocyte precursors in tumours of adipose differentiation" Pathol. Res Pract. 195, 461-466.
Jurgens et al. "Effect of tissue-harvesting site on yield of stem cells derived from adipose tissue: implications for cell-based therapies." Cell Tiss. Res. 332:415-426 (2008).
Kale et al. "Bone marrow stem cells contribute to repair of the ischemically injured renal tubule" J. Clinical Investigation, vol. 112, No. 1 42-49 (Jul. 2003).
Kamer, F.M. and M.M. Churukian (1984) "Clinical use of injectable collagen. A three-year retrospective review" Arch Otolaryngol 110(2): 93-8.
Kamihata et al. "Improvement of collateral perfusion and regional function by implantation of peripheral blood mononuclear cells into ischemic hibernating myocardium." Thromb Vascular Biology. 22:1804-1810 (2002).
Kang et al. "Improvement of neurological deficits by intracerebral transplantation of human adipose tissue-derived stromal cells after cerebral ischemia in rats." Experimental Neurology. 183(2):355-366 (2003).
Kang et al. "Interactions between human adipose stromal cells and mouse neural stem cells in vitro." Developmental Brain Research. 145(1): 141-149 (2003).
Kania, et al., 1990 "The *Drosophila* segmentation gene runt encodes a novel nuclear regulatory protein that is also expressed in the developing nervous system," Genes Dev. 4:1701-1713.
Karkkainen et al., 2002, Lymphatic endothelial regulation, lymphoedema, and lymph node metastasis, Semin Cell Dev Biol 13(1):9-18.
Karlsson et al., "Long-term storage of tissues by cryopreservation: critical issues," Biomaterials 1996, 17(3):243-256.
Katz et al. 2005, Cell surface and transcriptional characterization of human adipose-derived adherent stromal (hADAS) cells, Stem Cells 23(3):412-23.
Katz, A.J., Hedrick, M.H., Llull, R., and Futrell, J.W. (2001) "A novel device for the simple and efficient refinement of liposuctioned tissue" Plast Reconstr Surg 107, No. 2, 595-597.
Katz, Adam J. et al., "Emerging Approaches to the Tissue Engineering of Fat," *Clinics in Plastic Surgery,* 1999, 26:587-603.
Katz, B.E., Bruck, M.C. and Coleman, W. P. 3 (2001b) "The benefits of powered liposuction versus traditional liposuction: a paired comparison analysis" Dermatol Surg 27, 863-7.
Kaushal, S., Amiel, G.E., Guleserian, K.J., Shapira, O.M., Perry, T., Sutherland, F.W., Rabkin, E., Moran, A.M. Schoen, F.J., Atala, A., Soker, S., Bischoff, J., and Mayer, J.E., Jr. (2001) "Functional small-diameter neovessels cretaed using endothelial progenitor cells expanded ex vivo" Nat Med 7, 1035-40.
Kawamoto, A., Tkebuchava, T., Yamaguchi, J., Nishimura, H., Yoon, Y.S., Milliken, C., Uchida, S., Masuo, O., Iwaguro, H., Ma, H., Hanley, A., Silver, M., Kearney, M., Lorsordo, D.W., Isner, J.M. and Asara, T. (2003) "Intramyocardial transplantation of autologous endothelial progenitor cells for therapeutic neovascularization of myocardial ischerriia" Circulation 107, 461-8.
Kehlen, A. et al., 2000 *J. Cell Biochem.* "Increased Lymphocytic Aminopeptidase N/CD13 Promoter ctivity After Cell-Cells Contact," 80:115-123.
Kerjaschki et al., 2006, Lymphatic endothelial progenitor cells contribute to de novo lymphangiogenesis in human renal transplants, Nature Medicine 12(2):230-4.

(56) References Cited

OTHER PUBLICATIONS

Kern, P.A., A. Knedler, et al. (1983) Isolation and culture of microvascular endolthellium from human adipose tissue: J Clin Invest 71(6): 1822-9.
Killinger, D. W. et al., "Influence of Adipose Tissue Distribution on the Biological Activity of Androgens," *Annals New York Academy of Sciences*, 595:199-211, 1990.
Killinger, Donald W. et at., "The Relationship Between Aromatase Activity and Body Fat Distribution," *Steroids*, 50:61-72, 1987.
Kim et al., 2002, Ex vivo gene delivery of IL-1Ra and soluble TNF receptor confers a distal synergistic therapeutic effect in antigen-induced arthritis, Mol. Ther. 6:591-600.
Kim, et al. "Wound healing effect of adipose-derived stem cells: A critical role of secretory factors on human dermal fibroblasts." Journal of Dermatological Science. 48(1): 15-24 (2007).
Kimura et al. "Adipose tissue engineering based on human preadipocytes combined with gelatin microspheres containing basic fibroblast growth factor." *Biomaterials* 24, 2513-2521 (2003).
Kirsch, Thorsten and Klaus von der Mark, "Remodelling of collagen types I, II and X and calcification of fetal cartilage," *Bone and Mineral,* 1992, 18:107-17.
Klar et al., 2005, RAR-related orphan receiptor a isoform 1 (RORa1) is disrupted by a balanced translocation t(4;15)(q22.3;121.3) associated with severe obesity, Eur. J. Hum. Genet. 13(8):928-934.
Klein et al., 2006, Adipose tissue as source and target for novel therapies, Trends Endocrin. Metab., 17(1):26-32.
Klein, A.W. (2001) "Skin filling. Collagen and other injectables of the skin" Dermatol Clin 19(3): 491-508, ix.
Kong et al., 2005, Effect of cardiac lymph flow obstruction on cardiac collagen synthesis and interstitial fibrosis, Physiol Res. 55:253-258.
Kosher, RA, et al., 1986 *J. Cell Biol.* "Collagen Gene Expression During Limb Cartilage Differentiation," 102:1151-1156.
Kosher, Robert A. and Michael Solursh, "Widespread Distribution of Type II Collagen during Embryonic Chick Development," *Developmental Biology,* 1989, 131:558-66.
Koufman, J.A. (1991) "Lipoinjection for vocal cord paralysis" Laryngoscope 101(12 Pt 1): 1385.
Kriehuber et al., 2001, Isolation and characterization of dermal lymphatic and blood endothelial cells reveal stable and functionally specialized cell lineages, J Exp Med 194(6):797-808.
Kuri-Harcuch, W. et al., 1984, *Differentiation* "Extracellular matrix production by mouse 3T3-F442A cells during adipose differentiation in culture," 28.
Lafontan, M. et al., "Réflexions sur une nouvelle approche de chirurgie plastique réparatrice: la réimplantation de fragments de tissu adipeux prélevés par liposuccion," *Ann. Chur. Plast. Esthet.*, 34:77-81, 1989.
Lam, Anson and Ronald Moy, "The Potential for Fat Transplantation," *J. Dermatol. Surg. Oncol.*, 18:432-4, 1992.
Lambert et al., 1993, Local drug delivery catheters: functional comparison of porous and microporous designs, Coron. Artery Dis. 4:469-475.
Lamouille, S., Mallet, C., Feige, J.J., and Bailly, S. (2002) "Activin receptor-like kinase 1 is implicated in the maturation phase of angiogenesis" Blood 100, 4495-4501.
Lanier, L.L. et al, 1991 J. lmmunol. "Molecular and Functional Analysis of Human Natural Killer Cell-Associated Neural Cells Adhesion Molecule (N-Cam/CD56),"146:4421-4426.
Lasch, J., Kullertz, G., and Opalka, J.R. (2000) "Separation of erythrocytes into age-related fractions by density or size? Counterflow centrifugation" Clin Chem Lab Med 38, 629-632.
Latoni, J.D., D.M. Marshall et al (2000 "Overgrowth of fat autotransplanted for correction of localized steroid-induced atrophy" Plast Reconstr Surg 106(7): 1566-9.
Lawson-Smith, M.J. and McGeachie, J.K. 1998 *J. Anat.* "The identification of myogenic cells in skeletal muscle, with emphasis on the use of tritiated thymidine autoradiography and desmin antibodies," 192:161-171.
Lazarus, Hillard M. et al., "Human Bone Marrow-Derived Mesenchymal (Stromal) Progenitor Cells (MPCs) Cannot Be Recovered from Peripheral Blood Progenitor Cell Collections," *Journal of Hematotherapy*, 1997, 6:447-55.
Leboy, et al., 1991 *J. Cell Physiol.* "Dexamethasone Induction of Osteoblast mRNAs in Rat Marrow Stromal Cell Cultures," 146:370-378.
Leboy, Phoebe S. et al., "Ascorbic Acid Induces Alkaline Phosphatase, Type X Collagen, and Calcium Deposition in Cultured Chick Chondrocytes," *The Journal of Biological Chemistry,* 1989, 264:17281-6.
Lecoeur, L. and J. P. Ouhayoun, "In vitro induction of osteogenic differentiation from non-osteogenic mesenchymal cells," *Biomatenals,* 18:989-93, 1997.
Lee et al., "Adhesion Molecules in Skeletogenesis: I. Transient Expression of Neural Cell Adhesion Molecules (NCAM) in Osteoblasts During Endochondral and Intramembranous Ossification," *Journal of Bone and Mineral Research,* 1992, 7:1435-46.
Lee et al., Jan. 2006, Human adipose-derived stem cells display myogenic potential and perturbed function in hypoxic conditions, Biochemical and Biophysical Research Communications, 341:882-888.
Lee, J. H., Z. Ilic, et al. (1996) "Cell kinetics of repair after allyl alcohol-induced liver necrosis in mice" Int J Exp Pathol 77(2): 63-72.
Lee, P.E., R.C. Knug, et al. (2001) "Periurethral autologous fat injection as treatment for female stress urinary incontinence: a randomized double-blind controlled trial" J Urol 165(1): 153-8.
Lehner, M. and Holter, W. (2002) "Endotoxin-free purification of monocytes for dendritic cell generation via discontinuous density gradient centrifugation based on diluted Ficoll-Paque Plus" Int Arch Allergy Immunol 128, 73-76.
Lendahl, et al., 1990 *Cell* "CNS Stem Cells Express a New Class of Intermediate Filament Protein," 60:585-595.
Lennon, D.P., Haynesworth, S.E., Young, R.G., Dennis, J.E., and Caplan, A.I. (1995) "A chemically defined medium supports in vitor proliferation and maintains the osteochondral potential of rat marrow-derived mesenchymal stem cells" Exp Cell Res 219, 211-22.
Lennon, Donald P. et al., "Human and Animal Mesenchymal Progenitor Cells from Bone Marrow: Identification of Serum for Optimal Selection and Proliferation," *In Vitro Cell. Dev. Biol.—Animal,* 1996, 32:602-11.
Lenoir, N. 2000 *Science* "Europe Confronts the Embryonic Stem Cell Research Challenge," 287:1425-1427.
Leo et al., 2004, In vivo bioluminescent imaging of virus-mediated gene transfer and transduced cell transplantation in the interverebral disc, Spine, 29(8):838-844.
Lev, Robert and S. S. Spicer, "Specific Staining of Sulphate Groups with Alcian Blue at Low pH," *J. Histochem. Cytochem.,* 1964, 12:309-10.
Lin, et al. "Hematopoietic Stem Cells Contribute to the Regeneration of Renal Tubules After Renal Ischmia-Reperfusion Injury in Mice." Journal of the American Society of Nephrology. 14: 1188-1199 (2003).
Lincoff et al., 1994, Local drug delivery for the prevention of restenosis. Fact, fancy, and future, Circulation, 90:2070-2084.
Linsenmayer, Thomas et al., 1998, "Type X Collagen: A Hypertrophic Cartilage-Specific Molecule," *Pathol. Immunopathol.* 7:14-19.
Liu, S.H., R.S. Yang et al (1995) "Collagen in tendon, ligament and bone healing. A current review" Clin Orthop (318): 265-78.
Loncar, D., "Ultrastructural analysis of differentiation of rat endoderm in vitro. Adipose vascular-stromal cells induce endoderm differentiation, which in turn induces differentiation of the vascular-stromal cells into chondrocytes," *J. Submicrosc. Cytol. Pathol.,* 24:509-19, 1992.
Long, Michael W. et al., "Age-Related Phenotypic Alterations in Populations of Purified Human Bone Precursor Cells," *The Journals of Gerontology,* 1999, 54A:B54-62.
Lucas, P. A. et al., "Isolation of Putative Mesenchymal Stem Cells from Rat Embryonic and Adult Skeletal Muscle," *In Vitro Cell Dev. Biol.,* 1992, 28:154A.
Lucas, Paul A. et al., "Mesenchymal Stem Cells From Granulation Tissue," *J. Cell Biochem,* 1993 17E:122, R212.

(56) References Cited

OTHER PUBLICATIONS

Lumelsky, N., et al. 2001 *Science* "Differentiation of Embryonic Stem Cells to Insulin-Secreting Structures Similar to Pancreatic Islets," 292:1389-1394.
Lund et al. "Granulocyte colony-stimulating factor mobilized CFU-F can be found in the peripheral blood but have limited expansion potential." Haematologica. 93(6):908-912 (2008).
Luskey, B.D., Lim, B., Apperley, J.F., Orkin, S.H., and Williams, D.A. (1990) "Gene transfer into murine hematopoietic stem cells and bone marrow stromal cells" Ann NY Acad Sci 612, 398-406.
Luttun, A., Tjwa, M., Moons, L., Wu, Y., Angelillo-Scherrer, A., Liao, F., Nagy, J.A., Hooper, A., Priller, J., De Klerck, B., Compernolle, F., Daci, E., Bohlen, P., Dewerchin, M., Herbert, J.M., Fava, R., Matthys, P., Carmeliet, G., Collen, D., Dvorak, H.F., Hicklin, D.J., and Carmeliet, P. (2002)."Revascularization of ischemic tissues by PIGF treatment, and inhibition of tumor angiogenesis, arthritis and atherosclerosis by anti-Fltl" Nat Med 8, 831-40.
Lynch, et al., 1995, *Exp. Cell Res.* "The Influence of Type I Collagen on the Development and Maintenance of the Osteoblast Phenotype in Primary and Passaged Rat Calvarial Osteoblasts: Modification of Expression of Genes Supporting Cell Growth, Adhesion, and Extracelluar Matrix Mineralization," 216:35-45.
MacDougald, Ormond A. and M. Daniel Lane, "Transcriptional Regulation of Gene Expression During Adipocyte Differentiation," *Annu. Rev. Biochem.*, 1995, 64:345-73.
Mainwaring, G. and Rowley, A.F. (1985) "Separation of leucocytes in the dogfish (Scyliorhinus canicula) using density gradient centrifugation and differential adhesion to glass coverslips" Cell Tissue Res 241, 283-90.
Majeska, Robert J. and Gideon A. Rodan, "The Effect of 1,25(OH)2D3 on Alkaline Phosphates in Osteoblastic Osteosarcoma Cells," *J. Biol. Chem.* 1982 257:3362-3365.
Majumdar, M.K., Thiede, M.A., Mosca, J.D., Moorman, M., and Gerson, S.L. (1998) "Phenotypic and functional comparison of cultures of marrow-derived mesenchymal stem cells (MSCs) and stromal cells" J Cell Physiol 176, 57-66.
Malaval, et al., 1994 *J. Cell. Physiol.* "Cellular Expression of Bone-Related Proteins During In Vitro Ostegenesis in Rat Bone Marrow Stromal Cell Culture," 158:555-572.
Manduca, et al., 1992 *Eur. J. Cell Biol.* "Chondrogenic differentiation in chick embryo osteoblast cultures," 57:193-201.
Manetti et al. (2000) "Fibroblast growth factors and their inhibitors" Curr. Pharm. Des 6, 1897-1924.
Marchlinski, F.E., Falcone, R., Iozzo, R.V., Reichek, N., Vassallo, J.A., and Eysmann, S.B. (1987) "Experimental myocardial cryoinjury: local electromechanical changes, arrhythmogenicity, and methods for determining depth of injury" Pacing Clin Electrophysiol 10, 886-901.
Marko, et al., "Isolation of a Preadipocyte Cell Line from Rat Bone Marrow and Differentiation to Adipocytes," *Endocrinology* 1995 136(10), 4582-4588.
Martin, et al., 1999 *Exp. Cell Res.* "Mammalian Chondrocytes Expanded in the Presence of Fibroblast Growth Factor 2 Maintain the Ability to Differentiate and Regenerate Three-Dimensional Cartilaginous Tissue," 253:681-688.
Martinez-Estrada et al. "Human adipose tissue as a source of Flk-1 <+> cells: new method of differentiation and expansion." Cardiovascular Research. 65(2):328-333 (2005).
Maruyama et al., Apr. 2007, Decreased Macrophage Number and Activation Lead to Reduced Lymphatic Vessel Formation and Contribute to Impaired Diabetic Wound Healing, Am J Pathol. 170(4):1178-1191.
Massi et al., 2006, Tumour lymphangiogenesis is a possible predictor of sentinel lymph node status in cutaneous melanoma: a case-control study, J Clin Pathol, 59(2):166-173.
Masuda et al. "Novel strategy for soft tissue augmentation based on transplantation of fragmented omentum and preadipocytes." *Tissue Eng* 10, 1672-1683 (2004).
Masuda,et al. "Photocured, styrenated gelatin-based microspheres for de novo adipogenesis through corelease of basic fibroblast growth factor, insulin, and insulin-like growth factor I." *Tissue Eng* 10, 523-535 (2004).
Mazur et al., 1994, Coronary restenosis and gene therapy, Texas Heart Institute Journal, 21:104-111.
Megeney, et al., 1996 *Genes Dev.* "MyoD is required for myogenic stem cell function in adult skeletal muscle," 10:1173-1183.
Mehlhorn et al., 2001, Myocardial Fluid Balance, Eur. J. Cardio-thoracic Surg. 20:1220-1230.
Mezey, et al. "Comment on 'Failure of Bone Marrow Cells to Transdifferentiate into Neural Cells in Vivo.'" Science. 299:1184b (2003).
Miller, 1992, Human gene therapy comes of age, Nature, 357:455-460.
Miller, J.J. and J.C. Poop (2002) "Fat hypertrophy after autologous fat transfer" Opthal Plast Reconstr Surg 18(3): 228-31.
Mills, J.D., Fischer, D., and Villaneuva, F.S. (2000) "Coronary collateral development during chronic ischemia: serial assessment using harmonic myocardial contrast echocardiography" J Am Coll Cardiol 36(2):618-24.
Miranville et al. "Human adipose tissue-derived stem cells improve postnatal neovascularization." International Journal of Obesity. 28(Suppl 1):S100 (May 2004).
Miranville et al. "Human adipose tissue-derived stem cells improve blood flow in the ischemic mouse hind-limb" Circulation, vol. 108, No. 17, Supp. IV, 164 (Oct. 2003).
Miranville, et al. "Improvement of postnatal neovascularization by human adipose tissue-derived stem cells." Circulation, American Heart Association. 110(3):349-355 (2004).
Mizuno, H., P.A. Zuk, et al. (2002) "Myogenic differentiation by human processed lipoaspirate cells" Plast Reconstr Surg 109(1): 199-209; discussion 210-1.
Mohr, M., Dalmis, F., Hilgenfeld, E., Oelmann, E., Zuhisdorf, M., Kratz-Alberts, K., Nolte, A., Schmitmann, C., Onaldi-Mohr, D., Cassens, U., Serve, H., Sibrowski, W., Kienast, J., and Berdel, W.E. (2001) "Simultaneous immunomagnetic CD34+ cell selection and B-cell depletion in peripheral blood progenitor cell samples of patients suffering from B-cell non-Hodgkin's lymphoma" Clin Cancer Res 7, 51-57.
Moitra et al., 1998, Life without white fat: a transgenic mouse, Genes Dev. 12(20):3168-3181.
Molkentin and Olson 1996 *Curr. Opin. Genet. Dev.* "Defining the regulatory networks for muscle development," 6:445-453.
Monteiro, P., Antunes, A., Goncalves, L.M., and Providencia, L.A. (2003) "Long-term clincal impact of coronary-collateral vessels after acute myocardial infarction" Rev. Port. Cardiol 22, 1051-1061.
Morizono, K., De Ugarte, D.A., Zhu, M., Zuk, P., Elbarbary, A., Ashjian, P., Benhaim, P. Chen, I.S., and Hedrick, M.H. (2003) "Multilineage cells from adipose tissue as gene delivery vehicles" Hum Gene Ther 14, 59-66.
Mosca, J.D. Hedricks, J.K. Buyaner, D., Davis-Sproul, J., Chuang, L.C., Majumdar, M.K., Chopra, R., Barry, F., Murphy, M., Thiede, M.A. Junker, U., Rigg, R.J., Forestell, S.P., Bohnlien, E., Storb, R., and Sandmaier, B.M. (2000) "Mesenchymal stem cells as vehicles for gene delivery" Clin Orthop 71-90.
Mullen, Richard J. et al., "NeuN, a neuronal specific nuclear protein in vertebrates," *Development*, 1992, 116:201-11.
Muller et al. "Selection of ventricular-like cardiomyocytes from ES cells in vitro." The FASEB Journal. 14:2540-2548 (2000).
Mullins, R.J., C. Richards et al. (1996) "allergic reactions to oral, surgical and topical bovine collagen. Anaphylactic risk for surgeons" Aust N Z J Ophthalmol 24(3): 257-60.
Mundlos, et al., 1997 *Cell* "Mutations Involving the Transcription Factor CBFA12 Cause Cleidocranial Dysplasia," 89:773-779.
Muramatsu, T., Nakamura, A., and Park, H.M. (1998) "In vivo electroportion: a powerful and convenient means of nonviral gene transfer to tissues of living animals (Review)" Int J Mol Med 1, 55-62.
Murayama, T., O.M. Tepper, et al. (2002) "Determination of bone marrow-derived endothelial progenitor cells significance in angiogenic growth factor-induced neovascularization in vivo" Exp Hematol 30(8): 967-72.

(56) References Cited

OTHER PUBLICATIONS

Murry CE et al. 2004. Hematopoietic stem cells do not transdifferentiate into cardiac myocytes in myocardial infarcts. Nature 428: 664-668.
Murry, C.E., Wiseman, R.W., Schwartz, S.M., and Hauschka, S.D. (1996) Skeletal myoblast transplantation for repair of myocardial necrosis: J Clin Invest 98, 2512-23.
Muschler, G.F., Nitto, H., Boehm, C.A., and Easley, K.A. (2001) "Age-and gender-related changes in the cellularity of human bone marrow and the prevalence of osteoblastic progenitors" J Orthop Res 19(1), 117-25.
Muskhelishvili et al., 2003, Evaluation of cell proliferation in rat tissues with BrdU, PCNA, Ki-67(MIB-5) immunohistochemistry and in situ hybridization for histone mRNA, J. Histochem. & Cytochem. 51(12):1681-1688.
Myllyharju, J. (2000) "Recombinant collagen trimers from insect cells and yeast" Methods Mol Biol 139: 39-48.
Nagle, R. B. et al., "Factor VII-Associated Antigen in Human Lymphatic Endothelium," *Lymphology,* 1987, 20:20-4.
Nagy, J.A., Dvorak, A.M., and Dvorak, H.F. (2003) VEGF-A (164/165) and PIGF: roles in angiogenesis and arteriogenesis: Trends Cardiovasc Med 13, 169-175.
Nakahara, H. et al., "Bone and Cartilage Formation in Diffusion Chambers by Subcultured Cells Derived from the Periosteum," *Bone,* 1990, 11:181-8.
Nakajima, I. et al., 1998, "Adipose tissue extracellar matrix: newly organized by adipocytes during differentiation," *Differentiation* 63:193-200.
Nakano, Hirotaka et al., "RT-PCR Suggests Human Skeletal Muscle Origin of Alveolar Soft-Part Sarcoma," *Oncology,* 2000, 58:319-23.
Nathan, Suresh et al. "Cell-Based Therapy in the Repair of Osteochrondral Defects: A Novel Use for Adipose Tissue", Tissue Engineering, vol. 9, No. 4, 2003.
Nehls, A. and D Drenckhahn 1991 *J. Cell Biol.* "Heterogeneity of Microvascular Pericytes for Smooth Muscle Type Alpha-Actin," 113:147-154.
Nerem, R.M. and Ensely, A.E. (2004) "The tissue engineering of blood vessels and the heart" Am J Transplant 4 Supp 6, 36-42.
Ng et al., Nov. 2004, Interstitial flow differentially stimulates blood and lymphatic endothelial cell morphogenesis in vitro, Microvasc Res. 68(3):258-64.
Nguyen, A., K.A. Pasyk et al. (1990) "Comparative study of survival of autologous adipose tissue taken and transplanted by different techniques" Plast Reconstr Surg 85(3): 378-86; discussion 387-9.
Nishimori, M. Yamada, Y., Hoshi, K., Akiyama, Y., Hosi, Y., Morishima, Y., Tsuchida, M., Fukuhara, S., and Kodera,Y. (2002) "Health-related quality of life of unrelated bone marrow donors in Japan" Blood 99(6), 1995-2001.
Novakofski, Jan E., "Primary Cell Culture of Adipose Tissue," *Biology of the Adipocyte: Research Approaches*, Van Nostrand Reinhold Company, NY, 1987 160-97.
O'Driscoll, Shawn W., "Current Concepts Review: The Healing and Regeneration of Articular Cartilage," *Journal of Bone and Joint Surgery,* 1998, 80A:1795-812.
Odorico, J.S., Kaufman, D.S., and Thomson, J.A. (2001) "Multilineage differentiation from human embryonic stem cells lines" Stem Cells 19, 193-204.
Ogawa, 2006, The importance of adipose-derived stem cells and vascularized tissue regeneration in the field of tissue transplantation, Current Stem Cell Research & Therapy, 1:13-20.
Ohgushi, H. and Caplan, A.I. (1999) "Stem cell technology and bioceramics: from cell to gene engineering" J Biomed Mater Res 48, 913-27.
Olson, E. N. et al., "Know Your Neighbors: Three Phenotypes in Null Mutants of the Myogenic bHLH Gene MRF4," *Cell,* 1996, 85:1-4.
Ooi, K., M.P. Lacy et al (1991) "Salt-soluble collagen and elastin in the human aorta and pulmonary artery" Exp Mol Pathol 55(1): 25-9.
Kajstura et al. (2001) "Bone marrow cells regenerate infarcted myocardium" Nature 410(6829): 701-5.
Orlic, D., J. Kajstura, et al. (2001) "Transplanted adult bone marrow cells repair myocardial infarcts in mice" Ann N Y Acad Sci 938: 221-9, discussion 229-30.
Owen, TA, et al., 1990 *J. Cell Physiol.* "Progressive Development of the Rat Osteoblast Phenotype in Vitro: Reciprocal Relationships in Expression of Genes Associated with Osteoblast Proliferation and Differentiation During Formation of the Bone Extracellular Matrix," 143:420-430.
Pairault, Jacques and Howard Green, "A study of the adipose conversion of suspended 3T3 cells by using glycerophosphate dehydrogenase as differentiation marker," *Proc. Natl. Acad. Sci. USA*, 1979, 76:5138-42.
Pajvani et al., 2005, Fat apoptosis through targeted activation of caspase 8: a new mouse model of inducible and reversible lipoatrophy, Nature Medicine, 11(7):797-803.
Palma, P.C., C.L. Riccetto, et al. (1997) "Repeated lipoinjections for stress urinary incontinence" J Endourol 11(1): 67-70.
Park, S. R. et al., "Interconversion Potential of Clone Human Marrow Adipocytes In Vitro," *Bone,* 1999, 24:549-54.
Patrick et al. "Long-term implantation of preadipocyte-seeded PLGA scaffolds." Tissue Eng. 8(2):283-93 (2002).
Patrick et al. "Preadipocyte Seeded PLGA Scaffolds for Adipose Tissue Engineering." Tissue Eng. 5(2): 139-151 (1999).
Patrick, et al., 2000, Semin. Surg. Oncol. 19(3):302-11.
Paul S.R., et al., 1991 *Blood* "Stromal Cell-Associated Hematopoiesis: Immortalization and Characterization of Primate Bone Marrow-Derived Stromal Cell Line," 77: 1723-33.
Pavcnik et al., 2004, Second-generation percutaneous bioprosthetic valve: a short-term study in sheep, Eur. J. Endovasc. Surg. 40:1223-1227.
Pedersen, S. B. et al., "Identification of oestrogen receptors and oeostrogen receptor mRNA in human adipose tissue," *European Journal of Clinical Investigation*, 26:262-9, 1996.
Pera, M.F., Reubinoff, B., and Trounson, A. (2000) "Human embryonic stem cells" J Cell Sci 113 (Pt 1) 5-10.
Perbeck et al., Mar. 2006, Lymph Circulation in the Breast after Radiotherapy and Breast Conservation, Lymphology, 39(1):33-40.
Periasamy, Muthu et al., "Regulation of myosin heavy-chain gene expression during skeletal-muscle hypertrophy," *Biochem. J.* 1989 257:691-698.
Perin et al. "Transendocardial, autologous bone marrow cell transplantation for severe, chronic ischemic heart failure." Circulation. 107(18):2294-2302 (2003).
Pettengell et al. "Peripheral Blood Progenitor Cell Transportation in Lymphoma and Leukemia Using a Single Apheresis." Blood. 82:3770-3777 (1993).
Pettersson, Per et al., "Adipocyte Precursor Cells in Obese and Nonobese Humans," *Metabolism,* 34:808-12, 1985.
Pettersson, Per et al., "Cells in Human Adipose Tissue Developing into Adipocytes," *Acta Med Scand,* 1984, 215:447-51.
Pierelli, Luca et al., "CD34+/CD105+ cells are enriched in primitive circulating progenitors residing in the G0 phase of the cell cycle and contain all bone marrow and cord blood CD34+/CD38low/-precursors," *British Journal of Haematology,* 2000, 108:610-20.
Piersma et al. "Migration of fibroblastoid stromal cells in murine blood." Cell Tissue Kinet. 18:589-595 (1985).
Pipp, F., Heil, M., Issbrucker, K., Ziegelhoeffer, T., Martin, S., Van den, H.J., Weich, H., Fernandez, B., Golumb, G., Carmeliet, P., Schaper, W., and Clauss, M. (2003) "VEGFR-1-selective VEGF homologue PIGF is arteriogenic: evidence for a monocyte-mediated mechanism" Circ. Res 92, 378-385.
Pittenger, M.F., A.M. Mackay, et al. (1999) "Multilineage potential of adult human mesenchymal stem cells" Science 284(5411): 143-7.
Planat-Benard et al. "Spontaneous Cardiomyocyte Differentiation from Adipose Tissue Stroma Cells." Circulation Research. 94(2):223-229 (2004).
Planat-Bernard, et al. "Plasticity of Human Adipose Lineage Cells toward Endothelial Cells Physiological and Therapeutic Perspectives." Circulation, American Heart Association. 109(5):656-663 (2004).
Podgrabinska et al., Dec. 10, 2002, Molecular characterization of lymphatic endothelial cells, PNAS 99(25):16069-16074.

(56) References Cited

OTHER PUBLICATIONS

Poliard, a. et al., "Controlled Conversion of an Immortalized Mesodermal progenitor Cell Towards osteogenic, Chondrogenic, or Adipogenic Pathways," *J. Cell Biol.* 1995 130;1461-1472.
Ponce, 2001, 14. In vitro Matrigel Angiogenesis Assays, in Methods in Molecular Medicine, vol. 46: Angiogenesis Protocols, Edited by JC Murray, Humana Press, Totowa, NJ, pp. 205-209.
Price, Paul A. and Sharon A. Baukol, "1,25-Dihydroxyvitamin D3 Increases Synthesis of the Vitamin K-dependent Bone Protein by Osteosarcoma Cells," *The Journal of Biological Chemistry,* 1980, 255:11660-3.
Price, Paul A. et al., "Matrix GLA Protein, A New γ-Carboxyglutamic Acid-Containing Protein Which is Associated With the Organic Matrix of Bone," *Biochem. Biophys. Res. Commun.,* 1983 117:765-771.
Price, Paul A., "GLA-Containing Proteins of Bone," *Connective Tissue Research,* 1989, 21:51-60.
Prince, H.M., Bashford, J., Wall, D., Rischin, D., Parker, N., Toner, G.C., Seymour, J.F., Blakey, D., Haylock, D. Simmons, P., Francis, P., Wolf, M., Januszewicz, E.H., Richardson, G., Scarlett, J., and Briggs, P. (2002) "Isolex 300i CD34-selected cells to support multiple cycles of high-dose therapy" Cytotherapy 4, 137-45.
Probst, M. et al., "Homologous bladder augmentation in dog with the bladder acellular matrix graft," *BJU International*, 2000, 85:362-71.
Prockop D.J. 1997 *Science* "Marrow Stromal Cells as Stem Cells for Nonhematopoietic Tissues," 276: 71-74.
Prockop, D.J., S.A. Azizi, et al. (2000) Potential use of marrow stromal cells as therapeutic vectors for diseases of the central nervous system: Prog Brain Res 128:293-7.
Puma, S.K. and M. Babu (2000) "Collagen based dressings—a review" Burns 26(1): 54-62.
Qian, X., Jin, L., and Lloyd, R.V. (1998) Percoll Density Gradient-Enriched Populations of Rat Pituitary Cells: Interleukin 6 Secretion, Proliferative Activity, and Nitric Oxide Synthase Expression: Endocr. Pathol. 9, 339-346.
Quirici, N., Soligo, D., Bossolasco, P., Servida, F., Lumini, C., and Deliliers, G.L. (2002) "Isolation of bone marrow mesenchymal stem cells by anti-nerve growth factor receptor antiobidies" Exp Hematol 30, 783-91.
Rajnoch, C., Chachques, J.C., Berrebi, A., Bruneval, P., Benoit, M.O., and Carpentier, A. (2001) "Cellular therapy reverses myocardial dysfunction" J Thorac Cardiovasc Surg 121(5), 871-8.
Ramirez-Zacarias et al., 1992, Quantitation of adipose conversion and triglycerides by staining intracytoplasmic lipids with Oil red O, Histochemistry 97(6):493-497.
Ramsay, T. G. et al., "Pre-Adipocyte Proliferation and Differentiation in Response to Hormone Supplementation of Decapitated Fetal Pig Sera," *J. Anim. Sci.,* 64:735-44, 1987.
Rando, et al., 1995 *Exp. Cell Res.* "The Fate of Myoblasts Following Transportation into Mature Muscle," 220:383-389.
Rando, Thomas A. and Helen M. Blau, "Primary Mouse Myoblast Purification, Characterization, and Transplantation for Cell-mediated Gene Therapy," *J. Cell Biol* 1994 125:1275-1287.
Rangappa, S., Fen, C., Lee, E.H., Bongso, A., and Wei, E.S. (2003) "Transformation of adult mesenchymal stem cells isolated from the fatty tissue into cardiomyocytes" Ann Thorac. Surg 75, 775-779.
Rehman, et al. "Angiogenic potential of subcutaneous adipose stromal cells for autologous cell therapy." Journal of the American College of Cardiology. 41(6)(Suppl A): 308A (Mar. 19, 2003).
Rehman, et al. "Secretion of angiogenic and antiapoptotic factors by human adipose stromal cells." Circulation. 109(10):1292-1298 (2004).
Reinecke H et al. 2002. Skeletal muscle stem cells do not transdifferentiate into cardiomyocytes after cardiac grafting. J. Mol. Cell. Cardiol. 34: 241-249.
Reitman et al., 2000, A-ZIP/F-1 mice lacking white fat: a model for understanging lipoatrophic diabetes, Int. J. Obes. Relat. Metab. Disord. 24 (Supp14):S11-S14.
Religa et al., 2005, Presence of bone marrow-derived circulating progenitor endothelial cells in the newly formed lymphatic vessels, Blood 106(13):4184-4190.
Remacle, M., G. Lawson et al (1999) "Correcting vocal fold immobility by autologous collagen injection for voice rehabilitation. A short-term study." Ann Otol Rhinol Laryngol 108(8): 788-83.
Remme, W.J. (2000) "Overview of the relationship between ischemia and congestive heart failure" Clin Cardiol 23, 4-8.
Reyes, M., Lund, T., Lenvik, T., Aguiar, D., Koodie, L., and Verfaillie, C.M. (2001) "Purification and ex vivo expansion of postnatal human marrow mesodermal progenitor cells" Blood 98, 2615-2625.
Richardson, J. B. et al., "Repair of human articular cartilage after implantation of autologous chondrocytes," *The Journal of Bone and Joint Surgery*, 1999, 81:1064-8 ).
Rickard, David J. et al., "Isolation and Characterization of Osteoblast Precursor Cells from Human Bone Marrow," *Journal of Bone and Mineral Research,* 1996, 11:312-24.
Rim et al., 2005, Mesenchymal stem cells from the outer ear: a novel adult stem cell model system for the study of adipogenesis, FASEB J. 19(9):1205-1207.
Rodriguez et al. "The human adipose tissue is a source of multipotent stem cells." Biochimie. 87(1):125-128 (2005).
Rubens, F. D. et al., "Tissue Factor Expression by Cells Used for Sodding of Prosthetic Vascular Grafts," *Journal of Surgical Research,* 72:22-8, 1997.
Rupnick et al., 2002, Adipose tissue mass can be regulated through the vasculature, PNAS 99(16):10730-10735.
Russell, S.W., Doe, W.F., Hoskins, R.G. and Cochrane, C.G. (1976) "Inflammatory cells in solid murine neoplasms. I. Tumor disaggregation and identification of constituent inflammatory cells" Int J Cancer 18, 322-30.
Ryden et al., Jan. 11, 2002, Mapping of early signaling events in tumor necrosis factor-alpha-mediated lipolysis in human fat cells, J. Biol. Chem. 277(2):1085-1091.
Saalbach, A., et al., 1997 *Cell and Tiss. Res.* "The Fibroblast-specific MAb AS02: a novel tool for detection and elimination of human fibroblasts," 290:593-599.
Safford et al. "In vivo engraftment and differentiation of murine adipose derived stromal cells" Blood, vol. 100, No. 11, 731a, (Nov. 2002).
Safford, Kristine M. et al., "Neurogenic differentiation of murine and human adipose-derived stromal cells," *Biochemical and Biophysical Research Communications,* 2002, 371-379.
Saito et al. "Transcoronary implantation of bone marrow stromal cells ameliorates cardiac function after myocardial infarction." The Journal of Thoracic and Cardiovascular Surgery. 126(1):114-122 (2003).
Saluja et al., Mar. 2003, Pancreatitis and associated lung injury: when MIF miffs, Gastroenterology, 124(3):844-847.
Salven et al., 2003, VEGFR-3 and CD133 identify a population of CD34+ lymphatic/vascular endothelial precursor cells, Blood 101(1):168-172.
Sanchez-Ramos, et al., 2000 "Adult Bone Marrow Stromal Cells Differentiate into Neural Cells in Vitro," Exp. Neurol. 164:247-256.
Sarnat, Harvey B. et al., "Neuronal nuclear antigen (NeuN): a marker of neuronal maturation in the early human fetal nervous system," *Brain & Development,* 1998, 20:88-94.
Sattler et al. "Liporecycling: a technique for facial rejuvination and body contouring" Dermantol. Surg. vol. 26, No. 12, 1140-1144 (Dec. 2000).
Savitz et al. "Cell Transplantation for stroke." Annals of Neurology. 52(3):266-275 (2002).
Scherberich, A. and A. Beretz (2000) "Culture of vascular cells in tridimensional (3-D) collagen: a methodological review" Therapie 55(1): 35-41.
Schmidt et al., Jan. 1992, A better model of acute pancreatitis for evaluating therapy, Ann Surg. 215(1):44-56.
Schoeller et al. "Histomorphologic and volumetric analysis of implanted autologous preadipocyte cultures suspended in fibrin glue: a potential new source for tissue augmentation." Aesthetic Plastic Surgery. 25(1):57-63 (2001).

(56) References Cited

OTHER PUBLICATIONS

Scholz, D., Cai, W.J., and Schaper, W. (2001) "Arteriogenesis, a new concept of vascular adaptation in occlusive disease" Angiogenesis 4, 247-257.
Scholz, D., Elasaesser, H., Sauer, A., Friedrich, C., Luttun, A., Carmeliet, P., and Schaper, W. (2003) "Bone marrow transplantation abolishes inhibition of arteriogenesis in placenta growth factor (PIGF)—mice" J Mol Cell Cardiol 35, 177-184.
Scholz,D., Ziegelhoeffer, T., Helisch, A., Wagner, S., Friedrich, C., Podzuweit, T. and Schaper, W. (2002) "Contribution of arteriogenesis and angiogenesis to postocculsive hindlimb perfusion in mice" J Mol Cell Cardiol 34, 775-787.
Schwartz, R.E., Reyes, M., Koodie, L., Jiang, Y., Blackstad, M., Lund, T., Lenvik, T., Johnson, S., Hu, W.S. and Verfaillie, C.M. (2002) "Multipotent adult progenitor cells from bone marrow differentiate into functional hepatocyte-like cells" J Clin Invest 109, 1291-302.
Schwartzmann, M. (2000) "Use of collagen membranes for guided bone regeneration: a review" Implant Dent 9(1): 63-6.
Schweitzer, C.M., Van Der, Schoot, Ce, Drager, A.M., Van der Valk, P., Zevenbergen, A., Hooibrink, B., Westra, A.H., and Langenhuijsen, M.M. (1995) "Isolation and culture of human bone marrow endothelial cells" Exp Hematol 23, 41-8.
Sclafani, A.P. and T. Romo, 3rd (2001) "Collagen, human collagen and fat: the search for a three-dimensional soft tissue filler" Facial Plast Surg 17(1): 79-85.
Sclafani, A.P., T. Romo, 3rd et al. (2002) "Rejuvenation of the aging lip with an injectable acellular dermal graft (cymetra)" Arch Facial Plast Surg 4(4): 252-7.
Scott, Douglas M. et al., "Collagen Synthesis in Cultured Osteoblast-like Cells," *Archives of Biochemistry and Biophysics,* 1980, 201:384-91.
Seale and Rudnicki 2000 *Dev. Biol.* "A New Look at the Origin, Function, and "Stem-Cell" Status of Muscle Satellite Cells," 218:115-124.
Sekiya et al., 2004, Adipogenic differentiation of human adult stem cells from bone marrow stroma (MSCs), J. Bone and Min. Res. 19(2):256-264.
Sekiya, I., Larson, B.L., Smith, J.R., Pochampally, R., Cui, J.G., and Prockop, D.J. (2002) "Expansion of human adult stem cells from bone marrow stroma: conditions that maximize the yields of early progenitors and evaluate their quality" Stem Cells 20, 530-541.
Sergeant, P., Blackstone, E., and Meyns, B. (1997) "Early and late outcome after CABG in patients with evolving myocardial infarction" Eur J Cardiothorac. Surg 11, 848-856.
Shalhoub, Victoria et al., "Downregulation of Cell Growth and Cell Cycle Regulated Genes during Chick Osteoblast Differentiation with the Reciprocal Expression of Histone Gene Variants," *Biochemistry,* 1989, 28:5318-22.
Shi, Q., S. Rafil, et al. (1998) "Evidence for circulating bone marrow-derived endothelial cells" Blood 92(2): 362-7.
Shigematsu, S., Yamauchi, K., Nakajima, K., Iijima, S., Aizawa, T., and Hashizume, K. (1999) "IGF-1 regulates migration and angiogenesis of human endothelial cells" Endocr. J 46 Suppl, S59-S62.
Shillabeer, et al., "A novel method for studying preadipocyte differentiation in vitro," *Intl. J. Obesity* 1996 20(Supp. 3), S77-S83.
Shore, J.W. (2000) "Injectable lyophilized particulate human fascia lata (Fascian) for lip, perioral and glabellar enhancement" Opthal Plast Reconstr Surg 16(1): 23-7.
Shukunami C., et. al., 1996 *Journ. Of Cell Bio.* "Chrondrogenic Differentiation of Clonal Mouse Embryonic Cell Line ATDC5 In Vitro: Differentiation-dependent Gene Expression of Parathyroid Hormone (PTH)/PTH-related Peptide Receptor," 133:2:457-468.
Shukunami, C., et al., 1998 *Exp. Cell Res.* "Sequential Progression of the Differentiation Program by Bone Morphogenetic Protein-2 in Chondrogenic Cell Line ATDC5," 241:1-11.
Siffert, Robert S., "The Role of Alkaline Phosphatase in Osteogenesis," *The Journal of Experimental Medicine,* 1951, 93:415-26.
Silberstein, L., et al., 1986 *Cell* "Developmental Progression of Myosin Gene Expression in Cultured Muscle Cells," 46:1075-1081.
Silver, F.H. and G. Pins (1992) "Cell growth on collagen: a review of tissue engineering using scaffolds containing extracellular matrix" J Long Term Eff Med Implants 2(1): 67-80.
Sivan-Loukianova et al. "CD34+ Blood cells accelerate vascularization and healing of diabetic mouse skin wounds" J. Vascular Research, vol. 40, No. 4, 368-377 (Jul.-Aug. 2003).
Šmahel, J., "Aspiration lipectomy and adipose tissue injection: pathophysiologic commentary," *European Journal of Plastic Surgery,* 14:126-31, 1991.
Smith et al., 2000, "Mesenchymal Stem Cells Derived From Bone Marrow and Human Adipose Tissue Exhibit Multilineage Potential," *Journal of Investigative Medicine*, 95A.
Smith, J.W. (1997) "Apheresis techniques and cellular immunomodulation" Ther. Apher. 1, 203-206.
Smith, R.J. and Sweetenham, J.W. (1995) "A mononuclear cell dose of 3 × 10(8)/kg predicts early multilineage recovery in patients with malignant lymphoma treated with carmustine, etoposide, Ara-C and melphalan (BEAM) and peripheral blood progenitor cell transplantation" Exp Hematol 23, 1581-8.
Smits, G., Holzgreve, W., and Hahn, S. (2000) "An examination of different Percoll density gradients and magnetic activated cell sorting (MACS) for the enrichment of fetal erythroblasts from maternal blood" Arch. Cynecol. Obstet. 263, 160-163.
Soda, et al., 1983, "Adipocyte stem cell: A brief review," *Int. J. of Cell Cloning,* 1:79-84.
Sodian, R., Lemke, T., Fritsche, C., Hoerstrup, S.P, Fu, P., Potapov, E.V., Hausmann, H., and Hetzer, R. (2002) "Tissue-engineering bioreactors: a new combined cell-seeding and perfusion system for vascular tissue engineering" Tissue Eng 8, 863-870.
Soli, M., Blanco, L., Riggert, J., Martinez, Clavel, A., Lucas, C., Lunghi, M., Belloni, M., Wolf, C., van Waeg, G., and Antoon, M. (2001) "A multicentre evaluation of a new filtration protocol for leucocyte depletion of high-haematocrit red blood cells collected by an utomated blood collection system" Vox Sang. 81, 108-112.
Sommer et al. "Current Concepts of Fat Graft Survival: Histology of Aspirated Adipose Tissue and Review of the Literature." Dermatologic Surgery. 26(12):1159-1166 (2000).
Sorisky et al., "From preadipocyte to Adipocyte: Differentiation-Directed Signals of Insulin from the Cell Surface to the Nucleus," *Critical Review in Clinical Laboratory Sciences* 1999 36(1), 1-34.
Speranza, M.L. and G. Valentini (1986) "A simple procedure for the purification of neutral salt soluble type I collagen from skin" Ital J Biochem 35(1): 42-8.
Springhorn, Jeremy P. et al., "Human Capillary Endothelial Cells from Abdominal Wall Adipose Tissue: Isolation Using an Anti-Pecam Antibody," *In Vitro Cellular & Developmental Biology—Animal,* 31:473-81, 1995.
Stamm, C., Westphal, B., Kleine, H.D., Petzsch, M., Kittner, C., Klinge, H., Schumichen, C., Nienaber, C.A., Freund, M. and Steinhoffm G. (2003) "Autologous bone-marrow stem-cell transplantation for myocardial regeneration" Lancet 4, 45-46.
Stashower et al., 1999, "Stromal progenitor cells present within liposuction and reduction abdominoplasty fat for autologous transfer to aged skin," *Dermatologic Surgery,* 25:12:945-949.
Stosich et al. "Adipose tissue engineering from human adult stem cells: clinical implications in plastic and reconstructive surgery." *Plast Reconstr Surg* 119, 71-83 (2007).
Strauer, B.E., M. Brehm, et al. (2002) "Repair of infarcted myocardium by autologous intracoronary mononuclear bone marrow cell transplantation in humans" Circulation 106(15): 1913-8.
Strem et al., 2005, Multipotential differentian of adipose tissue-derived stem cells, Keio J. Med 54(3):132-141.
Strutt et al., 1996, "Growth and differentiation of human adipose stromal cells in culture," *methods in Molecular Medicine: Human Cell Culture Protools,* 41-51.
Suga, S., et al., 1996,"*Eur. J. Cell Biol.* " Intracellular localization of antigens recognized by anti-vimentin monoclonal antibodies (mAbs): Cross-reactivities of anti-vimentin mAbs with other cellular components 70:84-91.
Sundberg, C., Kowanetz, M., Brown, L.F., Detmar, M., and Dvorak, H.F. (2002) "Stable expression of antiopoietin-1 and other markers

(56) References Cited

OTHER PUBLICATIONS by cultured pericytes: phenotypic similarities to a subpopulation of cells in maturing vessels during later stages of angiogenesis in vivo" Lab invest 82, 387-401.
Symmons et al., 2006, The world of biologics, Lupus, 15(3):122-126.
Syrjälä, M. et al., "A flow cytometric assay of CD34-postitive cell populations in the bone marrow," *British Journal of Haematology,* 1994, 88:679-84.
Tabata,Y. et al. "De novo formation of adipose tissue by controlled release of basic fibroblast growth factor." *Tissue Eng.* 6:6279-289 (2000).
Tacchetti, C, et al., 1992 *Exp Cell Res.* "Cell Condensation in Chondrogenic Differentiation," 200:26-33.
Tacchetti, C. et al., "In Vitro Morphogenesis of Chick Embryo Hypertrophic Cartilage," *The Journal of Cell Biology,* 1987, 105:999-1006.
Tafech et al., 2006, Destroying RNA as a Therapeutic Approach, Current Medicinal Chemistry, 13(8):863-81.
Takahashi, T., C. Kalka, et al. (1999) "Ischemia and cytokine-induced mobilization of bone marrow-derived endothelial progentiro cells for neovascularization" Nat Med 5(4): 434-8.
Takasaki, et al (1995) "Human type VI collagen: purification from human subcutaneous fat tissue and an immunohistochemical study of morphea and systemic sclerosis" J Dermatol 22(7): 480-5.
Tang et al., 2004, Commitment of C3H10T1/2 pluripotent stem cells to the adipocyte lineage, PNAS 101(26):9607-9611.
Tapscott, et al., 1988 *Science* "MyoD1: A Nuclear Phosphoprotein Requiring a Myc Homology Region to Convert Fibroblasts to Myoblasts," 242:405-411.
Tavassoli et al., 1981, "The Nature of Fibroblasts Derived From Adipose Tissue In-Vitro," *Clinical Research,* 29:5:871A.
Tavassoli, Mehdi, "In Vivo Development of Adipose Tissue Following Implantation of Lipid-Depleted Cultured Adipocyte," *Experimental Cell Research,* 137:55-62, 1982.
Thomas, E.D. (1994) "Stem Cell Transplantation: Past, Present and Future" Stem Cells 12: 539-544.
Thornell, et al., 1984 *J. Neurol. Sci.* "Development of Fiber Types in Human Fetal Muscle," 66:107-115.
Tintut et al., 2003, Multilineage potential of cells from the artery wall, Circulation, 108(20):2505-2510.
Toma, J.G., Akhavan, M., Fernandes, K.J., Barnabe-Heider, F., Sadikot, A., Kaplan, D.R. and Miller, F.D. (2001) "Isolation of multipotent adult stem cells from the dermis of mammalian skin" Nat Cell Biol 3, 778-84.2.
Tontonoz, Peter et al., "mPPARg2: tissue-specific regulator of an adipocyte enhancer," *Genes & Development,* 1994, 8:1224-34.
Torio-Padron et al. "Engineering of adipose tissue by injection of human preadipocytes in fibrin." *Aesthetic Plast Surg* 31, 285-293 (2007).
Tosh, et al. "Conversion of pancreatic cells to hepatocytes." Biochem Soc Trans 30:51-55 (2002).
Totonoz, et al., 1995 *Nucl. Acid Res* "mPPARg2: tissue-specific regulator of an adipocyte enhancer."
Trayhurn, P. and Margaret Ashwell, "Control of white and brown adipose tissues by the autonomic nervous system," *The Proceedings of the Nutrition Society,* 1987, 46:135-42.
Trujillo et al., 2005, Apoptosis through targeted activation of Caspase8 ("ATTAC-mice"): novel mouse models of inducible and reversible tissue ablation, Cell Cycle 4(9):1141-1145.
Tsonis and Goetinck 1990 *Exp. Cell Res.* "Cell Density Dependent Effect of a Tumor Promoter on Proliferation and Chondrogenesis of Limb Bud Mesenchymal Cells," 190:247-253.
Twentyman, P.R. and Yuhas, J.M. (1980) "Use of bacterial neutral protease for disaggregation of mouse tumours and multicellular tumor spheroids" Cancer Lett 9, 225-8.
Uitto, J. (1971) "Collagen biosynthesis in human skin. A review with emphasis on scleroderma" Ann Clin Res 3(5): 250-8.
Urban et al. "Degeneration of the intervertebral disc." Arthritis Research & Therapy. 5(3):120-130 (2003).
Urbich et al. "Endothelial Progenitor Cells." Trends in Cardiovascular Medicine. 14(8):318-322 (2004).
Urs et al., 2004, Gene expression profiling in human preadipocytes and adipocytes by microarray analysis, J. Nutr. 134:762-770.
Van et al., 1978, "Complete Differentiation of Adipocyte Precursors," *Cell Tissue,* 195:317-329.
Van Merris, V., Meyer, E., Dosogne, H., and Burvenich, C. (2001) "Separation of bovine bone marrow into maturation-related myeloid cell fractions" Vet. Immunol. Immunopathol. 83, 11-17.
Vandenburgh, Herman H. and Patricia Karlisch, "Longitudinal Growth of Skeletal Myotubes In Vitro in a New Horizontal Mechanical Cell Stimulator," *In Vitro Cellular & Developmental Biology,* 1989, 25:607-16.
Varzaneh et al., 1994, Extracellular Matrix Components Secreted by Microvascular Endothelial Cells Stimulate Preadipocyte Differentiation In Vitro, Metabolism 43(7):906-912.
Vassaux, et al., "Proliferation and differentiation of Rat Adipose Precursor Cells in Chemically Defined Medium: Differential Action of Anti-Adipogenic Agents," *Journal of Cellular Physiology* 1994 161(2), 249-256.
Verma (1990), "Gene therapy." Scientific American 263(5): 68-84.
Vojtassak, et al., 2006; "Autologous Biograft and Mesenchymal Stem Cells in Treatment of the Diabetic Foot," Neuro Endocrinol Lett. 27 Suppl 2:134-7.
von der Mark, et al., 1977 *Nature* "Relationship between cell shape and type of collagen synthesised as chondrocytes lose their cartilage phenotype in culture," 267:531-532.
von Heimburg, D. et al. "Human preadipocytes seeded on freeze-dried collagen scaffolds investigated in vitro and in vivo." *Biomaterials* 22, 429-38 (2001).
Vukicevic et al., 1992 *Exp. Cell Res* "Identification of Multiple Active Growth factors in Basement Membrane Matrigel Suggests Caution in Interpretation of Cellular Activity Related to Extracellular Matrix Components,", 202(1), 1-8.
Wabitsch, et al., "Biological Effects of Human Growth Hormone in Rat Adipocyte Precursor Cells and Newly Differentiated Adipocytes in primary Culture," *Metabolism* 1996 vol. 45,No. 1 pp. 34-42.
Wagner et al., 2005, Comparative characteristics of mesenchymal stem cells from human bone marrow, adipose tissue, and umbilical cord blood, Experimental Hematology 33:1402-1416.
Wakitani, Shigeyuki et al., "Mesenchymal Cell-Based Repair of Large, Full-Thickness Defects of Articular Cartilage," *The Journal of Bone and Joint Surgery,* 1994, 76A:579-92.
Wakitani, Shigeyuki et al., "Myogenic Cells Derived from Rat Bone Marrow Mesenchymal Stem Cells Exposed to 5-Azacytidine," *Muscle & Nerve,* 1995, 18:1417-26.
Walther, W. and Stein, U. (2000) Viral vectors for gene transfer: a review of their use in the treatment of human diseases: Drugs 609, 249-71.
Walton et al. "De novo adipose formation in a vascularized engineered construct." *Microsurgery* 24, 378-384 (2004).
Wang, L., Zeng, H., Wang, P., Soker, S., and Mukhopadhyay, D. (2003) "Neuropilin-1 mediated vascular permeability factor/vascular endothelial growth factor-dependent endothelial cell migration" J Biol Chem 278, 48848-48860.
Watts, M.J., Somervaille, T.C., Ings, S.J., Ahmed, F., Khwaja, A., Yong, K. and Linch, D.C. (2002) "Variable product purity and functional capacity after CD34 selection: a direct comparison of the CliniMACS (v2.1) and Isolex 300i(v2.5) clinical scale devices" Br J Haematol 118, 117-23.
Weiner, Francis R. et al. "Regulation of collagen Gene Expression in 3T3-L1 Cells. Effects of Adipocyte pocyte Differentiation and Tumor necrosis Factor a," Biochem 1989 28:4094-4099.
Weintraub, et al., 1991 *Science* "The myoD Gene Family: Nodal Point During Specification of the Muscle Cell Lineage," 251:761-766.
Weintraub, Harold et al. "Tissue-specific gene activation by MyoD: determination of specificity by cis-acting repression elements," *Genes & Development,* 1994, 8:2203-11.
Werlich, T., K.J. Stiller, et al. (1999) "Experimental studies on the stem cell concept of liver regeneration II" Exp Toxicol Pathol 51(1): 93-8.

(56) References Cited

OTHER PUBLICATIONS

Williams, Irene H. and S. Efthimios Polakis, "Differentiation of 3T3-L1 Fibroblasts to Adipocytes, the Effect of Indomethacin, Prostaglandin $E_1$ and Cyclic AMP on the Process of Differentiation" *Biochem Biophys. Res.Commun.* 1977 77:175-186.
Williams, John T. et al., "Cells Isolated from Adult Human Skeletal Muscle Capable of Differentiating into Multiple Mesodermal Phenotypes," *The American Surgeon,* 65:22-6, 1999.
Williams, S.K., McKenney, S. and Jarrell, B.E. (1995) "Collagenase lot selection and purification for adipose tissue digestion" Cell Transplant 4, 281-9.
Williams, Stuart K. et al., "Liposuction-derived human fat used for vascular graft sodding contains endothelial cells and not mesothelial cells as the major cell type," *Journal of Vascular Surgery,* 19:916-23, 1994.
Wilting et al., 2007, The Proepicardium Delivers Hemangioblasts but not Lymphangioblasts to the Developing Heart, Developmental Biology 305:451-459.
Wilting et al., Aug. 2002, The transcription factor Prox1 is a marker for lymphatic endothelial cells in normal and diseased human tissues, The FASEB Journal, 16:1271-1273.
Wise, Leigh S. and Howard Green, "Participation of One Isozyme of Cytosolic Glycerophosphate Dehydrogenase in the Adipose Conversion of 3T3 Cells," *J. Biol. Chem.* 1979 254:273-275.
Włodarski, Krzysztof H., "Section III. Basic Science and Pathology. Properties and Origin of Osteoblasts," *Clinical Orthopaedics and Related Research,* 252:276-93, 1990.
Wolinsky et al., Feb. 1990, Use of a perforated balloon catheter to deliver concentrated heparin into the wall of the normal canine artery, J. Am. Coll. Cardiol. 15(2):475-481.
Wollert et al. "Intracoronary autologous bone-marrow cell transfer after myocardial infarction: the BOOST randomised controlled clinical trial." The Lancet Limited. 364(9429):141-148 (2004).
Woodbury, et al., 2000 *J. Neurosci. Res. Science* "Adult Rat and Human Bone Marrow Stromal cells Differentiate Into Neurons," 61:364-370 Young, 2000 *Science* "A Time for Restraint," 287:1424.
Wu et al. "Preparation and assessment of glutaraldehyde-crosslinked collagen-chitosan hydrogels for adipose tissue engineering." *J Biomed Mater Res A* 81, 59-65 (2007).
Xie et al., 2006, Preparation of bupleurum nasal spray and evaluation on its safety and efficacy, Chem. Pharm. Bull., 54(1):48-53.
Xiong, B., Gong, L.L., Zhang, F., Hu, M.B. and Yuan, H.Y. (2002) "TGF beta1 expression and angiogenesis in colorectal cancer tissue" World J Gastroenterol. 8, 496-498.
Yavorkovsky, L., E. Lai, et al. (1995) "Participation of small intraportal stem cells in the restitutive response of the liver to periportal necrosis induced by allyl alochol" Hepatology 21(6): 1702-12.
Ye, Q., Zund, G., Benedikt, P., Jockenhoevel, S., Hoerstrup, S.P., Sakyama, S., Hubbell, J.A. and Turina, M. (2000) "Fibrin gel a three dimensional matrix in cardiovascular tissue engineering" Eur J Cardiothorac Surg 17, 587-91.
Yin, L., D. Lynch, et al. (1999) "Participation of different cell types in the restitutive response of the rat liver to periportal injury induced by allyl alcohol" J Hepatol 31(3): 497-507.
Yokoyama, T., N. Yoshimural et al (2001) "Persistence and survival of autologous muscle derived cells versus bovine collagen as potential treatment of stress urinary incontinence" J Urol 165(1): 271-6.
Yoo, Jung U. and Brian Johnstone, "The Role of Osteochondral Progenitor Cells in Fracture Repair," *Clinical Orthopaedics and Related Research,* 1998, 355S:S73-81 ).
Yoon, Kyonggeun et al., "Characterization of the Rat osteocalcin Gene: Stimulation of Promoter Activity by 1,25-Dihydroxyvitamin D3," *Biochem.* 1988 27:8521-8526.
Young et al., "Mesenchymal Stem Cells Reside Within the Connective Tissues of Many Organs," *Developmental Dynamics* 1995 202(2), 137-144.
Young, "A Time for Restraint", 2000 Science 287:1424.
Young, H.E., Steele, T.A., Bray, R.A., Hudson, J., Floyd, J.A., Hawkins, K., Thomas K., Austin, T., Edwards, C. Cuzzourt, J., Duenzl, M., Lucas, P.A., and Black, A.C., Jr. (2001) "Human reserve pluripotent mesenchymal stem cells are present in the connective tissues of skeletal muscle and dermis derived from fetal, adult and geriatric donors" Anat Rec 264, 51-62.
Young, Henry E. et al., "Human Pluripotent and Progenitor Cells Display Cell Surface Cluster Differentiation Markers CD10, CD13, CD56, and MHC Class-I," *Proc. Soc. Exp. Biol. Med.,* 1999, 221:63-71.
Yuksel et al., Apr. 2000, De novo adipose tissue generation through long-term, local delivery of insulin and insulin-like growth factor-1 by PLGA/PEG microspheres in an in vivo rat model: a novel concept and capability, Plastic and Reconstructive Surgery, 105:1721-1729.
Zalin, RJ 1987 *Exp. Cell Res.* "The Role of Hormones and Prostanoids in the in Vitro Proliferation and differentiation of Human Myoblasts," 172:265-281.
Zezulak, Kathleen M. and Howard Green, "Specificity of Gene Expression in Adipocytes," *Molecular and Cellular Biology,* 1985, 5:419-21.
Zimmerman, W.H., Diddie, N., Wasmeier, G.H. Nixdorff, U., Hess, A., Meinychenko, I., Boy, O., Neuhuber, W.L., Weyand, M., and Eschenhagen, T. (2002) "Cardiac grafting of engineered heart tissue in syngenic rats" Circulation 106, 1151-1157.
Zimmermann, W.H., Melnychenko, I., and Eschenhagen, T. (2004) "Engineered heart tisue for regeneration of diseased hearts" Biomaterials 25, 1639-1647.
Cheifetz et al., 1988, Analysis of intracellular osteopontin as a marker of osteoblastic cell differentiation and mesenchymal cell migration,European Journal of Oral Sciences, 106(Supp. 1):401-7.
Zuk, Patricia A. et al., "Human Adipose Tissue is a Source of Multipotent Stem Cells," *Molecular Biology of the Cell,* 2002, 13:4279-4295.
Zuk, Patricia Z. et al., "Multilineage Cells from Human Adipose Tissue: Implication for Cell-Based Therapies," *Tissue Engineering,* Apr. 2001, 7:211-28.
Zvaifler, et al., 2000, "Mesenchymal precursor cells in the blood of normal individuals," *Arthritis Res.* 2:477-488.
Bergan et al., 1996, Electroporation of synthetic oligodeoxynucleotides: a novel technique for ex vivo bone marrow purging, Blood, 88(2):731-741.
Bhagavati, et al., 2004, Isolation and enrichment of skeletal muscle progenitor cells from mouse bone marrow, Biochem. Biophys. Res. Comm. 318(1):318-24.
Caplan and Goldberg, 1999, Principles of tissue engineered regeneration of skeletal tissues, Clin Orthop Suppl. 367: 12-16.
Cousin, et al. (2003), "Reconstitution of Lethally Irradiated Mice by Cells Isolated From Adipose Tissue", Biochem. Biomed. Res. Comm. 310:1016-1022.
Craiu, et al., 2005, Flowing cells through pulsed electric fields efficiently purges stem cell preparations of contaminating myeloma cells while preserving stem cell function, Blood 105(5):2235-2238.
Cui, et al., 2006, Effects of low-intensity ultrasound on chondrogenic differentiation of mesenchymal stem cells embedded in polyglycolic acid: an in vivo study, Tissue Eng. 12(1):75-82.
De Ugarte, "Comparison of Multi-Lineage Cells from Human Adipose Tissue and Bone Marrow," Cells Tissues Organs, 2003.
Di Carlo, et al., 2004, Hypoxia inhibits myogenic differentiation through accelerated MyoD degradation, The Journal of Biological Chemistry, 279(16):16332-338.
Duan, "Treatment of Myocardial Ischemia with Bone Marrow-Derived Mesenchymal Stem Cells Overexpressing Hepatocyte Growth Factor," Molecular Therapy, 2003, pp. 467-474.
Ebisawa, et al., 2004, Ultrasound enhances transforming growth factor B-mediated chondrocyte differentiation of human mesenchymal stem cells, Tissue Eng. 10(5-6):921-9.

* cited by examiner

SYSTEMS, METHODS AND COMPOSITIONS FOR OPTIMIZING TISSUE AND CELL ENRICHED GRAFTS

The present application claims priority to U.S. Provisional Application Ser. No. 61/174,860, filed on May 1, 2009, by Peterson et al., and entitled "SYSTEMS, METHODS AND COMPOSITIONS FOR OPTIMIZING TISSUE AND CELL GRAFTS," the entire disclosure of which is herein expressly incorporated by reference in its entirety.

FIELD OF THE INVENTION

Embodiments disclosed herein generally relate to compositions that comprise grafts, implants, or transplantable preparations comprising adipose tissue with and without a population of adipose-derived regenerative cells (e.g., a concentrated population of adipose-derived regenerative cells that comprise stem cells) and methods and systems for preparing, optimizing and administering the same.

BACKGROUND OF THE INVENTION

The transfer of adipose tissue to various regions of the body is a relatively common cosmetic, therapeutic and structural procedure involving the harvest of adipose tissue from one location and re-implantation of the harvested and, oftentimes processed tissue, in another location (see Coleman 1995; and Coleman 2001). While being largely used for repair of small cosmetic defects such as facial folds, wrinkles, pock marks and divots; the transfer of adipose tissue has recently been used for cosmetic and/or therapeutic breast augmentation and reconstruction (Bircoll and Novack 1987; and Dixon 1988), and augmentation of the buttocks (Cardenas-Camarena, Lacouture et al. 1999; de Pedroza 2000; and Peren, Gomez et al. 2000).

In the past, adipose tissue grafts and methods of adipose tissue transfer have been plagued with difficulties and side effects including necrosis, absorption of the implant by the body, infection (Castello, Barros et al. 1999; Valdatta, Thione et al. 2001), calcifications and scarring (Huch, Kunzi et al. 1998), inconsistent engraftment, (Eremia and Newman 2000), lack of durability, and other problems arising from lack of neovascularization and necrosis of the transplanted tissue. One of the biggest challenges in adipose tissue transfer is absorption of the implant by the body and volume retention of adipose tissue grafts following transfer. When adipose tissue is harvested or washed, the space between individual pieces of harvested adipose tissue is filled by liquid (e.g., water, blood, tumescent solution, oil). When this tissue/fluid mixture is implanted into a recipient the liquid portion is rapidly absorbed by the body resulting in loss of volume. The process by which the amount of fluid is removed from the tissue/fluid mixture is frequently referred to as "drying the adipose tissue" or "dehydrating the adipose tissue". The content of red and white blood cells and the like within an adipose tissue graft can also significantly affect the volume of graft retained after graft transplantation, due to induction or exacerbation of an inflammatory response. Another aspect of tissue retention relates t the amount of lipid within the adipose tissue graft. It understood that the presence of free lipid (meaning lipids released from dead or damaged adipocytes; also referred to as oil) in adipose tissue grafts can result in induction or exacerbation of an inflammatory response with substantial phagocytic activity and consequent loss of graft volume.

It is also known that mixing unprocessed adipose tissue with a concentrated population of adipose-derived regenerative cells overcomes many of the problems associated with adipose tissue grafts and adipose tissue transfer, as described above. Specifically, supplementing unprocessed adipose tissue with concentrated populations of adipose-derived cells comprising adipose-derived stem cells increases the weight, vascularization, and retention of fat grafts. (See U.S. Pat. No. 7,390,484 and co-pending U.S. Patent Application Publication No. 2005/0025755, herein expressly incorporated by reference in their entireties). Adipose tissue fragments supplemented, or mixed, with a concentrated population of cells including adipose-derived stem cells exhibit improved neoangiogeneis and perfusion in grafts when compared to unsupplemented grafts of adipose tissue alone in animal models. Further, adipose tissue grafts supplemented with adipose-derived regenerative cells that comprise adipose derived stem cells show increased graft retention and weight over time, when compared to unsupplemented grafts. (See U.S. Patent Application Publication No. 2005/0025755). Further, the processing of adipose tissue in a closed, sterile fluid pathway greatly reduces the chance of infection. The improvement in autologous transfer of adipose tissue seen in the animal models described above has also been replicated in human clinical studies. Nevertheless, the isolation and purification of concentrated populations of adipose-derived regenerative cells comprising adipose-derived stem cells (ADSCs), usually involves a series of washing, digestion, filtration and/or centrifugation steps, which can reduce the yield of viable cells, require mechanical equipment and specialized clinicians, and/or can compromise the quality, appearance, longevity, hydration or efficacy of the graft.

The need for additional approaches to prepare and optimize adipose tissue grafts and implants and to isolate and/or concentrate adipose-derived regenerative cells is manifest.

SUMMARY OF THE INVENTION

Embodiments described herein relate to devices to process adipose tissue grafts, as well as approaches for preparation of adipose tissue grafts and adipose tissue grafts supplemented with adipose-derived regenerative cells.

Several embodiments provided herein concern devices for preparing tissue for an adipose tissue graft. In some embodiments, the device can include a flexible, collapsible bag having a first chamber and a second chamber which are defined by a filter having pores. The device can also include a separator located within the second chamber, and one or more inlet ports and an outlet port connected to the flexible, collapsible bag. The inlet port can be configured to allow the aseptic introduction of adipose tissue into the first chamber; and the outlet port can be configured to aseptically remove liquid and cells from the second chamber.

In some embodiments, the separator can be a free floating porous structure within the second chamber. In some embodiments, the separator can be porous structure that defines a third chamber within the second chamber. In some embodiments, the separator can include a lipid-wicking material, such as a polyester mesh screen or the like. In some embodiments the separator can be a porous structure, having pores that are larger than the pores of the filter of the system. For example, in some embodiments, the pores of the separator have a pore size that can be greater than or equal to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 times the pore size of the pores of the filter. In some embodiments, the pore size of the separator can be between about 300 and 2000 μm. In some embodiments, the pore size of the filter can be greater than or equal to about 30 μm, e.g., between about 30 μm and about 200 μm. In some embodiments, the pore size of the filter is 35 μm.

In some embodiments, the inlet port can be configured to releasably connect with an adapter. In some embodiments, the adapter can be configured to releasably connect with the tip of a syringe barrel, such as a 60 or a 250 ml syringe, a Toomey syringe, or the like. In some embodiments, the inlet port can be configured to allow material to enter into the port, but not to exit from the port. For example, in some embodiments, the inlet port includes or is configured to be coupled to a deformable plastic valve and/or a tissue access port assembly. In some embodiments, the inlet port can be configured to be attached to a cannula, while maintaining a sterile fluid/tissue pathway.

In some embodiments, the device can include a second device, wherein the second device is an adipose-derived regenerative cell isolation device. In some embodiments, the adipose-derived regenerative cell isolation device can be attached to the first device for preparing tissue for an adipose tissue graft while maintaining a closed pathway. In some embodiments, the adipose-derived regenerative cell isolation device can be a device as described herein above. In some embodiments, the second device can be connected to the device for preparing tissue for an adipose tissue graft by a conduit that can be configured to transfer isolated adipose-derived regenerative cells from the second device to the first chamber of the device for preparing tissue for an adipose tissue graft. In some embodiments, the conduit can include a Y connection.

Some embodiments provided herein relate to a method of making an adipose tissue graft. The method can include the steps of obtaining a first portion of unprocessed adipose tissue; rinsing the first portion of unprocessed adipose tissue with a physiologic solution; and dehydrating the rinsed adipose tissue to an amount of hydration that is less than the amount of hydration present in the first portion of unprocessed adipose tissue prior to dehydration. For example, in some embodiments, the rinsed adipose tissue is dehydrated to a liquid content that is less than about ½, ⅓, or ¼ times (preferably about ⅓ times) that of said first portion of unprocessed adipose tissue prior to dehydration.

In some embodiments, the physiologic solution can be Lactated Ringer's solution, Ringer's acetate, saline, phosphate buffered saline, PLASMALYTE™ solution, crystalloid solutions and IV fluids, colloid solutions and IV fluids, five percent dextrose in water (D5W), Hartmann's Solution or the like.

In some embodiments, the method can additionally include the steps of isolating a population of adipose-derived regenerative cells from a second portion of adipose tissue and contacting the dehydrated adipose tissue with the isolated population of adipose-derived regenerative cells under conditions that allow the isolated population of adipose-derived regenerative cells to permeate through the dehydrated adipose tissue. In some embodiments, the isolated population of adipose-derived regenerative cells is not subjected to centrifugation prior to contacting the dehydrated adipose tissue. In some embodiments, the isolated population of adipose-derived regenerative cells can be prepared in a device disclosed herein above, by contacting adipose tissue present in the first chamber of the device with a means of releasing cells from the connective tissue matrix, for example, and enzyme solution comprising collagenase under conditions that liberate said cells. In some embodiments, such conditions that liberate said cells include heat, cooling, mechanical digestion, ultrasound or laser assisted liberation or other methods known in the art and described U.S. Pat. No. 7,390,484, which is expressly incorporated herein in its entirety. In some embodiments, the contacting step can be performed in a second device (e.g. a device having the same structure as the first device) attached to the first device.

Some embodiments relate to a method of producing an adipose tissue graft including the steps of obtaining a first portion of unprocessed adipose tissue introducing the first portion of unprocessed adipose tissue into the first chamber of a device described above; adding a physiologic wash solution to the first chamber with the unprocessed adipose tissue to rinse the unprocessed adipose tissue; and removing fluid (e.g., water, physiologic wash solution, blood, free lipid, or the like, or any combination thereof), from the second chamber of the device, thereby drying the adipose tissue and reducing the free lipid content.

In some embodiments, the method can additionally include the steps of isolating a population of adipose-derived regenerative cells from a second portion of adipose tissue and contacting the dehydrated adipose tissue with the isolated population of adipose-derived regenerative cells under conditions that allow the isolated population of adipose-derived regenerative cells to permeate through the dehydrated adipose tissue. In some embodiments, the isolated population of adipose-derived regenerative cells is not subjected to centrifugation prior to contacting the dehydrated adipose tissue. In some embodiments, the isolated population of adipose-derived regenerative cells of is prepared in a device disclosed herein by contacting adipose tissue present in the first chamber of the device with a means of releasing cells from the connective tissue matrix, for example, and enzyme solution comprising collagenase under conditions that liberate the cells. In some embodiments, such conditions that liberate said cells include heat, cooling, mechanical digestion, ultrasound or laser assisted liberation or other methods known in the art and described U.S. Pat. No. 7,390,484, which is expressly incorporated herein in its entirety. In some embodiments, the contacting step can be performed in a second device (e.g. a device having the same structure as the first device) attached to the first device.

BRIEF DESCRIPTION OF THE DRAWINGS

FIG. 14A shows a canister with a first chamber for processing adipose tissue, and a second chamber, for supplementing adipose tissue with lipodigestate, for grafting. FIG. 14B depicts an exemplary housing/platform for the canister shown in FIG. 14A.

DETAILED DESCRIPTION OF THE PREFERRED EMBODIMENT

Figure 1:
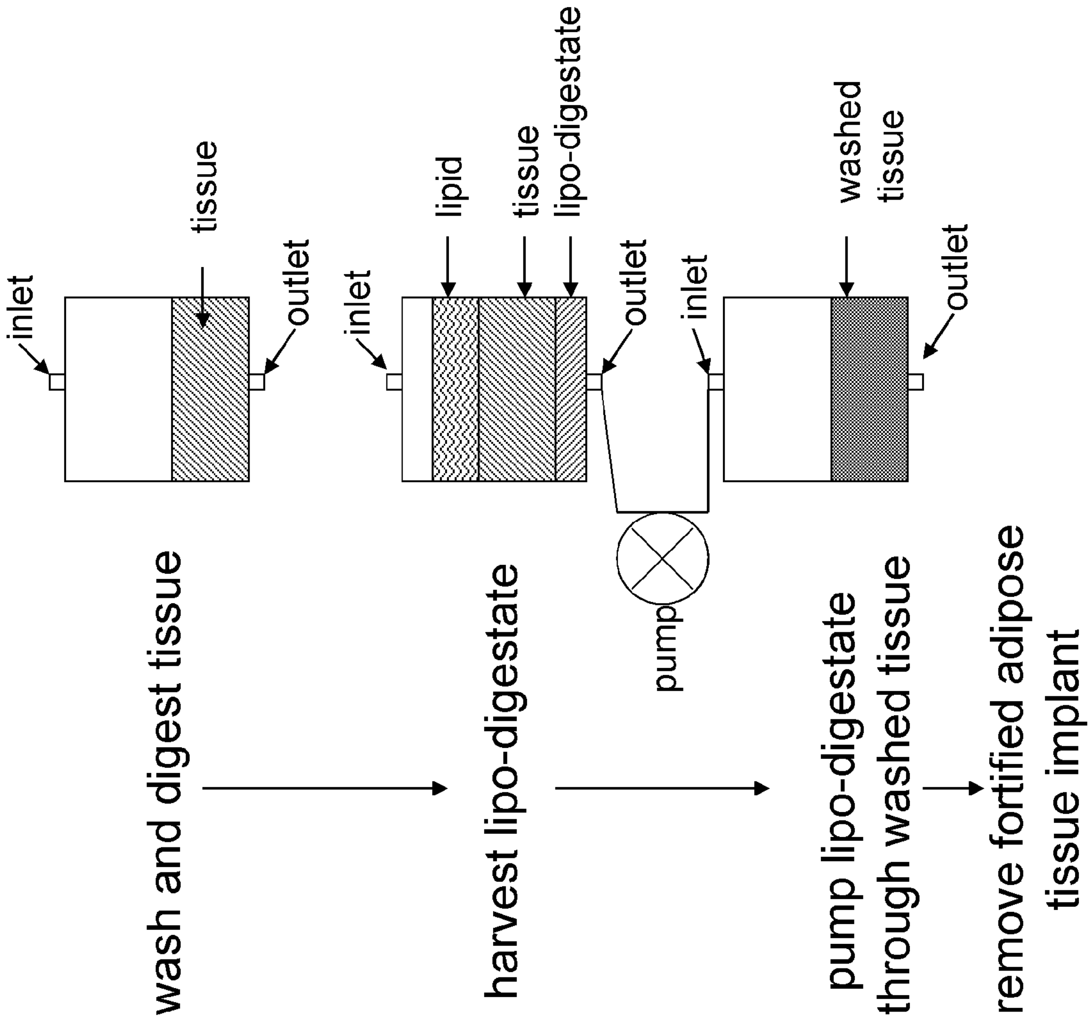
FIG. 1 shows a diagram illustrating exemplary graft supplementation methods disclosed herein.

Embodiments disclosed herein relate to methods and systems for the production of adipose tissue grafts (e.g., "fat grafts") or adipose tissue implants, either alone or supplemented, enhanced, or fortified with adipose-derived regenerative cells (e.g., a cell population that comprises adipose-derived stem cells, endothelial cells and/or progenitor cells). The embodiments disclosed herein are based, in part, on the discovery of a device or system that can be used for the rapid preparation and optimization of adipose tissue grafts, implants, and for the preparation of grafts and implants enriched with a population of adipose-derived regenerative cells (e.g., a cell population comprising adipose derived stem cells) by, for example, gravity flow and, if desired, in the absence of centrifugation, high pressure, or vacuum filtration. As discussed herein below, the adipose tissue grafts prepared using the devices disclosed herein have reduced levels of fluid, blood cells, and free lipid or oil content compared to grafts prepared using conventional techniques. Notably, the adipose tissue grafts prepared using the devices disclosed herein need not be subjected to strong mechanical forces, which may lead to decreased cell viability and reduced retention of the adipose tissue graft. Using the devices disclosed herein, one can obtain a more predictable and stable adipose-tissue implant.

The embodiments disclosed herein are also based, in part, on Applicants' discovery that intact adipose tissue fragments or "unprocessed adipose tissue matrix" can be used to filter, bind and thereby effectively concentrate in situ the adipose-derived regenerative cells that are provided vis a vis a solution or suspension of digested or partially or fully disaggregated adipose tissue. In some embodiments, "dried adipose tissue" or "dehydrated adipose tissue" can be used to filter, bind and thereby effectively concentrate in situ adipose-derived regenerative cells provided in the form of lipo-digestate. In some embodiments, the "unprocessed adipose tissue matrix" can be dried or dehydrated after adding the lipo-digestate. Accordingly, it has been realized that in some embodiments, concentration of the cellular component of disaggregated adipose tissue prior to augmentation, supplementation, or fortification of an adipose tissue graft or fat graft is no longer required.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope as defined by the appended claims. Aspects of the present invention may be practiced in conjunction with various cell or tissue separation techniques that are conventionally used in the art, and only so much of the commonly practiced process steps are included herein as are necessary to provide an understanding of the present invention.

Dried or Dehydrated Adipose Tissue

Some embodiments provided herein relate to methods of producing dried or dehydrated adipose tissue grafts that can be used directly in autologous transplantation procedures, e.g., autologous transplantation, or that can be fortified with cells (e.g., adipose-derived regenerative cells, adipose-derived stem cells, or the like), additives or the like prior to transplantation.

The term "adipose tissue," in some contexts, may refer to fat including the connective tissue that stores fat. Adipose tissue contains multiple regenerative cell types, including adipose-derived stem cells ("ADSCs"), endothelial progenitor and precursor cells, pericytes, macrophages, fibroblasts, lymphatic cells including lymphatic endothelial cells, etc., bound up by the connective tissue matrix. In some embodiments, a unit of adipose tissue is removed from a subject to generate an adipose tissue graft.

A "unit of adipose tissue" refers to a discrete or measurable amount of adipose tissue, which can be measured by determining the weight and/or volume of the unit. A unit of adipose tissue may refer to the entire amount of adipose tissue removed from a patient, or an amount that is less than the entire amount of adipose tissue removed from a patient. Thus, a unit of adipose tissue may be combined with another unit of adipose tissue to form a unit of adipose tissue that has a weight or volume that is the sum of the individual units.

In some embodiments, one or more units of adipose tissue is/are removed from a subject. The adipose tissue used in the embodiments described herein can be obtained by any method known to a person of ordinary skill in the art. For example, adipose tissue can be removed from a patient by suction-assisted lipoplasty, ultrasound-assisted lipoplasty, excisional lipectomy, laser lipoplasty, water jet lipoplasty, or the like. In addition, the procedures may include a combination of such procedures, such as a combination of excisional lipectomy and suction-assisted lipoplasty. Preferably, the adipose tissue is collected in a manner that preserves the viability of the tissue and its cellular component and minimizes the likelihood of contamination of the collected material with potentially infectious organisms, such as bacteria and/or viruses. Thus, in preferred embodiments, the tissue extraction is performed in a sterile or aseptic manner to minimize contamination, e.g., in a closed sterile fluid/tissue pathway. In some embodiments, suction assisted lipoplasty is used to remove the adipose tissue from a patient, thereby providing a minimally invasive method of collecting tissue with reduced potential for cell or tissue damage that may be associated with other techniques, such as ultrasound assisted lipoplasty.

For suction-assisted lipoplastic procedures, adipose tissue is collected by insertion of a cannula into or near an adipose tissue depot present in the subject followed by aspiration of the adipose into a suction device. In one embodiment, a small cannula can be coupled to a syringe, and the adipose tissue can be aspirated using manual force. Using a syringe or other similar device can be used to harvest relatively moderate amounts of adipose tissue (e.g., from 0.1 ml to several hundred milliliters of adipose tissue). Procedures employing these relatively small devices have the advantage that the procedures can be performed with only local anesthesia, as opposed to general anesthesia. Larger volumes of adipose tissue above this range (e.g., greater than several hundred milliliters) may require general anesthesia at the discretion of the donor and the person performing the collection procedure. When larger volumes of adipose tissue are desired to be removed, relatively larger cannulas and automated suction devices can be employed in the procedure.

Excisional lipectomy procedures include, and are not limited to, procedures in which adipose tissue-containing tissue (e.g., skin) is removed by excision such as surgical dissection under direct or indirect visualization of the tissue being excised. In certain embodiments this may occur as an incidental part of the procedure; that is, where the primary purpose of the surgery is the removal of tissue (e.g., skin in bariatric or cosmetic surgery) and in which adipose tissue is removed along with the tissue of primary interest.

The amount of adipose tissue collected for use in the methods disclosed herein is dependent on a number of variables including, but not limited to, the body mass index of the donor, the availability of accessible adipose tissue harvest sites, concomitant and pre-existing medications and conditions (such as anticoagulant therapy), and the purpose for which the tissue is being collected. Engraftment of adipose tissue transplants has been shown to be cell dose-dependent with threshold effects. Thus, it is likely that the general principle that "more is better" will be applied within the limits set by other variables and that where feasible the harvest will collect as much tissue as possible.

In some embodiments, e.g. in embodiments wherein the dried or dehydrated adipose tissue is used to make a fortified or supplemented adipose tissue graft, a unit of adipose tissue is divided into portions. The first portion of the adipose tissue is not digested, and is either not processed at all, or rinsed or washed to obtain dried or dehydrated adipose tissue as described herein below. The first portion of unprocessed, dried, or dehydrated adipose tissue can serve as the graft foundation that is supplemented with adipose-derived regenerative cells (e.g., a cell population that comprises adipose-derived stem cells, and/or endothelial cells and/or progenitor cells) present in the lipo-digestate or concentrated population of adipose-derived cells from the second portion. One portion can be processed as described below to release or liberate the adipose-derived regenerative cells (e.g., a cell population that comprises adipose-derived stem cells, and/or endothelial cells and/or progenitor cells) from the connective tissue matrix to obtain a lipo-digestate, or concentrated population of adipose-derived cells comprising regenerative cells or stem cells. In some embodiments, two different units of adipose tissue are collected, e.g., from the same or different regions of the subject, or from different subjects. One unit can be processed as described below to obtain lipo-digestate or a concentrated population of adipose-derived cells comprising regenerative cells or stem cells, and the other unit can serve as the foundation for the fat graft that is supplemented with adipose-derived regenerative cells (e.g., lipo-digestate and/or a cell population that comprises adipose-derived stem cells, and/or endothelial cells and/or progenitor cells). In one embodiment one or both of the units of adipose tissue may be cryopreserved such that delivery of the graft to the patient may be separated in time from harvest of the tissue. In one such embodiment one or both units of tissue may be cryopreserved within the device or system of the present invention wherein the chambers of the device are fabricated from materials that retain mechanical and structural integrity during the processes of cryopreservation, cryostorage, thawing, and subsequent use as described herein. In another such embodiment the lipodigestate or concentrated population of adipose-derived cells comprising regenerative cells including adipose derived stem cells may be cryopreserved prior to use in fortification of the graft or implant as described herein.

The term "dried," as used in reference to "dried adipose tissue," refers to a unit of adipose tissue having a lower content of liquid, e.g., water or other liquid (e.g., tumescent fluid), present in the "dried adipose tissue" as compared to unprocessed adipose tissue from the same site and same subject (e.g., an equivalent unit (w/w) of adipose tissue taken from the same site and same subject as the adipose tissue that was dried). The term "dehydrated," as used in reference to "dehydrated adipose tissue," refers to a unit of adipose tissue having a lower content of liquid, e.g., water or other liquid (e.g., tumescent fluid), present in the "dried adipose tissue" as compared to unprocessed adipose tissue from the same site and same subject (e.g., an equivalent unit (w/w) of adipose tissue taken from the same site and same subject as the adipose tissue that was dried).

The term "equivalent unit" as used herein can refer to an equivalent volume or weight of adipose tissue obtained from a subject. For example, an equivalent unit can mean an equivalent volume (or weight) of adipose tissue obtained from a subject. In some embodiments, an equivalent unit can mean an equivalent volume (or weight) obtained from the same site (e.g., buttocks, abdomen, thigh, back, or the like) from the same or a different subject.

"Unprocessed adipose tissue" refers to adipose tissue that has not been partially or fully disaggregated, i.e., by subjecting the tissue to mechanical and/or enzymatic disaggregation. As such, unprocessed tissue contains intact tissue fragments, that include connective tissue bound to adipose-derived regenerative cells. As used herein, "adipose-derived regenerative cell" refers to any cells obtained from adipose tissue which cause or contribute to complete or partial regeneration, restoration, or substitution of structure or function of an organ, tissue, or physiologic unit or system to thereby provide a therapeutic, structural or cosmetic benefit. Examples of regenerative cells include: adipose-derived stem cells ("ADSCs"), endothelial cells, endothelial precursor cells, endothelial progenitor cells, macrophages, fibroblasts, pericytes, smooth muscle cells, preadipocytes, differentiated or de-differentiated adipocytes, keratinocytes, unipotent and multipotent progenitor and precursor cells (and their progeny), and lymphocytes.

In some embodiments, dried or dehydrated adipose tissue has about 1%, 2%, 3%, 4%, 5%, 6%, 7%, 8%, 9%, 10%, 12%, 15%, 20%, 25%, 30%, 35% 40%, 45%, 50%, 55%, 60%, 65%, 70%, 75%, 80%, 85%, 90%, or 95% (or any % in between this range) of the liquid content (as measured by volume and/or weight), of an equivalent unit of unprocessed adipose tissue. For example, dried adipose tissue can have greater than or equal to about 1.5 times, 2 times, 3 times, 4 times, 5 times, 6 times, 7 times, 8 times, 9 times, or 10 times (or any number in between this range) less liquid content than an equivalent unit of unprocessed adipose tissue. Similarly, the term "dehydrated," as used in reference to "dehydrated adipose tissue," refers to a lower content of water present in the "dehydrated adipose tissue," as compared to unprocessed adipose tissue, or an equivalent unit of unprocessed adipose tissue. In some embodiments, dehydrated adipose tissue can have greater than or equal to about 1%, 2%, 3%, 4%, 5%, 6%, 7%, 8%, 9%, 10%, 12%, 15%, 20%, 25%, 30%, 35% 40%, 45%, 50%, 55%, 60%, 65%, 70%, 80%, 90% or 95% (or any % in between this range) of the water content of an equivalent unit of unprocessed adipose tissue, or an equivalent unit of adipose tissue prepared by a centrifugation or another conventional approach. For example, dried adipose tissue can have greater than or equal to about 1.5 times, 2 times, 3 times, 4 times, 5 times, 6 times, 7 times, 8 times, 9 times, or 10 times (or any number in between this range) less water content than an equivalent unit of unprocessed adipose tissue.

In some embodiments, "dried" or "dehydrated" adipose tissue described herein can contain a lower content or percentage of lipid and/or red or white blood cells compared to an equivalent unit of unprocessed adipose tissue. In some embodiments, dried or dehydrated adipose tissue can have at less than about 1%, 2%, 3%, 4%, 5%, 6%, 7%, 8%, 9%, 10%, 12%, 15%, 20%, 25%, 30%, 35% 40%, 45%, 50%, 55%, 60%, 65%, 70%, 80%, 90%, 95% or 99% (or any % in between this range) (or any number in between this range) of the white blood cells in an equivalent unit of unprocessed adipose tissue and/or an equivalent unit of adipose tissue processed using a centrifugation method, e.g., wherein the excised tissue is spun in a fixed angle centrifuge or another conventional preparation technique. For example, in some embodiments, dried or dehydrated adipose tissue can contain less than about 75%, less than 80%, less than 85%, less than 90%, less than 95%, or less, or any % in between this range, of the number of white blood cells in an equivalent unit of adipose tissue.

In some embodiments, the dried or dehydrated adipose tissue provided herein can have at less than about 1%, 2%, 3%, 4%, 5%, 6%, 7%, 8%, 9%, 10%, 12%, 15%, 20%, 25%, 30%, 35% 40%, 45%, 50%, 55%, 60%, 65%, 70%, 80%, 90% or 95% (or any % in between this range) (or any number in between this range) of the red blood cells in an equivalent unit of unprocessed adipose tissue, or adipose tissue prepared using a centrifugation method, e.g., wherein the excised tissue is spun in a fixed angle centrifuge, or by another conventional preparative approach. For example, in some embodiments, the adipose tissue grafts produced in the systems disclosed herein contain less than about 75%, less than 80%, less than 85%, less than 90%, less than 95%, or less, or any % in between this range, of the number of red blood cells in an equivalent unit of adipose tissue.

In some embodiments, the dried or dehydrated adipose tissue grafts disclosed herein have less than about 1%, 2%, 3%, 4%, 5%, 6%, 7%, 8%, 9%, 10%, 12%, 15%, 20%, 25%, 30%, 35% 40%, 45%, 50%, 55%, 60%, 65%, 70%, 80%, 90% or 95% (or any % in between this range) (or any number in between this range) of lipid in an equivalent unit of unprocessed adipose tissue, or adipose tissue prepared by a conventional centrifugation protocol, e.g., wherein the excised adipose tissue is spun in a fixed angle centrifuge. For example, in some embodiments, the dried or dehydrated adipose tissue grafts disclosed herein contain less than about 75%, less than 80%, less than 85%, less than 90%, less than 95%, or less, or any % in between, of the percentage of free lipid content present in an equivalent unit of unprocessed adipose tissue.

In some embodiments, dried or dehydrated adipose tissue is obtained by providing unprocessed adipose tissue in a device that includes a filter and a separator, as described in further detail below. The filter can divide the device into two internal chambers, thereby defining a first chamber and a second chamber or subsystem. The adipose tissue is introduced into the first chamber or subsystem of the device, and preferably does not enter into the second chamber of the device. The filter has a plurality of pores, that allow for the free flow of liquid such as, water, tumescent fluid, wash solution, (e.g., Lactated Ringers, saline, PLASMALTYE™ and the like), free lipid, oil, blood cells, lysed cells from the adipose tissue and blood components, into the second chamber, but the pore size is such that it retains non-disaggregated adipose tissue and tissue fragments in the first chamber. The second chamber can include a separator made from material that is lipid-wicking and/or fluid-wicking (e.g., a meshwork design that draws fluid from the first chamber), as described in further detail below. In preferred embodiments, the separator is made from a porous material, wherein the pores of the separator are larger than the pores of the filter.

The unprocessed adipose tissue within the first chamber is rinsed or washed with a physiologic wash solution. In preferred embodiments, the physiologic wash solution is aseptically introduced into the device. In some embodiments, the wash solution is introduced into the first chamber. In some embodiments, the wash solution is introduced into the second chamber, and passes through the filter into the second chamber, thereby coming in contact with the adipose tissue therein. In some embodiments, the wash solution is introduced into both the first and the second chambers.

In some embodiments, the adipose tissue and the wash solution are agitated (e.g., by inverting, squeezing, or rocking the device gently), in order to facilitate the rinsing and separation of free lipid, red and white blood cells, and tumescent fluid from the adipose tissue in the first chamber. In other embodiments, the adipose tissue within the first chamber is contacted with the wash solution, which is allowed to drain or be drawn from the first chamber of the device without agitation, e.g., by gravitational or wicking forces.

In some embodiments, the volume of wash solution used to rinse the adipose tissue can be greater than the volume of the adipose tissue. By way of example only, in some embodiments, greater than or equal to about 1 ml, 2 ml, 3 ml, 4 ml, 5 ml, 6 ml, 7 ml, 8 ml, 9 ml, 10 ml, 15 ml, 20 ml, 25 ml, 30 ml, 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml, 1000 ml 1100 ml, 1500 ml, 2000 ml or any amount in between these volumes, of wash solution can be used to rinse the unprocessed adipose tissue.

During the washing or rinsing step, liquid, e.g. wash solution, free lipid, oil, blood cells, lysed cells from the adipose tissue and blood components, and the like pass through the pores of the filter between the first and second chambers of the device. As such, the second chamber becomes filled with liquid. The separator within the second chamber can function to draw and retain fluid from the first chamber into the second chamber, e.g., acting as a wick. The movement of water, tumescent fluid, blood and free lipid from the first chamber, which houses the adipose tissue, dries and dehydrates the adipose tissue. The fluid is removed from the second chamber through a port. In some embodiments, fluid is removed from the second chamber using a pump or a vacuum. In some embodiments, fluid is allowed to drain from the port leaving the second chamber.

Exemplary devices for making dried or dehydrated adipose tissue, as well as, supplemented or fortified adipose tissue grafts are discussed in further detail below, with reference to FIGS. 2-13.

In some embodiments, the steps of adding wash solution and removing contents from the second chamber is repeated 1 time, 2 times, 3 times, 4 times, 5 times, 6 times, 7 times, 8 times, 9 times, 10 times or more.

The dried or dehydrated adipose tissue can be removed (preferably aseptically) from the first chamber, and administered to a subject directly. In some embodiments, the dried or dehydrated adipose tissue is processed further (e.g., by the addition of an additive, as described in further detail below), prior to administration to a subject.

Supplemented Adipose Tissue Grafts

Described herein are methods and systems for producing supplemented, enhanced, or fortified adipose tissue grafts, e.g., wherein the graft is unprocessed adipose tissue or dried or dehydrated adipose tissue. For example, in some methods described herein, the fortified or supplemented adipose tissue grafts are supplemented with additional adipose-derived regenerative cells or adipose-derived stem cells, e.g., with lipo-digestate or a concentrated adipose-derived cell population comprising regenerative cells or stem cells. Preferably, the additional adipose-derived regenerative cells or adipose-derived stem cells are obtained from the same subject. In some embodiments, the additional adipose-derived regenerative cells or adipose derived stem cells can be from a different subject.

By some of the methods described herein, for example, digested lipoaspirate ("lipo-digestate") is applied directly onto unprocessed adipose tissue, dried adipose tissue, dehydrated adipose tissue, or unprocessed adipose tissue matrix, and the unprocessed adipose tissue, dried adipose tissue, dehydrated adipose tissue, or unprocessed adipose tissue matrix is used as a filter or sieve to retain components present in the lipo-digestate (e.g., adipose-derived regenerative cells, such as a cell population that comprises adipose-derived stem cells and/or endothelial cells and/or progenitor cells). By this process, one can rapidly prepare an adipose tissue graft, implant, or fat graft that has been enriched, supplemented or fortified with said adipose-derived regenerative cells (e.g., a cell population that comprises adipose-derived stem cells, and/or endothelial cells and/or progenitor cells), without additional purification or isolation steps, which may be cumbersome, time consuming, and may have an impact on cell viability. By some of the methods described herein, for example, concentrated populations of adipose-derived cells comprising regenerative cells or stem cells is applied directly onto unprocessed adipose tissue, dried adipose tissue, dehydrated adipose tissue, or unprocessed adipose tissue matrix, and the unprocessed adipose tissue, dried adipose tissue, dehydrated adipose tissue.

In contrast to existing approaches to isolate, purify, and concentrate adipose-derived regenerative cells, some methods disclosed herein use the intact matrix of the unprocessed adipose tissue, dried adipose tissue, or dehydrated adipose tissue to gently filter and concentrate the adipose-derived regenerative cells in situ, that is, on the matrix itself and by doing so avoid the cell damage brought about by centrifugation, membrane, gel, or gradient, filtration and other mechanical manipulations of lipo-digestate. Additionally, the approach described herein promotes an even or substantially complete distribution of the exogenous adipose-derived regenerative cells (e.g., a cell population that comprises adipose-derived stem cells, and/or endothelial cells and/or progenitor cells) throughout the adipose tissue graft.

As used herein, "regenerative cell composition" or "lipo-digestate" refers to the composition of cells typically present in a volume of liquid after a tissue, e.g., adipose tissue, is washed and at least partially disaggregated. For example, in some embodiments, a regenerative cell composition or lipo-digestate can comprise a cell solution that comprises a population of adipose-derived cells that comprises adipose-derived regenerative cells, e.g., stem cells. In some embodiments, regenerative cell compositions can include multiple different types of regenerative cells, including ADSCs, endothelial cells, endothelial precursor cells, endothelial progenitor cells, macrophages, fibroblasts, pericytes, smooth muscle cells, preadipocytes, differentiated or de-differentiated adipocytes, keratinocytes, unipotent and multipotent progenitor and precursor cells (and their progeny), and lymphocytes. In some embodiments, regenerative cell compositions include only one, only two, only three, only four or more, types of regenerative cells. Regenerative cell compositions and lipo-digestates can, in some embodiments, also contain one or more contaminants, such as collagen, which may be present in the tissue fragments. In some embodiments, the lipo-digestate, or regenerative cell solution, is substantially free of intact adipose tissue fragments.

As used herein, "stem cell" refers to a multipotent regenerative cell with the potential to differentiate into a variety of other cell types, which perform one or more specific functions and have the ability to self-renew. Some of the stem cells disclosed herein may be pluripotent.

As used herein, "progenitor cell" refers to a multipotent regenerative cell with the potential to differentiate into more than one cell type. "Progenitor cell", as used herein, also refers to a unipotent regenerative cell with the potential to differentiate into only a single cell type, which performs one or more specific functions and has limited or no ability to self-renew. In particular, as used herein, "endothelial progenitor cell" refers to a multipotent or unipotent cell with the potential to differentiate into vascular endothelial cells.

As used herein, "precursor cell" refers to a unipotent regenerative cell with the potential to differentiate into one cell type. Precursor cells and their progeny may retain extensive proliferative capacity, e.g., lymphocytes and endothelial cells, which can proliferate under appropriate conditions.

As used herein "stem cell number" or "stem cell frequency" refers to the number of colonies observed in a clonogenic assay in which adipose derived cells (ADC) are plated at low cell density (<10,000 cells/well) and grown in growth medium supporting MSC growth (for example, DMEM/F12 medium supplemented with 10% fetal calf serum, 5% horse serum, and antibiotic/antimycotic agents. Cells can be grown for two weeks after which cultures can be stained with hematoxylin. Colonies of more than 50 cells are counted as CFU-F. Stem cell frequency is calculated as the number of CFU-F observed per 100 nucleated cells plated (for example; 15 colonies counted in a plate initiated with 1,000 nucleated ADC cells gives a stem cell frequency of 1.5%). Stem cell number is calculated as stem cell frequency multiplied by the total number of nucleated ADC cells obtained. A high percentage (~100%) of CFU-F grown from ADC cells express the cell surface molecule CD105 which is also expressed by marrow-derived stem cells (Barry et al., 1999). CD105 is also expressed by adipose tissue-derived stem cells (Zuk et al., 2002). In some embodiments, adipose tissue can be processed according to the methods described herein to obtain lipo-digestate, and/or a concentrated population of adipose-derived cells, wherein at least 0.2%, 0.3%, 0.4%, 0.5%, 0.6%, 0.7%, 0.8%, 0.9%, 1.0%, 2%, 3%, 4%, 5%, 6%, 7% 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 96%, 97%, 98%, 99%, or 100% of the cells are stem cells or other type of regenerative cells of the lipo-digestate or concentrated adipose-derived cell population.

Preferably, adipose tissue is processed to produce lipo-digestate or a regenerative cell solution in a sterile, closed system, with a closed fluid/tissue pathway, to avoid any contact with the external environment and eliminate the possibility of contamination from the environment. Devices useful for processing adipose tissue and producing lipo-digestate are known in the art. In preferred embodiments, adipose tissue is processed to produce lipo-digestate while maintaining a completely closed system using, for example, in some embodiments, a device as described in U.S. Pat. No. 7,390,484, which is hereby expressly incorporated by reference in its entirety. In some preferred embodiments, the adipose tissue processing procedure does not include centrifugation, elutriation, or any other mechanical approaches for concentrating the cell population comprising adipose-derived regenerative cells, which causes or has the potential to cause decreased viability of the regenerative cells in the regenerative cell composition/lipo-digestate.

In some embodiments, the process to obtain lipo-digestate includes the removal or depletion of the tissue of the mature fat-laden adipocyte component from the portion or unit of adipose tissue used to produce the lipo-digestate or concentrated adipose-derived cell populations. In some embodiments, the adipose tissue is subjected to a series of washing and disaggregation steps in which the tissue is first rinsed to reduce the presence of free lipids (released from ruptured adipocytes) and peripheral blood elements (released from blood vessels severed during tissue harvest). For example, in some embodiments, the adipose tissue is mixed with isotonic saline, e.g., phosphate buffered saline, or other physiologic solution(s) (e.g., PLASMALYTE®, of Baxter Inc., NORMOSO® of Abbott Labs, or Lactated Ringers solution). The washed tissue can then be disaggregated to free intact adipocytes and other cell populations from the connective tissue matrix. In certain embodiments, the entire adipocyte component, or non-regenerative cell component, is separated from the regenerative cell component of the adipose tissue. In other embodiments, only a portion or portions of the adipocyte component is separated from the regenerative cells. Intact adipose tissue fragments can be separated from the free lipid and cells by several approaches including, but not limited to, filtration, decantation, or sedimentation, or the like. Preferably, the digested tissue is not subjected to centrifugation or elutriation.

In some embodiments, the adipose tissue used to generate the lipo-digestate is fully disaggregated, whereas in other embodiments, it is only partially disaggregated. Intact adipose tissue fragments, e.g., from unprocessed or washed adipose tissue, can be disaggregated using any conventional techniques or methods, including mechanical force (mincing or shear forces), enzymatic digestion with single or combinatorial proteolytic enzymes, such as collagenase, trypsin, lipase, liberase HI, as disclosed in U.S. Pat. No. 5,952,215, and pepsin, or a combination of mechanical and enzymatic methods. Additional methods using collagenase that may be used to disaggregate adipose tissue are disclosed in U.S. Pat. Nos. 5,830,714 and 5,952,215, and by Williams, S. K., S. McKenney, et al. (1995). "Collagenase lot selection and purification for adipose tissue digestion." *Cell Transplant* 4(3): 281-9. In some embodiments, neutral proteases can be used to disaggregate tissue, instead of or in addition to, collagenase, as disclosed in Twentyman, P. R. and J. M. Yuhas (1980). "Use of bacterial neutral protease for disaggregation of mouse tumours and multicellular tumor spheroids." *Cancer Lett* 9(3): 225-8. In some embodiments, adipose tissue is disaggregated with a combination of enzymes, such as a combination of collagenase and trypsin, as disclosed in Russell, S. W., W. F. Doe, et al. (1976). "Inflammatory cells in solid murine neoplasms. Tumor disaggregation and identification of constituent inflammatory cells." *Int J Cancer* 18(3): 322-30. In some embodiments, adipose tissue can be disaggregated using a combination of an enzyme, such as trypsin, and mechanical dissociation, as disclosed in Engelholm, S. A., M. Spang-Thomsen, et al. (1985). "Disaggregation of human solid tumours by combined mechanical and enzymatic methods." *Br J Cancer* 51(1): 93-8.

In some embodiments, a portion of the adipose tissue is fully disaggregated, to separate the adipose-derived regenerative cells (e.g., adipose-derived stem cells) from the mature adipocytes and connective tissue. In some embodiments, a portion of the adipose tissue is only partially disaggregated. For example, partial disaggregation may be performed with one or more enzymes, which are removed from the at least a part of the adipose tissue early, relative to an amount of time that the enzyme would otherwise be left thereon to fully disaggregate the portion of the adipose tissue. Such a process may require less processing time.

In some embodiments, a portion or unit of adipose tissue is washed with sterile buffered isotonic saline and incubated with collagenase at a collagenase concentration, temperature, and time sufficient to provide adequate disaggregation. Preferably, enzymes used for disaggregation are approved for human use by the relevant authority (e.g., the U.S. Food and Drug Administration), and are free from microorganisms and contaminants, such as endotoxin. Suitable collagenase preparations include recombinant and non-recombinant collagenase. Non-recombinant collagenase may be obtained from F. Hoffmann-La Roche Ltd, Indianapolis, Ind. and/or Advance Biofactures Corp., Lynbrook, N.Y. Recombinant collagenase may also be obtained as disclosed in U.S. Pat. No. 6,475,764.

By way of example, in some embodiments, the adipose tissue is treated with collagenase solutions with from about 0.5 μg/ml to about 100 μg/ml, e.g., 10 μg/ml to about 50 μg/ml collagenase, and are incubated at from about 30° C. to about 38° C. for from about 20 minutes to about 60 minutes. These parameters will vary according to the source of the collagenase enzyme, optimized by empirical studies, in order to validate that the system is effective at extracting the desired cell populations in an appropriate time frame. For example, in some embodiments, the tissue is incubated with a solution comprising collagenase for 10-15 minutes, at about 37° C.

Following disaggregation the lipo-digestate can be washed/rinsed to remove additives and/or by-products of the disaggregation process, e.g., collagenase and/or other enzymatic disaggregation agents, and newly-released free lipid.

In some embodiments, the lipo-digestate can be applied to a portion of unprocessed, dried, or dehydrated adipose tissue under conditions that allow the lipo-digestate to permeate through the unprocessed, dried, or dehydrated adipose tissue. For example, in some embodiments, the lipo-digestate can be resuspended, layered over (or under) a portion of unprocessed adipose tissue, dried adipose tissue or dehydrated adipose tissue and the lipo-digestate is filtered through the unprocessed adipose tissue (or dried or dehydrated adipose tissue) using gravitational forces. In some embodiments, the lipo-digestate is pumped through the unprocessed adipose tissue, for example using a peristaltic pump, vacuum or the like. In some embodiments, the lipo-digestate is added to the unprocessed adipose tissue to create a mixture, and the mixture is agitated or rocked, either mechanically or manually. As the lipo-digestate is filtered through or mixed with the unprocessed adipose tissue, adipose-derived regenerative cells can become bound by the connective tissue matrix, and saline and other fluids, flow through the tissue, thereby producing a fat graft or implant supplemented or enhanced with adipose-derived regenerative cells (e.g., adipose-derived regenerative cell comprising stem cells). In some embodiments, the flow-through, e.g., saline, mature adipocytes, red blood cells, and the like is removed to a waste container. Systems and devices for generating supplemented adipose tissue grafts are discussed in more detail below, and one embodiment of the method is depicted in the schematic shown in FIG. 1.

FIG. 1 shows a schematic of an exemplary pathway for preparing a supplemented adipose-tissue graft. In the first step, a unit of adipose tissue is provided into a closed/sterile container (e.g., a collapsible, flexible bag or a rigid container as described elsewhere herein), via an inlet. The adipose tissue is rinsed/washed and digested within the container while maintaining a closed system, as described herein. In the embodiment shown in FIG. 1, the first container has an inlet and an outlet. The first container shown in FIG. 1 shows a single inlet and a single outlet, however, the skilled artisan will appreciate that devices described herein can include multiple, i.e., 1, 2, 3, 4, 5, 6, 7, 8, 9, 10, or more inlets and outlets. Preferably, the inlet(s) and the outlet(s) are configured for aseptic addition and/or removal of contents (e.g., tissue, additives, solutions, and the like) in the first container.

In the embodiment disclosed in FIG. 1, a second unit of adipose tissue, or portion of the first unit of adipose tissue is provided in a second container (e.g., a collapsible, flexible bag or a rigid container, as described elsewhere herein). In the embodiment shown in FIG. 1, the second container has an inlet, or inlets and an outlet or outlets. The inlet of the second container is configured for the addition of contents (e.g., lipo-digestate or concentrated populations of adipose-derived cells) into the container, preferably while maintaining a closed sterile fluid pathway. The outlet is configured for the removal of contents, e.g., excess wash solution, free lipid, blood, and the like from the second container.

In the embodiment shown in FIG. 1, following digestion, the lipo-digestate and non-disaggregated adipose tissue fragments, and free lipid form different layers within the first container. The lipo-digestate layer is allowed to exit (e.g., via a pump or vacuum as shown in FIG. 1) through an outlet in the closed container, and to enter, e.g., through a conduit that maintains the closed system, into a separate container that contains unprocessed or washed, dried or dehydrated adipose tissue. The lipo-digestate from the first container mixed with the unprocessed, dried or dehydrated adipose tissue under conditions that allow the separated adipose-derived regenerative cells in the lipo-disgestate or concentrated adipose-derived cell population to permeate through the adipose tissue. In FIG. 1, the regenerative cells are pumped through the unprocessed or dried adipose tissue to create the supplemented adipose tissue graft.

In some embodiments, any excess lipo-digestate or concentrated adipose-derived cell solution is recirculated through the unprocessed, dried or dehydrated adipose tissue in the second container, by providing an aseptic loop in the second container, wherein the excess regenerative cell solution or lipo-digestate drains through an exit port (outlet) into a conduit that leads to an entry port (inlet) in the container housing the adipose tissue.

It will be appreciated that in making the fortified or supplemented adipose tissue grafts described herein, the volumes of the various units or portions of adipose tissue used to produce the lipo-digestate or concentrated adipose-derived cell solutions and to serve as the base or foundation for the adipose tissue graft that is supplemented with the adipose-derived regenerative cells or lipo-digestate may be equal, or they may be different. For example, the volume of adipose tissue used to make the lipo-digestate can be at least, greater than or equal to about 10%, 20%, 30%, 40%, 50%, 60%, 70%, 80%, 90%, 100%, 110%, 120%, 130%, 140%, 150%, 160%, 170%, 180%, 190%, 200, 210%, 220%, 230%, 240%, 250%, 260%, 270%, 280%, 290%, 300%, or any number in between this range, more than the volume of another unit of adipose tissue. In some embodiments, the volume of adipose tissue used to make the lipo-digestate can be at least, greater than or equal to about 10%, 20%, 30%, 40%, 50%, 60%, 70%, 80%, 90%, 100%, 110%, 120%, 130%, 140%, 150%, 160%, 170%, 180%, 190%, 200, 210%, 220%, 230%, 240%, 250%, 260%, 270%, 280%, 290%, 300%, or any number in between this range, less than the volume of another unit of adipose tissue. In some embodiments, the ratio of lipo-digestate:graft tissue is about 0.25:1, 0.5:1, 0.75:1, 1:1, 1.25:1, 1.5:1, 1.75:1 or 2:1, or any number in between this range. Preferably, the ratio of lipo-digestate:graft tissue less than about 1:1, such as 0.5:1 or 0.25:1.

In some embodiments, the portion of processed adipose tissue (e.g., digested lipoaspirate, or regenerative cell solution), and/or a portion of unprocessed adipose tissue, dried adipose tissue, dehydrated adipose tissue, and/or a adipose tissue graft supplemented with adipose-derived regenerative cells described herein can be combined, fortified, supplemented, enhanced, or mixed with additives such as other cells, tissue, tissue fragments, demineralized bone, or factors or agents, such as additives that lyse adipocytes and/or red blood cells. For example, in some embodiments, the portion of processed adipose tissue, and/or a portion of unprocessed adipose tissue (or dried or dehydrated adipose tissue), and/or a adipose tissue graft supplemented with adipose-derived regenerative cells described herein can be combined, supplemented, or mixed with growth factor additives such as insulin or drugs such as members of the thiaglitazone family, antibiotics, biologically active or inert compounds, such as coagulases, cell-reaggregation inhibitors, resorbable plastic scaffolds, or other additive intended to enhance the delivery, efficacy, tolerability, or function of the population.

In certain embodiments, the unprocessed adipose tissue, the dried adipose tissue, the dehydrated adipose tissue, the lipo-digestate, and/or the supplemented adipose tissue grafts can be supplemented with one or more cellular differentiation agent additives, such as cytokines and growth factors. In some embodiments, the subject receiving the adipose tissue graft is provided one or more cellular differentiation agents, such as cytokines and growth factors separately, i.e., in a different composition, from the adipose tissue graft. For example, in some embodiments, the compositions are supplemented with anigiogenic agents, or factors. In some embodiments, the unprocessed adipose tissue, the dried adipose tissue, the dehydrated adipose tissue, the lipo-digestate, and/or supplemented adipose grafts described herein are provided an angiogenic factor(s) as an additive. As used herein, the term "angiogenesis" refers to the process by which new blood vessels are generated from existing vasculature and tissue (Folkman, 1995). As used herein, the term "angiogenic factor" or "angiogenic protein" refers to any known protein, peptide or other agent capable of promoting growth of new blood vessels from existing vasculature ("angiogenesis"). Suitable angiogenic factors for use in the invention include, but are not limited to, Placenta Growth Factor (Luttun et al., 2002), Macrophage Colony Stimulating Factor (Aharinejad et al., 1995), Granulocyte Macrophage Colony Stimulating Factor (Buschmann et al., 2003), Vascular Endothelial Growth Factor (VEGF)-A, VEGF-A, VEGF-B, VEGF-C, VEGF-D, VEGF-E (Mints et al., 2002), neuropilin (Wang et al., 2003), fibroblast growth factor (FGF)-1, FGF-2(bFGF), FGF-3, FGF4, FGF-5, FGF-6 (Botta et al., 2000), Angiopoietin 1, Angiopoietin 2 (Sundberg et al., 2002), erythropoietin (Ribatti et al., 2003), BMP-2, BMP4, BMP-7 (Carano and Filvaroff, 2003), TGF-beta (Xiong et al., 2002), IGF-1 (Shigematsu et al., 1999), Osteopontin (Asou et al., 2001), Pleiotropin (Beecken et al., 2000), Activin (Lamouille et al., 2002), Endothelin-1 (Bagnato and Spinella, 2003) and combinations thereof. Angiogenic factors can act independently, or in combination with one another. When in combination, angiogenic factors can also act synergistically, whereby the combined effect of the factors is greater than the sum of the effects of the individual factors taken separately. The term "angiogenic factor" or "angiogenic protein" also encompasses functional analogues of such factors. Functional analogues include, for example, functional portions of the factors. Functional analogues also include anti-idiotypic antibodies which bind to the receptors of the factors and, thus, mimic the activity of the factors in promoting angiogenesis. Methods for generating such anti-idiotypic antibodies are well known in the art and are described, for example, in WO 97/23510, the contents of which are expressly incorporated by reference in its entirety.

Angiogenic factors useful in the embodiments disclosed herein can be produced or obtained from any suitable source. For example, the factors can be purified from their native sources, or produced synthetically or by recombinant expression. The factors can be administered to subjects as a protein composition, in the form of an expression plasmid encoding the factors, or mixed in with the compositions disclosed herein. The construction of suitable expression plasmids is well known. Suitable vectors for constructing expression plasmids, include, for example, adenoviral vectors, retroviral vectors, adeno-associated viral vectors, RNA vectors, liposomes, cationic lipids, lentiviral vectors and transposons.

In some embodiments, the cells of the processed adipose tissue, e.g., lipo-digestate, or regenerative cell solution, the cells of the unprocessed adipose tissue, the dried adipose tissue, the dehydrated adipose tissue, or the cells of the supplemented adipose tissue grafts described herein can also be modified by insertion of DNA or by placement in cell culture in such a way as to change, enhance, or supplement the function of the compositions for derivation of a cosmetic, structural, or therapeutic purpose. For example, gene transfer techniques for stem cells are known by persons of ordinary skill in the art, as disclosed in Mosca, J. D., J. K. Hendricks, et al. (2000). "Mesenchymal stem cells as vehicles for gene delivery." Clin Orthop (379 Suppl): S71-90, and may include viral transfection techniques, and more specifically, adeno-associated virus gene transfer techniques, as disclosed in Walther, W. and U. Stein (2000). "Viral vectors for gene transfer: a review of their use in the treatment of human diseases." Drugs 60(2): 249-71, and Athanasopoulos, T., S. Fabb, et al. (2000). "Gene therapy vectors based on adeno-associated virus: characteristics and applications to acquired and inherited diseases (review)." Int J Mol Med 6(4): 363-75. Non-viral based techniques may also be performed as disclosed in Muramatsu, T., A. Nakamura, et al. (1998). "In vivo electroporation: a powerful and convenient means of nonviral gene transfer to tissues of living animals (Review)." Int J Mol Med 1(1): 55-62. In preferred embodiments, the cells of the processed tissue are not cultured. More preferably, the cells of the processed tissue are maintained within a closed, sterile system until their use, e.g., until they are either loaded onto a delivery device, combined with unprocessed or dried or dehydrated adipose tissue, or delivered directly into a subject.

In embodiments wherein the adipose tissue grafts are administered to a patient other than the patient from which the cells and/or tissue were obtained, one or more immunosuppressive agent additives may be administered to the patient receiving the graft to reduce, and preferably prevent, rejection of the transplant. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. patent Pub. No. 20020182211. Other examples include cyclosporin, myophenylate mofetil, rapamicin, and anti-thymocyte globulin.

The supplemented adipose tissue graft produced by the methods disclosed herein can be administered directly into the subject. As used herein, the terms "administering," "introducing," "delivering," "placement" and "transplanting" are used interchangeably herein and refer to the placement of the compositions disclosed herein, e.g., supplemented fat grafts, into a subject by a method or route which results in at least partial localization of the transplant or fat graft at a desired site. In some embodiments, the supplemented adipose tissue graft (e.g., the adipose graft supplemented adipose-derived regenerative cells) can be administered to the subject without being removed from the system or exposed to the external environment of the system or device in which it was generated prior to administration. Providing a closed system reduces the possibility of contamination of the material being administered to the subject. Thus, processing the adipose tissue and generating the supplemented adipose tissue graft while maintaining a closed system provides advantages over existing methods because the active cell population is more likely to be sterile. In such an embodiment, the only time the lipo-digestate or the supplemented adipose tissue graft are exposed to the external environment, or removed from the system, is when the cells or supplemented grafts are being withdrawn into an application device and being administered to the patient. In one embodiment, the application device can also be part of the closed system. Thus, in some embodiments, the lipo-digestate or supplemented adipose tissue grafts are not processed for culturing, or cryopreserved.

In some embodiments, at least a portion of the unprocessed tissue, the dried adipose tissue, the dehydrated adipose tissue, the lipo-digestate, and/or supplemented adipose tissue graft is stored for later implantation/infusion. For example, the compositions disclosed herein (i.e., the unprocessed tissue, dried adipose tissue, dehydrated adipose tissue, lipo-digestate, concentrated cell adipose-derived cell populations and/or supplemented adipose tissue graft) can be divided into more than one aliquot or unit such that part of the composition is retained for later application while part is applied immediately to the patient.

At the end of processing, the supplemented or fortified adipose tissue graft can be loaded into a delivery device, such as a syringe, scaffold, absorbable capsule or implant, for placement into the recipient by, for example subcutaneous techniques. In other words, the supplemented, enhanced, or fortified fat graft or implant may be placed into the patient by any means known to persons of ordinary skill in the art, for example, they may be introduced into the dermis (subcutaneous), into tissue space, or into tissues (e.g., breast, buttocks, or the like), or other location. Preferably, the loading takes place while maintaining a closed system. Preferred embodiments include placement by needle, catheter, or by direct surgical implantation in association with additives, such as a preformed matrix or absorbable breast-shaped capsules.

As used herein, the term "subject" includes warm-blooded animals, preferably mammals, including humans. In a preferred embodiment, the subject is a primate. In an even more preferred embodiment, the subject is a human.

Figure 2:
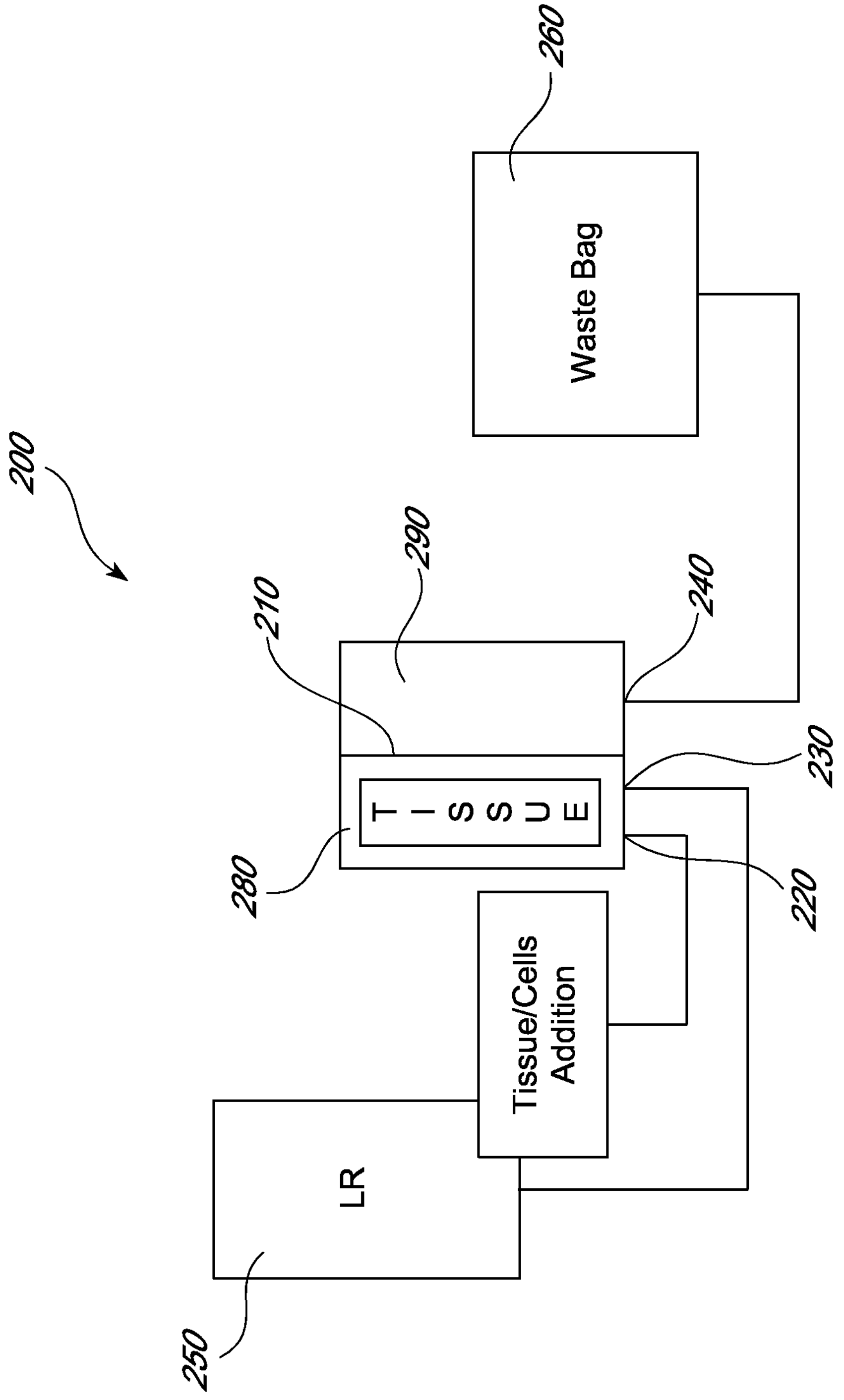
FIG. 2 shows a block diagram of a flexible collection container.

Devices for Producing Dried Adipose Tissue Grafts and Supplemented Adipose Tissue Grafts As discussed above, provided herein are devices and/or systems for making dried or dehydrated adipose tissue, and supplemented or fortified adipose tissue grafts. Turning to FIG. 2, shown is an exemplary system for the production of adipose tissue grafts suitable for supplementation with adipose-derived regenerative cells. The system comprises a flexible collection container 200, e.g., a medical grade collection bag, with a layer of filter mesh 210 that partitions the bag into a first 280 and a second internal chamber 290. In some embodiments, the filter can comprise a plurality of openings or pores that permit the passage of contents, e.g., mature adipocytes, red blood cells, saline, and the like, from the first internal chamber into the second internal chamber. Preferably the plurality of pores in the filter are greater than about 30 μm. For example, in some embodiments, the plurality of openings in the filter can be about greater than, less than, or equal to 30 μm, 35 μm, 40 μm, 50 μm 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, and 300 μm, or any number in between this range. For example, in some embodiments, the plurality of openings in the filter 210 can be between about 30 μm to about 500 μm. (e.g., about 60 μm-300 μm, such as 74 to about 265 μm).

In some embodiments, the first internal chamber 280 includes two ports 220, 230. In some embodiments, the second internal chamber 290 includes one port, 240. In some embodiments, the flexible collection container 200 comprises a wash container 250 for washing or rinsing solution, which is operably coupled to internal collection chamber 280 via port 220, to enable passage of solution from container 250 to internal chamber 280 through a closed fluid pathway. In some embodiments, port 240 is operably coupled to a waste bag 260, through which contents, such as red blood cells, saline, mature adipocytes and the like are removed from internal chamber 290.

In some embodiments, adipose tissue is added to the flexible collection chamber 200 though port 220. In some embodiments, a rinsing solution, such as Lactated Ringers solution, is added to the first internal chamber through port 230. The flexible collection container is then agitated or rocked, e.g., on a mechanical rocker, or other agitation device. Red blood cells, excess rinsing solution, lysed cells, and mature adipocytes and lipid are removed from the tissue present in the chamber 280.

In some embodiments, the system is configured to allow the aseptic addition of lipo-digestate to internal chamber 280, housing the rinsed adipose tissue. For example, the flexible collection container 200 may contain an additional port providing a sterile entry pathway into internal chamber 280, through which lipo-digestate can be directed.

Figure 3:
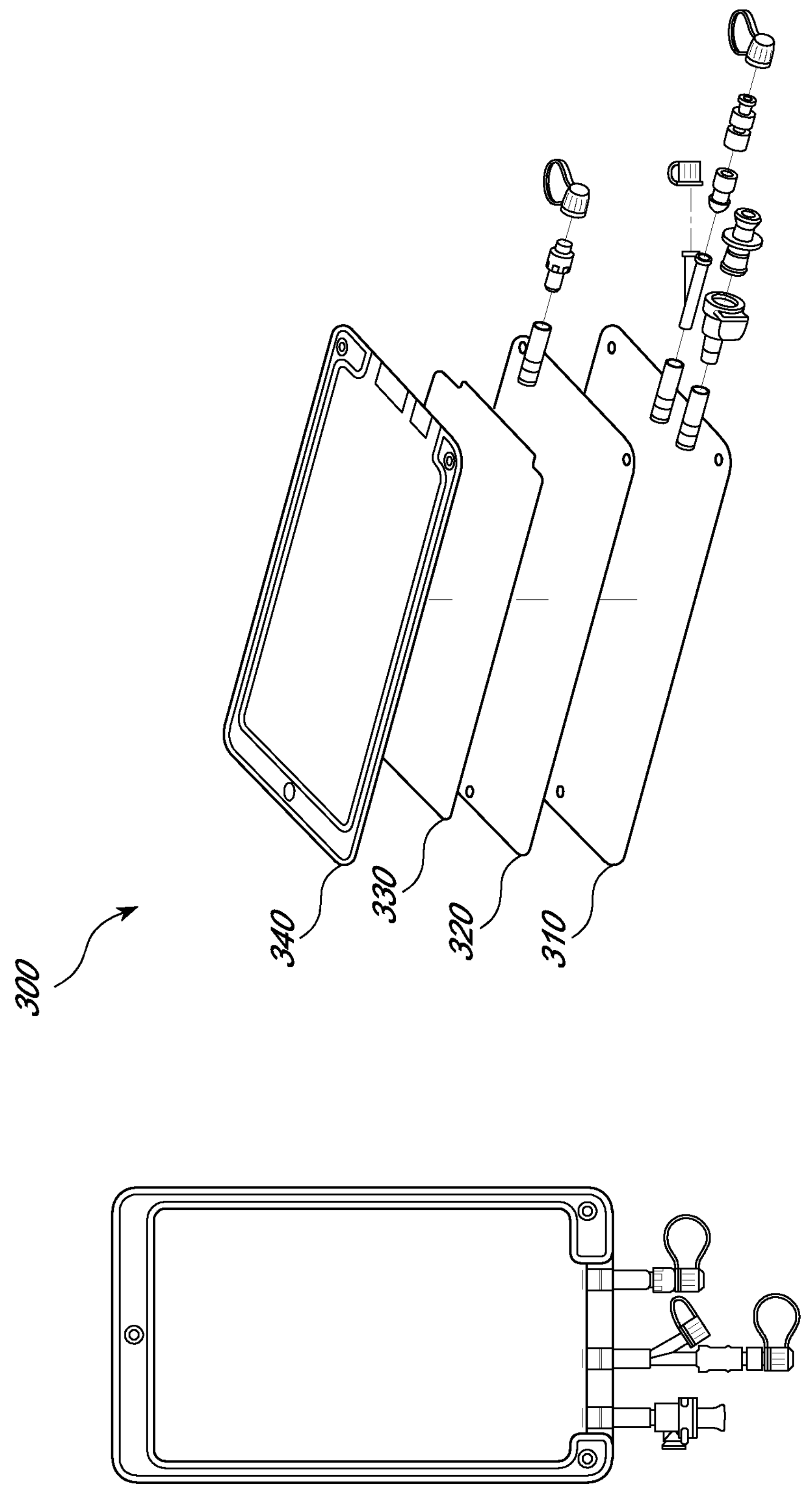
FIG. 3 illustrates an exemplary system used to optimize an adipose tissue graft. The graft may be supplemented with adipose derived regenerative cells.
Figure 4:
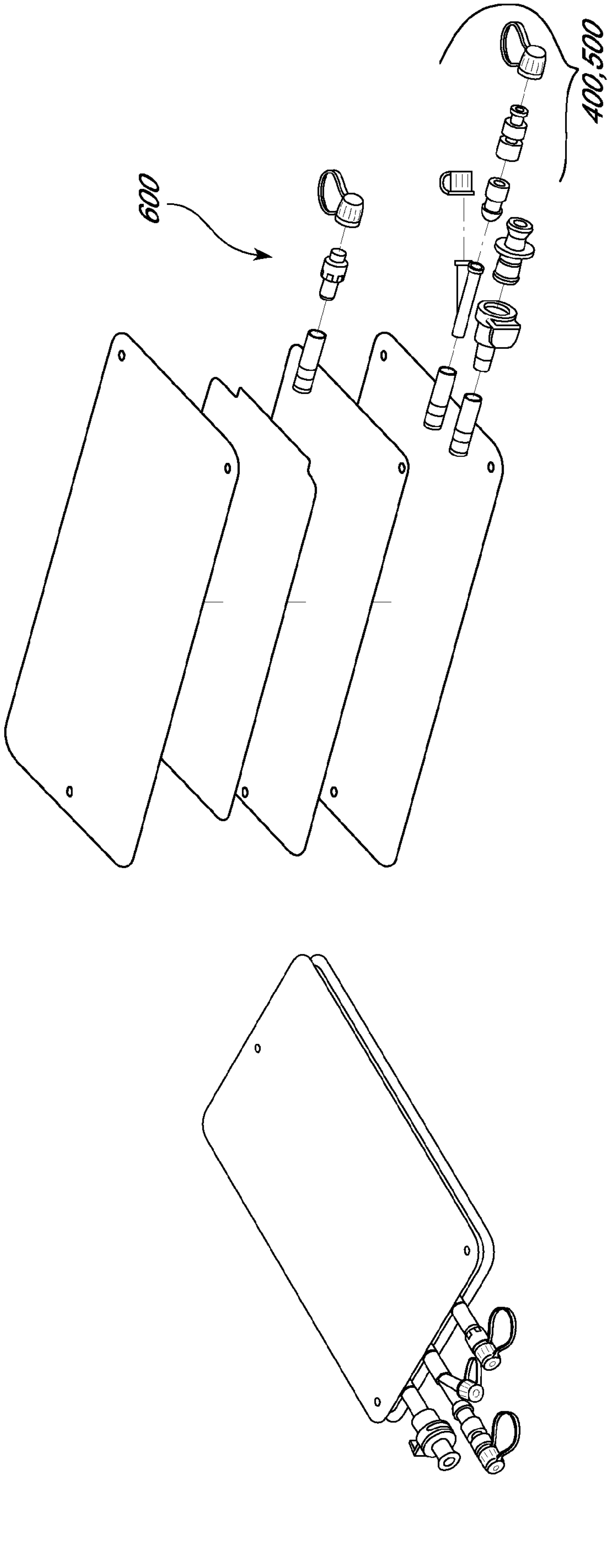
FIG. 4 illustrates ports and adaptors in system 300.

FIGS. 3-13 show additional embodiments of the systems disclosed herein for the production of optimized adipose tissue grafts. FIGS. 3 and 4 show an exemplary configuration of a system 300, which provides a closed, sterile process for controlling the hydration of an adipose tissue graft, e.g., to crate dried or dehydrated adipose tissue. For example, a common problem associated with preparing adipose tissue implants concerns the unpredictability of the behavior of the graft after implantation due to resorbtion or absorption of fluids from the grafted tissue into the body. As discussed below, the system 300 provides the operator with the ability to reduce this variability by creating a drier graft than that of conventionally obtained adipose tissue. Further, this drier adipose tissue graft or implant can be, optionally, supplemented with lipo-digestate (or concentrated adipose-derived cell populations comprising regenerative cells), or administered directly to a subject.

Figure 5:
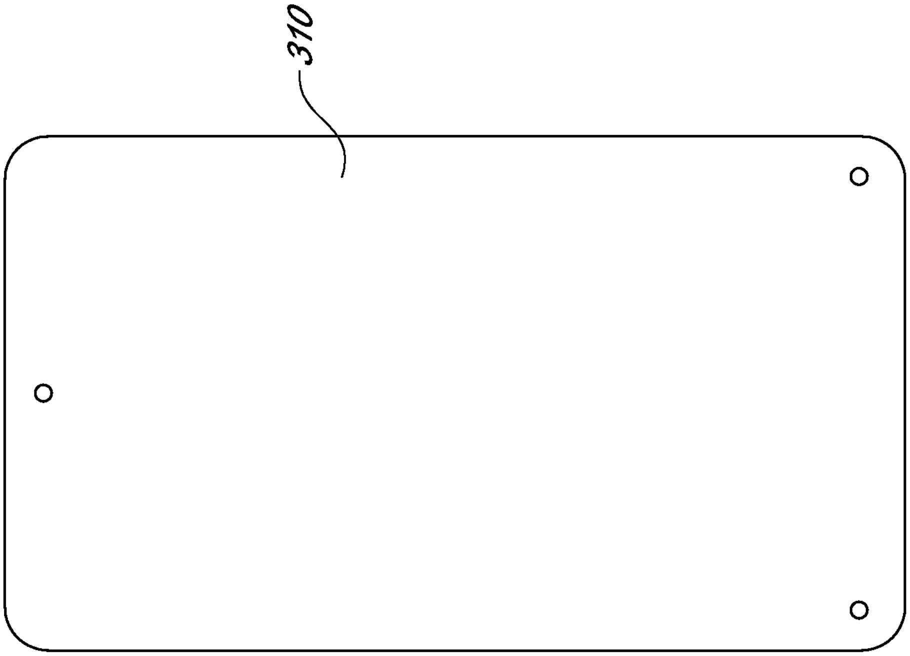
FIG. 5 illustrates the outer membrane 310 of system 300.
Figure 8:
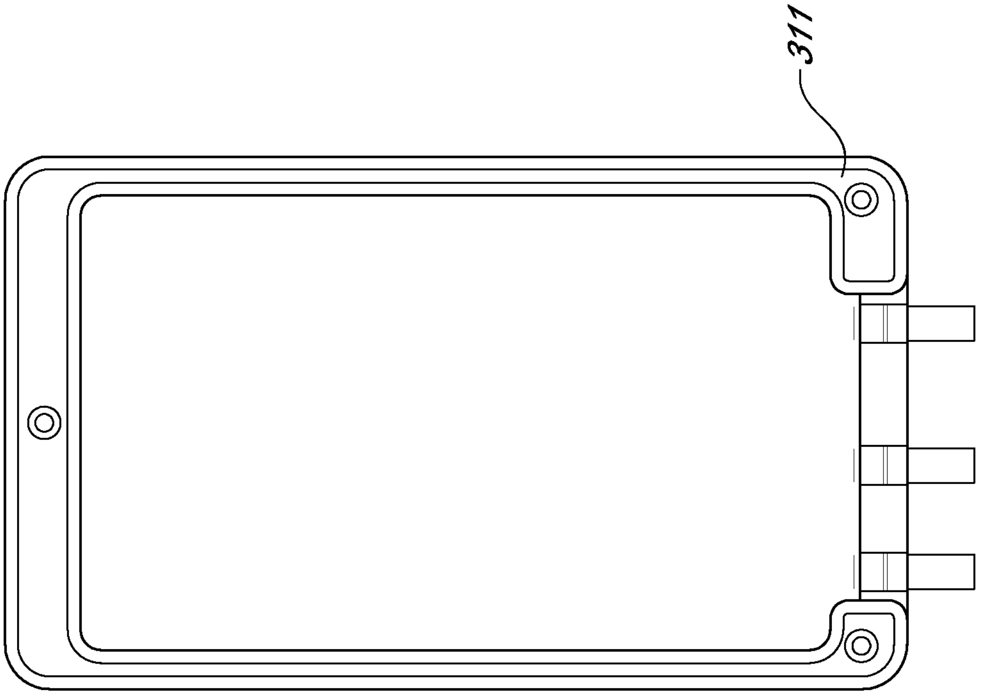
FIG. 8 illustrates exemplary seals 311 of system 300.

FIGS. 3 and 4 show the configuration of one embodiment of system 300 for the preparation of dried or dehydrated adipose tissue. System 300 comprises a first outer shell 310 and a second outer shell 340 (collectively and interchangeably referred to herein as "outer shells" or "outer shell") sealed together to form the outer layer of system 300. FIG. 5 shows an exemplary outer shell 310 (or 340) used in system 300. As discussed below, the outer shells 310, 340 can be affixed, joined, or sealed together to form a flexible, collapsible bag. FIG. 8 shows a detail of an exemplary seal 311 that can be used in the manufacture of system 300. The first and second outer shells 310 and 340 may be made from any medical grade flexible material known in the art, e.g., medical grade USP Class VI or Medical Grade ethyl vinyl acetate (EVA). In some embodiments, the flexible material that forms the first and second outer shells may be made of any material that can be bonded to itself. In other embodiments, the flexible material that forms the first and second outer shells may be made of any material that can be bonded to itself and be able to capture and/or seal any other material present in the system or subsystems. The outer shells may also be made from material that can withstand cryopreservation. The outer shells may also be made from material that is autoclavable, materials that are clear or colored, materials that are biocompatible, materials that are resistant to body fluids and/or materials that are sterilizable, e.g, with radiation, ethylene oxide, or dry heat.

By way of example only, the material may be Medical Grade EVA. In preferred embodiments, the material is one that can be bonded to itself and capture other material, e.g., filters present within the system. The bonding can be accomplished by processes further described herein such as RF welding. In certain embodiments, the outer shells may be sealed together by a double heat seal along the perimeter of the outer shells as in system 300 shown in FIGS. 3-13. The outer shells or any of the subsystems may be sealed using adhesives known to one of skill in the art. Types of adhesives to be used, including their mechanism of action could be considered. For example, adhesives which harden by loss of solvent, adhesives which harden by loss of water, adhesives which harden by cooling, adhesives which harden by chemical reaction, adhesives which do not harden—pressure sensitive adhesives may be used. Mechanisms such as adhesion by physical adsorption, adhesion by chemical bonding, electrostatic theory of adhesion, mechanical interlocking, adhesion by interdiffusion, weak boundary layers, and pressure sensitive adhesion may be considered. The surfaces to be joined must also be addressed such as surface topography, surface thermodynamics, and surface chemical analysis. Certain surfaces to be joined may also require particular pretreatments for optimum sealing. For example, appropriate pretreatments for metals, pretreatments for inorganic materials, pretreatments for plastics and pretreatments for elastomers may be considered.

In some embodiments, the systems and subsystems created advantageously possess mechanical properties that allow them to withstand stress. Thus, a global stress analysis, as well as, finite element analysis of adhesive joints must be performed. The durability of the adhesive joints must also be assessed. For example, additives to reduce photo-oxidative degradation must be considered. Behavior of structural joints to metals in wet surroundings must be considered. Water and adhesives, water and adhesive interfaces, other fluids, and timber joints must also be considered. In some embodiments, nondestructive testing may need to be performed using conventional ultrasonics, bond testers, rapid scanning methods and cohesive property measurement. The impact behavior of adhesively bonded joints may also need to be assessed. For example, an impact test of adhesives and adhesively bonded joints, characteristics of adhesives under high rate loading and stress distribution and variation in adhesively bonded joints subject to impact load may be assessed. It may also be desirable to assess fracture mechanics of adhesive bonds. For example, energy criterion for failure, stress intensity, energy release rate, thermodynamic, intrinsic, and practical adhesion energy, evaluation of fracture energy and durability. Other factors that may be evaluated include fatigue, vibration damping, joining similar and dissimilar materials and bonding composites.

In a particular embodiment, the outer shells of the system, or any of the subsystems, or any suitable combination may be sealed using Radio Frequency (RF) welding. RF welding is also referred to as Dielectric or High Frequency (HF) welding. RF welding is the process of applying radio frequency to fuse materials together. The resulting weld can be as strong as the original materials. RF welding relies on certain properties of the material being welded to cause the generation of heat in a rapidly alternating electric field. Specifically, the process involves subjecting the parts to be joined to a high frequency (13-100 MHz) electromagnetic field applied between two metal bars which causes heating of the material to be fused together. Only certain materials can be welded using this technique. Polyvinylchloride (PVC) and polyurethanes are the most common thermoplastics to be welded by the RF process. It is possible to RF weld other polymers including nylon, PET, EVA and some ABS resins, although special conditions may be required. For example, nylon and PET are weldable if preheated welding bars are used in addition to the RF power. RF welding may not be suitable for PTFE, polycarbonate, polystyrene, polyethylene or polypropylene. However, a special grade of polyolefin has been developed which does have the capability to be RF welded.

The primary function of RF welding is to form a joint in two or more thicknesses of sheet material. By incorporating a cutting edge adjacent to the welding surface, the process can simultaneously weld and cut a material. The cutting edge compresses the hot plastic sufficiently to allow the excess scrap material to be torn off, hence this process is often referred to as tear-seal welding. It is also possible to weld additional pieces of material onto the surface of a product.

In some embodiments, the system and subsystems may also be sealed using ultrasonic welding. When bonding material through ultrasonic welding, the energy required comes in the form of mechanical vibrations. The welding tool (sonotrode) couples to the part to be welded and moves it in longitudinal direction. The part to be welded on remains static. The parts to be bonded are simultaneously pressed together. The simultaneous action of static and dynamic forces causes a fusion of the parts without having to use additional material. This procedure can be used on an industrial scale for linking both plastics and metals that may be used in the system described herein. For ultrasonic welding of plastics, the thermal rise in the bonding area is produced by the absorption of mechanical vibrations, the reflection of the vibrations in the connecting area, and the friction of the surfaces of the parts. The vibrations are introduced vertically. In the contraction area, frictional heat is produced so that material plasticizes locally, forging an insoluble connection between both parts within a very short period of time. The prerequisite is that both working pieces have a near equivalent melting point. The joint quality in ultrasonic welding is very uniform because the energy transfer and the released internal heat remains constant and is limited to the joining area. In order to obtain an optimum result, the joining areas are prepared to make them suitable for ultrasonic bonding. Besides plastics welding, ultrasonics can also be used to rivet working parts of the system described herein or embed metal parts into plastic as needed.

The skilled artisan will appreciate that the systems disclosed herein can be made from materials other than the flexibile materials discussed above. For example, in some embodiments, the system or components of the system described herein can be manufactured from metals. In such embodiments, ultrasonic metal welding may be used to join, or affix system components to each other. Unlike in other processes, the parts to be welded are not heated to melting point, but are connected by applying pressure and high-frequency mechanical vibrations. In contrast to plastics welding, the mechanical vibrations used during ultrasonic metal welding are introduced horizontally. Specifically, during ultrasonic metal welding, a complex process is triggered involving static forces, oscillating shearing forces and a moderate temperature increase in the welding area. The magnitude of these factors depends on the thickness of the workpieces, their surface structure, and their mechanical properties. The workpieces are placed between a fixed machine part, i.e. the anvil, and the sonotrode, which oscillates horizontally during the welding process at high frequency (usually 20 or 35 or 40 kHz). The most commonly used frequency of oscillation (working frequency) is 20 kHz. This frequency is above that audible to the human ear and also permits the best possible use of energy. For welding processes which require only a small amount of energy, a working frequency of 35 or 40 kHz may be used.

The exemplary system 300 shown in FIGS. 3-13 comprises a first and second subsystem or first and second chambers created by inserting a filter material 320 between outer shell 310 and outer shell 340. The first subsystem or chamber is defined by the area between outer shell 310 and filter material 320 and the second subsystem or chamber is defined by the area between filter material 320 and outer shell 340. In certain embodiments, a double heat seal along the perimeter of system 300 captures the filter material 320 such that two distinct subsystems or chambers are formed within the system 300. The filter material can comprise a plurality of openings that would ideally enable or allow for the passage of a majority of certain contents, e.g., liquids, tumescent fluids, red blood cells, wash solutions (e.g., saline, lactated ringers solution, and the like), cellular debris and retention of a majority of certain contents e.g., mature adipocytes, regenerative cells, stem cells, progenitor cells and connective tissue. The components that pass through and those that are retained will be determined by the size of the openings in the filter material, i.e., generally components smaller than the openings will pass through and components larger than the openings will be retained. The filter material may accordingly be selected based on the size of the components of interest. It is to be understood that depending upon the conditions in the system, e.g., pressure, air flow, viscosity, etc, the number or percentage of components smaller than the openings on the filter material that will pass through and the number or percentage of components larger than the openings that will be retained, may differ.

Figure 6:
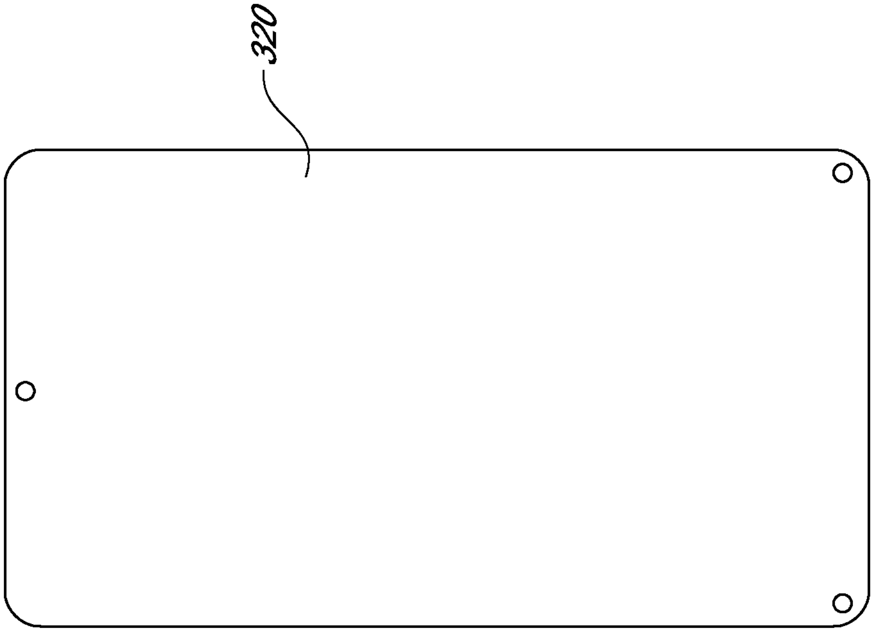
FIG. 6 illustrates the filter 320 of system 300.

The filter material preferably has a plurality of pores allowing fluid communication within or between subsystems. The pores enable compositions (or components thereof) inserted in the one subsystem to diffuse into another subsystem or vice versa. The pores are preferably located on a substantial area of the surface of any filter that may be used. An exemplary filter is shown in FIG. 6.

Any filter that allows excess liquids, red blood cells, or cellular debris may be used in system 300. For example, any filter that retains adipocytes, regenerative and stem cells, or connective tissue may be used. Some embodiments provide a system 300 in which the pores of the filter material 320 can be range from about 1 micron to about 750 microns, e.g., 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, or 750 microns, or any number or range in between. Preferably, the plurality of openings or pores in the filter material is greater than 40 μm. For example, in one embodiment, the plurality of openings in the filter material 320 can be 74 microns. In other embodiments, the plurality of openings can range from about 73 to about 264 microns.

Figure 7:
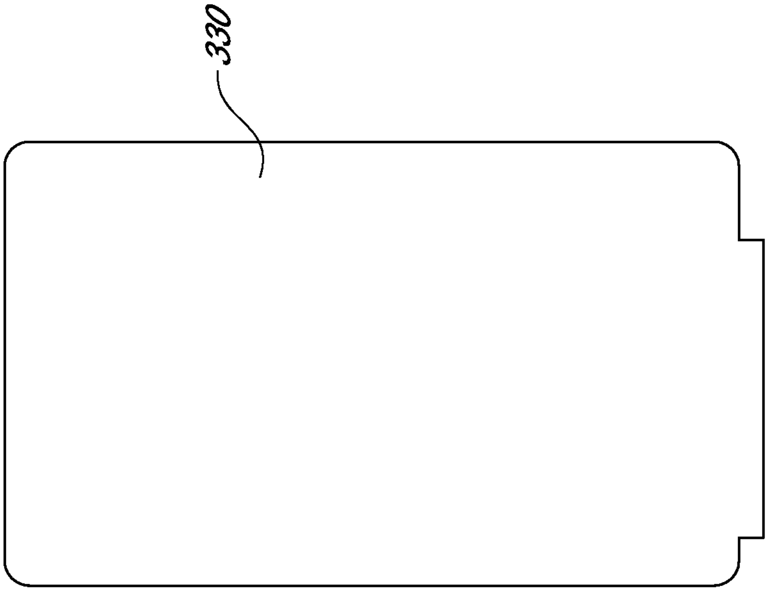
FIG. 7 illustrates the separation screen 330 of system 300.
Figure 9:
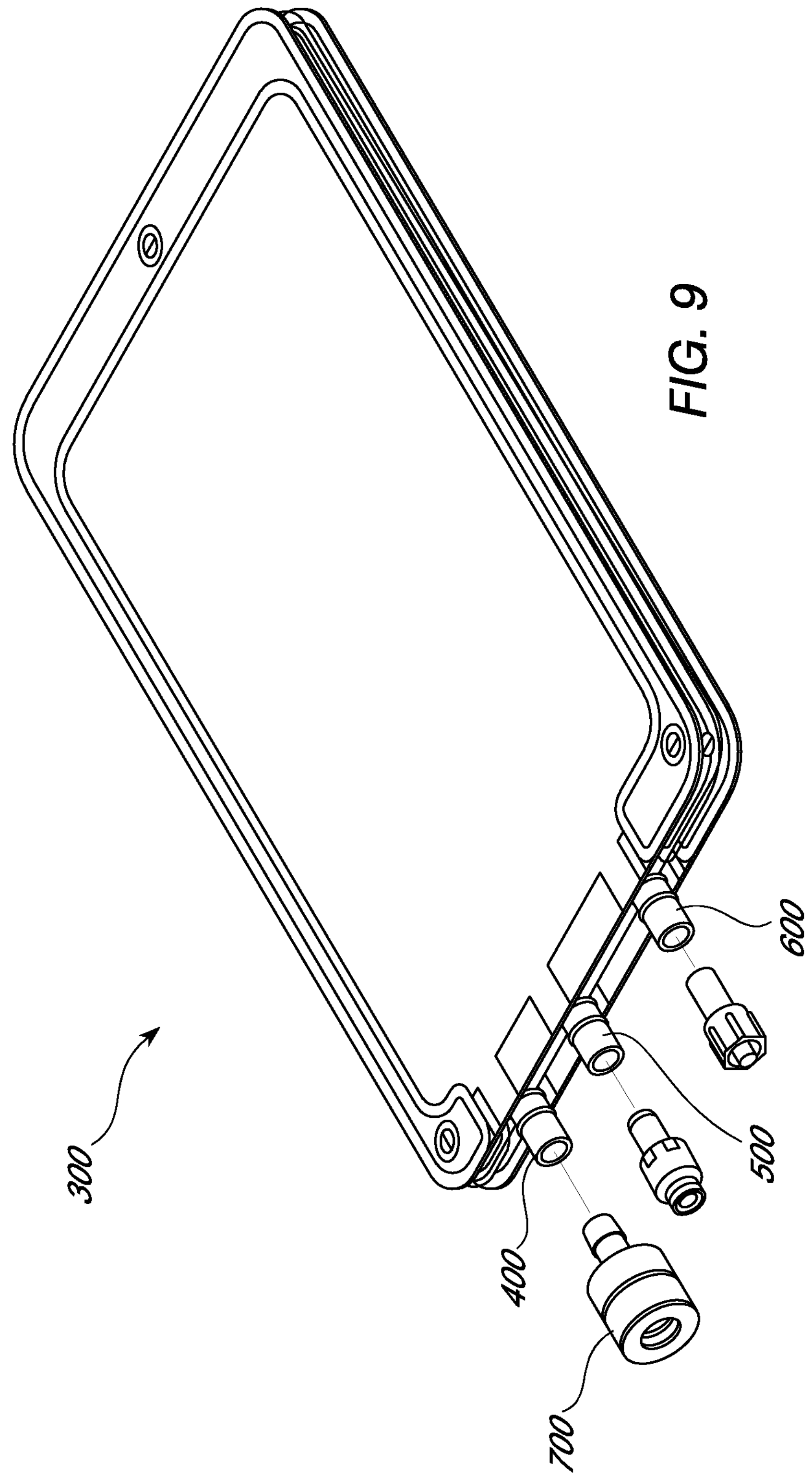
FIG. 9 is a perspective view of a system 300 with ports and adaptors 600.
Figure 10:
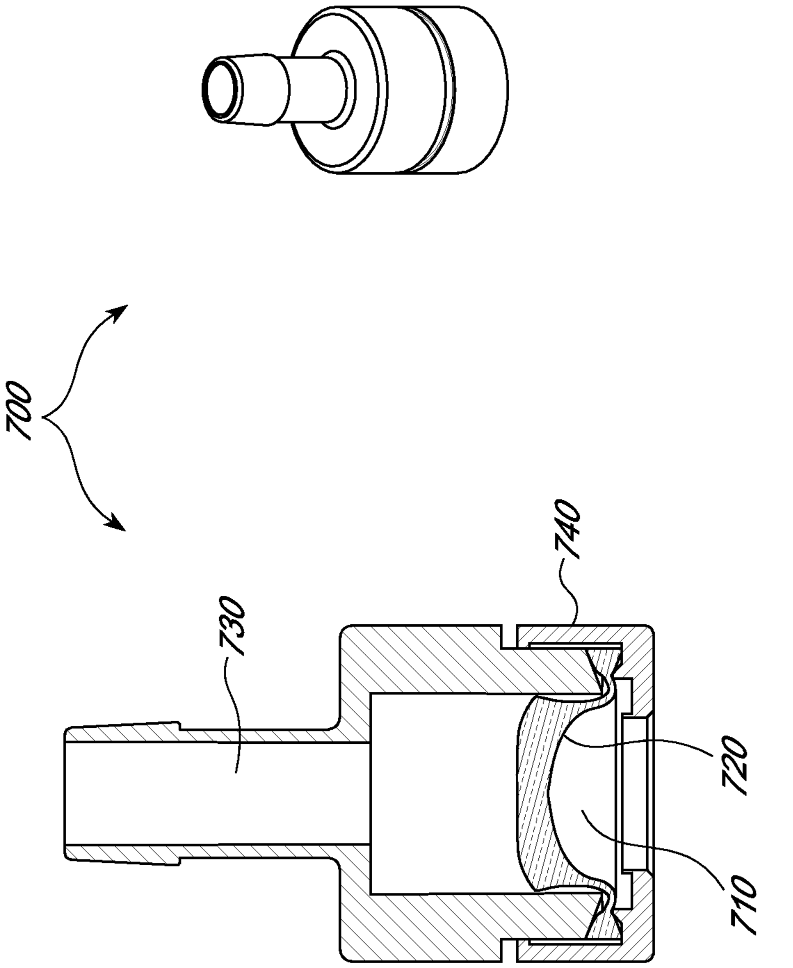
FIG. 10 is a cutaway view of a tissue port assembly 600 used with the ports of system 300.
Figure 11:
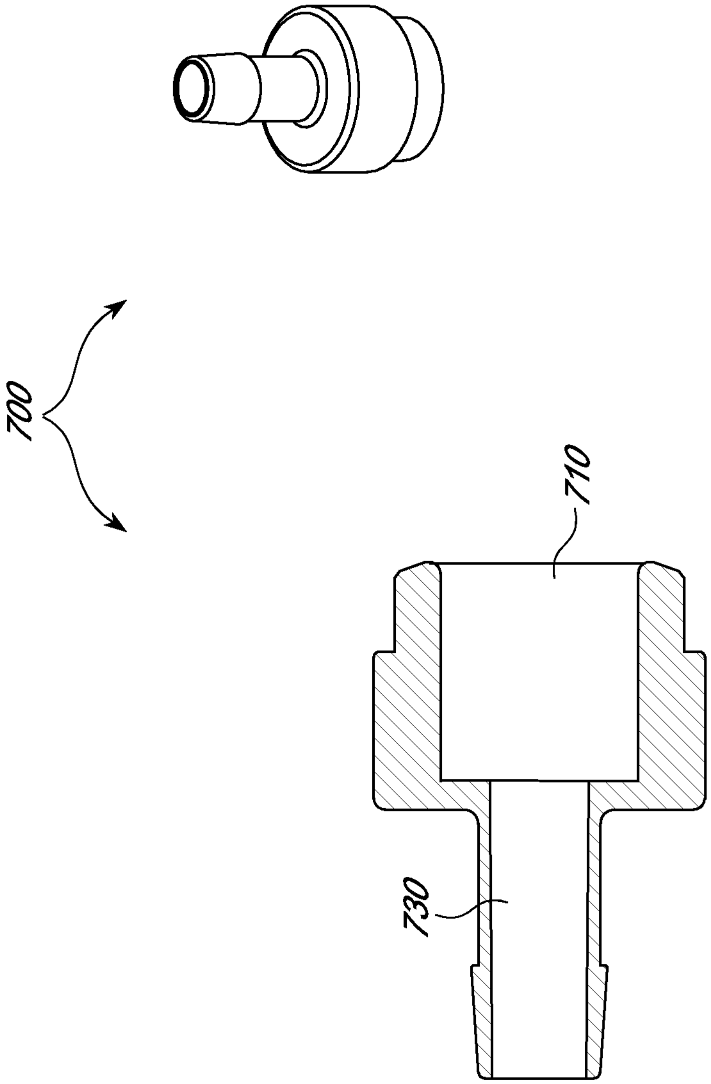
FIG. 11 is a cutaway view of a tissue port assembly 600 used with the ports of system 300.

As shown in FIGS. 3-13, in some embodiments, the second subsystem or chamber, i.e., the area between filter material 320 and outer shell 340 described above can be further divided into two subsystems such that a third subsystem or chamber is formed. For example, a separator 330, e.g. a separation screen, a mesh, or filter is inserted between filter material 320 and outer shell 340. An exemplary separator comprising a separation screen is shown in FIG. 7. The second and third subsystems or chambers can contain the solutions, effluents, waste, debris and other unwanted materials from the first subsystem. In certain embodiments, the second and third subsystems or chambers are partially distinct from each other. In some embodiments, the second and third subsystems or chambers are fully distinct from each other. For example, in some embodiments, the separator 330, e.g., separation screen, has a degree of freedom, or is completely free-floating within the second subsystem such that a third subsystem is formed that is not completely separate from the second subsystem. In other embodiments, the second and third subsystems are completely distinct from each other in that the separator, e.g., separation screen or the like is captured between the outer layers 310 and 340 using any of the joining mechanisms known in the art or described herein, e.g., adhesive joining, RF welding, or ultrasonic welding. The skilled artisan will readily appreciate that several approaches can be used to affix the different layers of system 300, e.g., the first and second outer shells, the filter, and the separator, can be selected to ensure optimal seal strength.

In some embodiments, the separator 330 (e.g., a separation screen) is configured to minimize contact between the filter material 320 and the outer shell 340. Minimal contact prevents the filter material 320 and the outer shell 340 from adhering to one another during the processing of the tissue (e.g., if a vacuum develops within the bag). Thus, the separation screen 330 creates a space between the filter material 320 and the outer shell 340. In certain embodiments the separator can comprise ribs, struts and other features that create a space between the outer shell 340 and the filter 320. In other embodiments, the side of the outer shell 340 that faces filter material 320 can be textured to create the requisite space, thereby obviating the need for a distinct separator. The creation of space between the filter and the outer shell of the system generates a force in the bag that pulls, draws or wicks excess fluid from the adipose tissue into the second and/or third subsystem. The excess fluid can then be directed into a waste container. The space created by the separator, e.g., separation screen 330, and/or the material used to create the separator is also preferably designed, configured, or selected to wick the lipid present in the adipose tissue thereby helping to remove the lipid and fluids from the tissue within the first subsystem or chamber and further drying or dehydrating the tissue.

In certain embodiments, the separator 330 is made from a porous material and/or comprises a plurality of openings or pores. In certain embodiments, the plurality of pores in the separator 330 can be about 300 to about 3000 microns or any number in between this range, e.g. about 500 to about 2000 microns. Preferably, the plurality of openings or pores have a diameter that is greater than or equal to about 300 microns, 400 microns, 500 microns, 600 microns, 700 microns, 800 microns, 900 microns, 1000 microns, 1100 microns, 1200 microns, 1300 microns, 1400 microns, 1400 microns, 1500 microns, 1600 microns, 1700 microns, 1800 microns, 1900 microns, 2000 microns, 2100 microns, 2200 microns, 2300 microns, 2400 microns, 2500 microns, 2600 microns, 2700 microns, 2800 microns, 2900 microns, 3000 microns, or any number in between this range. In one embodiment, the plurality of openings is about 1000 microns. In some embodiments, the separator is made from a porous material having an open area that is greater than or equal to about 10%, 12%, 14%, 16%, 1%, 20%, 22%, 24%, 26%, 28%, 30%, 32%, 35%, 36%, 38%, 40%, 42%, 44%, 46%, 48%, 50%, 52%, 54%, 56%, 58%, 60%, 62%, 65%, or any % within this range. The skilled artisan will appreciate that larger-sized pores allow faster transfer or drainage of material from the first chamber into the second chamber, and that the pore size of the separator can be adjusted to balance wicking and/or drainage or filtration properties. In some embodiments, liquid and lipid adsorbs to and or fills the open areas of the porous separator. Applicants have made the surprising discovery that in some embodiments, separators that comprise pores larger than the pores in the filter material facilitate the removal of fluid from the adipose tissue and fluids from the first chamber of the system. Thus, in some embodiments, the separator, e.g., the separation screen 330, is a porous material, wherein the pores have a larger diameter or sizes than the filter material 320 described above.

In some embodiments, the separator comprises a biocompatible material that traps or wicks lipids and/or fluids. For example, the separators can be made of a polyester, a nylon, rayon, cellulose nitrate and cellulose acetate. In some embodiments, the separator is made of a flexible material, and in some embodiments, the separator made of a rigid material. Preferably, the separator is made of a polyester mesh, e.g., with a pore size of 1000 microns.

As shown in FIGS. 3-13, the system 300 can comprise one or more ports to allow for adding or removing materials into and out of the system. For example, the system 300 shown in FIGS. 3, 4, 8 and 9 have three separate ports. Ports 400 and 500 are in communication with the first subsystem, e.g., the area between outer shell 310 and filter material 320. Port 600 is in communication with the second and/or the third subsystem, e.g., the area between the filter material 320 and the separation screen 330 and/or the area between separation screen 330 and outer shell 340. In some embodiments, however, the system can include only one port, or only two ports, e.g., one inlet port and one outlet port. In other embodiments, the system can include more than three ports, e.g., 4, 5, 6, 7, 8, 9, 10 or more ports.

Generally, the ports comprise at least one aperture that extends from the environment into the interior of the system or subsystem or vice versa. The apertures have an airtight and watertight seal along the seams of the ports. As discussed further below, in some embodiments, the ports are configured to be coupled to one or more connectors, conduits, port assemblies, adaptors, caps, or syringes.

The ports may provide an access point for inserting various fluids, e.g., washing and rinsing fluids, and removing such fluids and effluent. Preferably, the ports can be sealed (e.g., with a valve). In some embodiments, the ports can be manually sealed with a clamp. In some embodiments, the ports can be sealed by a cap. In some embodiments, the ports comprise self-sealing valves, e.g., a deformable valve that provides for unidirectional flow of fluid or contents into, but not out of the internal chamber(s) of the system. In other embodiments, the deformable valves provide for bi-directional flow. Deformable valves can be made from any deformable material known in the art, such as rubber, neoprene, silicone, polyurethane, or the like. In some embodiments, the ports comprise a luer-activated valve. In some embodiments, the ports are located in the system such that when the system is held upright, one or more ports is positioned inferiorly such that fluids and effluent will egress with the assistance of gravitational forces, suction or pressure. Other ports may also be utilized with the system 300 of the invention, e.g, ports for venting, ports for adding materials or gases to the system or subsystems etc.

Ports on the system or subsystem can be configured to be directly or indirectly (i.e., via an adaptor) interconnected with or coupled to a syringe or catheter used to suction the adipose material from the source body such that the adipose tissue is directly transported into system anaerobically. Similarly, a cannula or syringe maybe attached to a port for anaerobic transplantation of the refined tissue. Accordingly, in some embodiments, the ports on the system or subsystem are configured to be directly or indirectly coupled with disposable or re-usable syringes. For example, in some embodiments, the ports are configured to be directly or indirectly coupled with a 1 cc syringe, a 2 cc syringe, a 5 cc syringe, a 10 cc syringe, a 20 cc syringe, a 50 cc syringe, a 60 cc syringe, a 100 cc syringe, a 250 cc syringe, or the like. In some embodiments, the ports are configured to be directly or indirectly coupled with a syringe having a large bore tip, e.g. a Toomey syringe.

Figure 12:
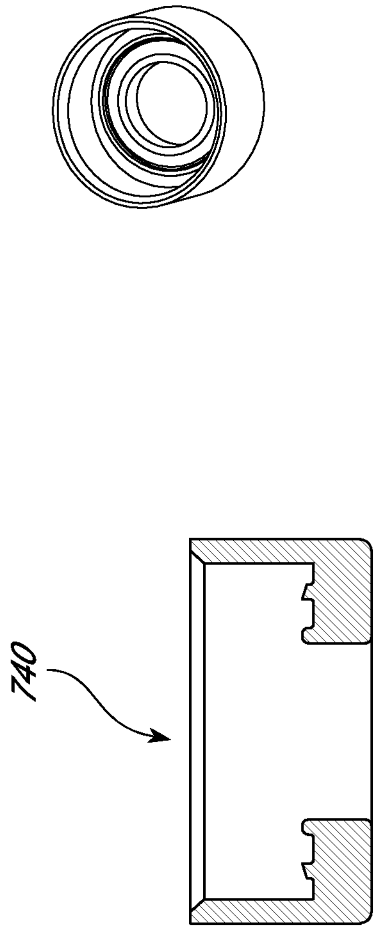
FIG. 12 is a cutaway view of a cap 610 used with a tissue port assembly 600.

In some embodiments, the system 300 comprises a tissue access port assembly 700 to facilitate aseptic delivery or removal of contents (e.g., adipose tissue), to and from the first chamber or subsystem. (See, e.g., FIG. 9). An exemplary tissue access port assembly 700 is shown in greater detail in FIGS. 10 and 11. In some embodiments, the tissue access port assembly comprises a large bore cylindrical opening 710. The large size of bore 710 facilitates delivery and removal of tissue into the first chamber. A deformable plastic valve 720 can provide a barrier that prevents material from passing through the opening 710 into the body of the port 730. The deformable plastic valve 720 can be configured to open and permit flow of contents through the bore into the body 730 of the tissue access port, leading into the first chamber of the system by insertion of a syringe tip (not shown) therein. The deformable plastic valve 720 returns to a closed default state upon removal of the syringe tip from the valve, thereby sealing the port and blocking the flow of any content (e.g., tissue or liquid), out of the body of the tissue access port when not in use. In some embodiments, the tissue access port assembly is configured to be connected a cap 740 to provide an additional seal to the tissue access port when the port is not in use. A more detailed illustration of an exemplary cap 740 is shown in FIG. 12. In some embodiments, the tissue access port assembly can be removable from system 300. In some embodiments, the tissue access port assembly is affixed to or joined to system 300, e.g. via an adhesive such as UV adhesive.

In some embodiments, the tissue access port assembly can be configured to interconnect with an adaptor or connector. In some embodiments, the adaptor or connector is configured to join a syringe tip to a port of the system. As discussed above, by way of example, adaptors such as tissue port assemblies can be integral to, or removable from the port(s). In some embodiments, the adaptor or connector comprises a luer connector. In some embodiments, the adaptor or connector comprises a removal adaptor comprising a deformable valve.

In some embodiments, ports of the system can comprise, or be connected to, an assembly configured for more than one flow path, e.g, a Y connector or the like. In some embodiments, the Y connector is configured to allow obstruction of one or both flow paths at as desired, e.g., by clamping the individual lumens or flowpaths of the Y connector. In some embodiments, the Y connector comprises a switch located at the junction of the common and individual flowpaths of the Y connector that that can be adjusted to enable simulataneous flow through each individual flowpath, one flowpath, or to obstruct both flowpaths, as desired.

In some embodiments, the ports of the system can be connected to conduits or tubing that enable fluid communication to one or more systems or subsystems while maintaining a closed pathway. For example, in some embodiments, the system 300 may optionally comprise a waste bag (not shown), waste receptacle (not shown), waste conduit (not shown) and/or a waste container (not shown). In certain of these embodiments, all of the subsystems are in fluid communication with each other. In other embodiments, none of the subsystems are in fluid communication with each other. In a particular embodiment, one subsystem is sealed off from the other two subsystems wherein the two subsystems are in fluid communication with each other. Preferably, the entire system, including the subsystems, are flexible allowing for the system to be of any size or shape and accommodate a wide range of volumes. Alternatively, the entire system, subsystems and associated components, may be rigid. Or, some subsystems and associated components may be flexible whereas other subsystems and associated components may be rigid.

Figure 13:
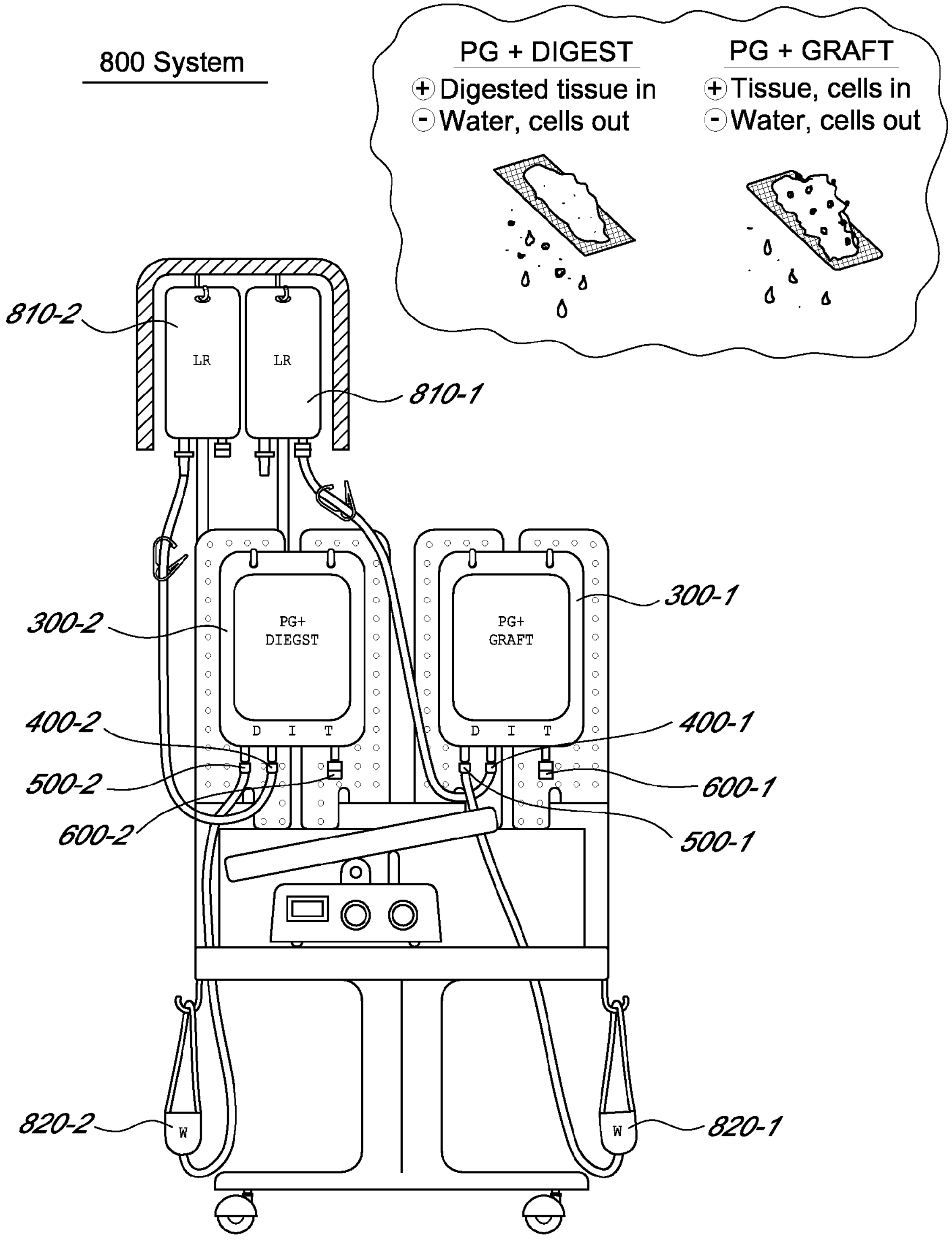
FIG. 13 is an illustration of an exemplary system 800 used to optimize an adipose tissue graft.

FIG. 13 illustrates an exemplary embodiment of a system 800, comprising a system 300-1 in fluid connection with other systems and subsystems. As shown in FIG. 13, ports 400-1 and 500-1 can connect to a wash solution source 810-1 and a waste bag 820-1, respectively. The system 300-1 can be connected with a similar system 300-2, while maintaining a closed pathway. Adipose tissue is introduced into the first chambers systems 300-1 and 300-2 as described herein above, e.g., through tissue entry/removal ports 600-1 and 600-2, respectively. The adipose tissue in system 300-2 is used to produce a dried or dehydrated graft as described above. The adipose tissue in system 300-1 is processed to produce lipo-digestate or a concentrated population of adipose-derived cells comprising regenerative cells. Port 500-1 or an alternative port (not shown) can be connected to a solution source, e.g. 810-1, configured for the aseptic introduction of wash solution and/or enzymes into the second chamber of system 300-1 for tissue rinsing and digestion. Port 400-1 can be connected to a waste bag 820-1. The lipo-digestate in the first chamber of 300-1 can be aseptically transferred to the dried or dehydrated adipose tissue within the first chamber of system 300-2 via a conduit (not shown) that connects the ports 600-1 and 600-2, while maintaining a closed system.

The systems disclosed herein can yield adipose tissue grafts and implants that have significantly lower amounts of undesirable material, such as red blood cells, white blood cells and lipid, than equivalent amounts of adipose tissue from the same subject at the same site that have been processed by methods such as centrifugation and/or conventional gravity separation. In some embodiments, the adipose tissue grafts produced using the systems disclosed herein have at least about 1×, 2×, 3×, 4×, 5×, 6×, 7×, 8×, 9×, 10× (or any number in between this range) fewer white blood cells than that present in an equivalent unit of adipose tissue that has been excised from the same subject at the same site and prepared using a centrifugation method, e.g., wherein the excised tissue is spun in a fixed angle centrifuge. For example, in some embodiments, the adipose tissue grafts produced in the systems disclosed herein contain less than 75%, less than 80%, less than 85%, less than 90%, less than 95%, or less, or any % in between, of the number of white blood cells in an equivalent unit of adipose tissue from the same individual.

In some embodiments, the adipose tissue grafts produced using the systems disclosed herein have at least about 1×, 2×, 3×, 4×, 5×, 6×, 7×, 8×, 9×, 10× (or any number in between this range) fewer red blood cells than in an equivalent unit of adipose tissue that has been excised from the same subject at the same site and prepared using a centrifugation method, e.g., wherein the excised tissue is spun in a fixed angle centrifuge. For example, in some embodiments, the adipose tissue grafts produced in the systems disclosed herein contain less than 75%, less than 80%, less than 85%, less than 90%, less than 95%, or less, or any % in between, of the number of red blood cells in an equivalent unit of adipose tissue.

In some embodiments, the adipose tissue grafts produced using the systems disclosed herein have at least about 1×, 2×, 3×, 4×, 5×, 6×, 7×, 8×, 9×, 10× (or any number in between this range) less lipid than in an equivalent unit of adipose tissue that has been excised from the same subject and prepared using a centrifugation method, e.g., wherein the excised tissue is spun in a fixed angle centrifuge. For example, in some embodiments, the adipose tissue grafts produced in the systems disclosed herein contain less than 75%, less than 80%, less than 85%, less than 90%, less than 95%, or less, or any % in between, of the percentage of lipid content than in an equivalent unit of adipose tissue.

In addition to the ability to produce adipose tissue grafts with fewer undesirable components, the grafts produced by the systems disclosed herein can also exhibit hydration characteristics that facilitate supplementation with adipose-derived regenerative cells and/or retention of the implant. Specifically, the hydration state of an adipose tissue graft prepared as described herein is less hydrated than a graft of an equivalent unit of adipose tissue isolated from the same subject at the same site and prepared using gravity separation alone.

The skilled artisan will appreciate, however, that in some embodiments, systems can be designed with a flexible bag that is not comprised of two different outer shells sealed together, but that is, rather, a seamless bag. A filter can be sealed, joined or affixed within the seamless bag, to define first and second subsystems or chambers within the interior of the bag.

Figure 14A:
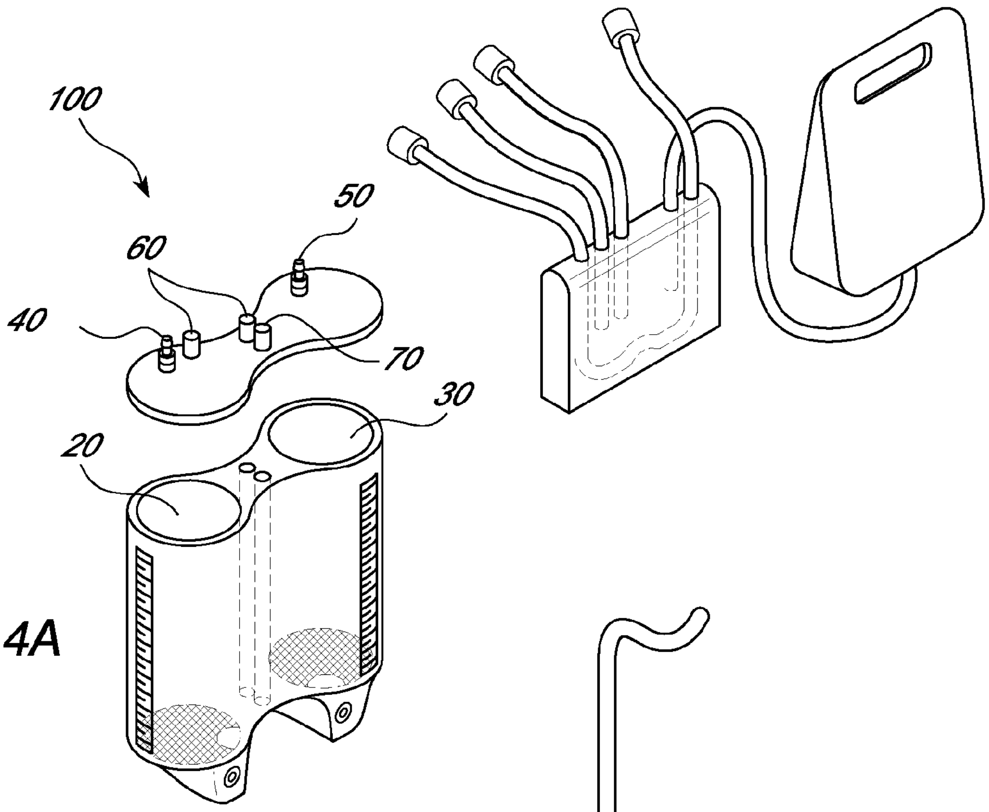
FIGS. 14A and 14B are perspective views of an exemplary tissue enrichment device.
Figure 14B:
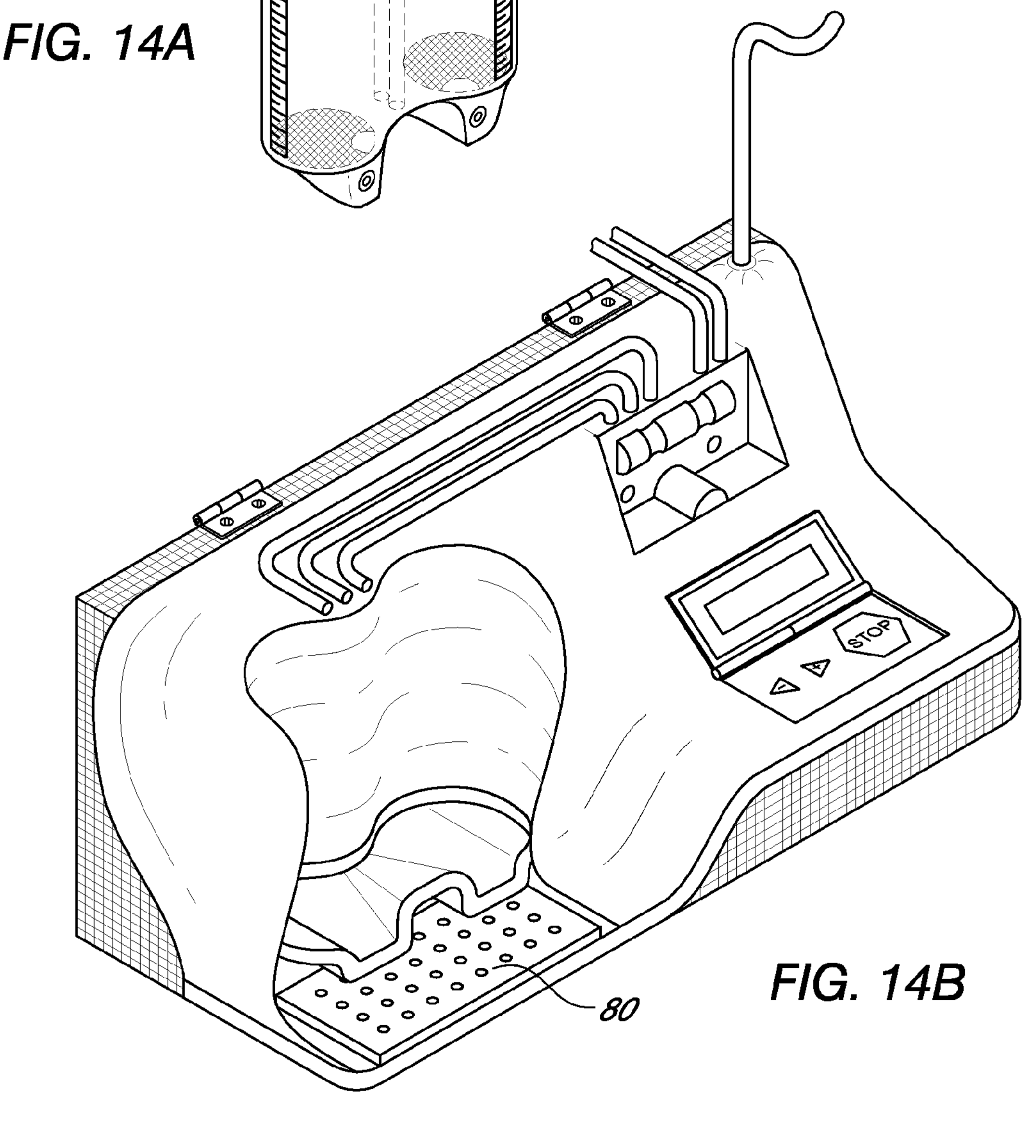

An exemplary device 100 for producing the supplemented, enhanced, or fortified fat grafts or adipose tissue implants disclosed herein is shown in FIG. 14. FIG. 14A shows a perspective view of a canister 10 that includes at least two chambers 20, 30. One chamber 20 can be used to produce lipo-digestate from unprocessed tissue. A second chamber 30 can be used to receive and store unprocessed adipose tissue, to be used as the fat graft in the generation of the supplemented adipose tissue graft.

In the embodiment shown in FIG. 14, each chamber 20, 30, has a tissue entry port 40, 50, configured to receive unprocessed adipose tissue. It will be appreciated, however, that in some embodiments, the canister 10 has only one tissue entry port. In some embodiments, the tissue entry ports 40, 50 are configured to operably connect to a cannula (not shown), such that lipoaspirate directly enters into the chamber(s) 20, 30 during liposuction. For example, the tissue inlet port 40, 50 can be coupled to a cannula (not shown) by way of tubing to define a tissue removal line. In some embodiments, the cannula can be an integrated, single-use liposuction cannula, and the tubing can be a flexible tubing. The cannula can dimensioned to be inserted into a subject to remove adipose tissue from the subject. The tubing used in the system can be capable of withstanding negative pressure associated with suction assisted lipoplasty to reduce the likelihood of collapsing. A suction device (not shown) such as a syringe or electric vacuum, among other things, can be coupled to the canister 10, and configured to provide a sufficient negative pressure to aspirate tissue from a subject.

The chambers 20, 30 of the canister 10 can be physically separated from each other, such that the flow of contents of one chamber 20 (e.g., the chamber containing lipo-digestate) into the other chamber 30 (e.g., the chamber containing the fat graft), is controlled. In some embodiments, the chambers are in fluid connection, for example, through a port that can be sealed off, to ensure flow of contents from one chamber to the other chamber only when desired. For example, in some embodiments, flow of contents from one chamber 20 to another chamber 30, occurs through a conduit. The optional conduit can include one or more clamps (not shown) to control the flow of material among various components of the system. The clamps can be used to maintain the sterility of the system by effectively sealing different regions of the system. Alternatively, the optional conduits may include one or more valves that control the flow of material through the system. The valves can be electromechanical pinch valves, pneumatic valves, hydraulic valves or mechanical valves. In some embodiments, the valves can be activated or actuated by a control system, which may be coupled to levers. The levers can be manually manipulated and/or automatically manipulated, for example, through a processing device which may activate the valves at predetermined activation conditions. In certain automated embodiments, activation of the valves may be partially automated and partially subject to the user's preference such that the process may be optimized. In yet other embodiments, certain valves may be activated manually and others automatically through a processing device. The valves may also be used in conjunction with one or more pumps, e.g., peristaltic pumps or positive displacement pumps (not shown). The conduits and/or the valves can also include sensors, such as optical sensors, ultrasonic sensors, pressure sensors or the like, that are capable of distinguishing among the various fluid components and fluid levels that flow through the system.

In some embodiments, one or both chambers can include one or more ports 60 for the removal of waste, e.g., saline, mature adipocytes, red blood cells, and the like, the addition of components, e.g., wash solution, enzymes, cells, and the like, or for an air inlet or outlet vent. In some embodiments, chamber 30 can include a port, or outlet 70 configured for the aseptic removal of the supplemented fat graft. Outlet 70 can be structured to pass the composition (e.g., supplemented fat graft) from chamber 30 to a subject under the appropriate conditions. For example, in some embodiments a syringe can be used to withdraw the composition, and outlet 70 is able to accommodate a needle of the syringe without compromising the sterility of the system or composition. In additional embodiments, the outlet can be coupled to a device that is configured to administer the composition, but not to withdraw the composition, such as a cannula that administers the composition by applying positive pressure to displace the composition through the cannula. Accordingly, outlet 70 can be configured to allow the composition contained in chamber 30 to be passed into the cannula (not shown). In other embodiments, outlet 70 can comprise, or be coupled in a closed-system fashion to, the device for administering the composition, such as a needle of a syringe or a cannula for administering the composition by applying positive pressure.

In some embodiments, one or both chambers 20, 30 of the canister 10 can be configured to aseptically receive solutions and agents, such as washing solutions (saline, and the like), disaggregation agents, or other agents or additives. The device can include containers configured to hold their contents in a sterile manner, e.g., a collapsible bag, such as an IV bag used in clinical settings. These containers may have conduits coupled to one or both chambers 20, 30. For example, the device can be configured such that a container holding a rinsing or washing agent (e.g., PBS, PLASMALYTE®, NORMOSO®, or Lactated Ringer's solution) can be aseptically delivered to chamber 20 and chamber 30. In some embodiments, the device 100 can be configured such that a container holding a disaggregation agent coupled to canister 10 to deliver the disaggregation agent(s) to the interior of chamber 20. Solutions and agents can be delivered to the interior of the chambers 20, 30 of the canister through any art-recognized manner, including gravity pressure applied to the outside of the containers, or by placement of a positive displacement pump on the conduits. In automated embodiments, a processing device calculates various parameters, e.g., the volume of saline and time or number of cycles required for washing, as well as, the concentration or amount of disaggregation agent and the time required for disaggregation based on information initially entered by the user (e.g., volume of tissue being processed). Alternatively, the amounts, times etc. can be manually manipulated by the user. In some embodiments, the device is configured to agitate, or shake, one or both chambers of the canister. For example, in some embodiments, the device comprises an orbital motion platform 80 configured to agitate the contents of chamber 20, during the disaggregation process.

The components of the canister 10 can be made of materials that are non-reactive with biological fluids or tissues, and non-reactive with agents used in processing biological fluids and tissues. In addition, the materials from which the various components are made should be capable of withstanding sterilization, such as by autoclaving, and irradiation, including but not limited to beta- or gamma-irradiation. In some embodiments, the canister is made from disposable materials. In some embodiments, the canister can be made from non-disposable material, which can be used more than one time. By way of example, the tubing and the cannula handle may be made of any suitable material, such as polyethylene. The cannula may be made of stainless steel. For example, in some embodiments, the canister is made from polycarbonate acrylic, ABS, ethylene vinyl acetate, or styrene-butadiene copolymers (SBC). The fluid pathway of the device is preferably pyrogen free, i.e., suitable for blood use without danger of disease transmittal. In some embodiments, the canister 10 is constructed of a material that allows the user to visually determine the approximate volume of tissue present in the chamber.

In some embodiments, the device includes one or more temperature control devices (not shown) that are positioned to adjust the temperature of the material contained within one or more chambers 20, 30 of the system. The temperature control device can be a heater, a cooler or both, i.e., it may be able to switch between a heater and a cooler. The temperature device can adjust the temperature of any of the material passing through the device 100, including the tissue, the disaggregation agents, resuspension agents, the rinsing agents, the washing agents or additives. For example, heating of adipose tissue facilitates disaggregation whereas the cooling of the regenerative cell output is desirable to maintain viability. Also, if pre-warmed reagents are needed for optimal tissue processing, the role of the temperature device would be to maintain the pre-determined temperature rather than to increase or decrease the temperature.

In some embodiments, the device 100 can be automated. In some embodiments, the device 100 can include a processing device (e.g., microprocessor or personal computer) and associated software programs that provide the control logic for the system to operate and to automate one or more steps of the process based on user input. In certain embodiments, one or more aspects of the system may be user-programmable via software residing in the processing device. The processing device may have one or more pre-programmed software programs in Read Only Memory (ROM). For example, the processing device may have pre-programmed software tailored for processing blood, another program for processing adipose tissue to obtain small volumes of regenerative cells and another program for processing adipose tissue to obtain larger volumes of regenerative cells. The processing device may also have pre-programmed software which provides the user with appropriate parameters to optimize the process based on the user's input of relevant information such as the amount of regenerative cells required, and various post-processing manipulation, etc.

In some embodiments, the software can automate steps such as controlling the ingress and egress of fluids and tissues along particular tubing paths by controlling pumps and valves of the system; controlling the proper sequence and/or direction of activation; detecting blockages with pressure sensors; mixing mechanisms, measuring the amount of tissue and/or fluid to be moved along a particular pathway using volumetric mechanisms; maintaining temperatures of the various components using heat control devices; and integrating the disaggregation process with timing and software mechanisms.

The following examples are provided to demonstrate particular situations and settings in which this technology may be applied and are not intended to restrict the scope of the invention and the claims included in this disclosure. A number of publications and patents have been cited hereinabove. Each of the cited publications and patents are hereby incorporated by reference in their entireties.

The following example compares the purity and hydration of adipose tissue grafts obtained using the system disclosed herein to equivalent units of unprocessed adipose tissue, and equivalent units of adipose tissue grafts produced by gravity separation and centrifugation.

Example 1

Aspirated adipose tissue was collected from clinical offices by either liposuction (N=5), laser (N=3) or Body-jet harvesting (N=2) methods from 10 human subjects (N=10). The aspirated tissue samples were randomly divided into four groups: (1) control; (2); gravity separation; (3) centrifugation; and (4) PUREGRAFT™ tissue graft preparation. The control samples were analyzed directly, without further manipulation. Samples in the gravity separation group were set aside in a 60 mL syringe for ten minutes. The fluid portion of the samples was discarded and the remaining adipose tissue was analyzed. For the centrifugation group, samples were loaded into a capped 10 mL syringe placed into an IEC fixed angle rotor centrifuge at centrifuged at 3000 rpm (~1, 200 g) for 3 minutes. Free lipid at the top of the adipose tissue was removed by aspiration and the infranatant drained following centrifugation and the remaining graft tissue was analyzed. Samples in the PUREGRAFT™ group were washed in a system 300 described herein above (PureGraft™). Briefly, tissue was introduced into the first chamber of the system 300 as described above. The tissue was washed with 2×150 mls of Lactated Ringer's solution. The excess fluid and lipid was allowed to drain from the second chamber of the system. The dried tissue was removed through the tissue entry port and used for result analysis.

Figure 15:
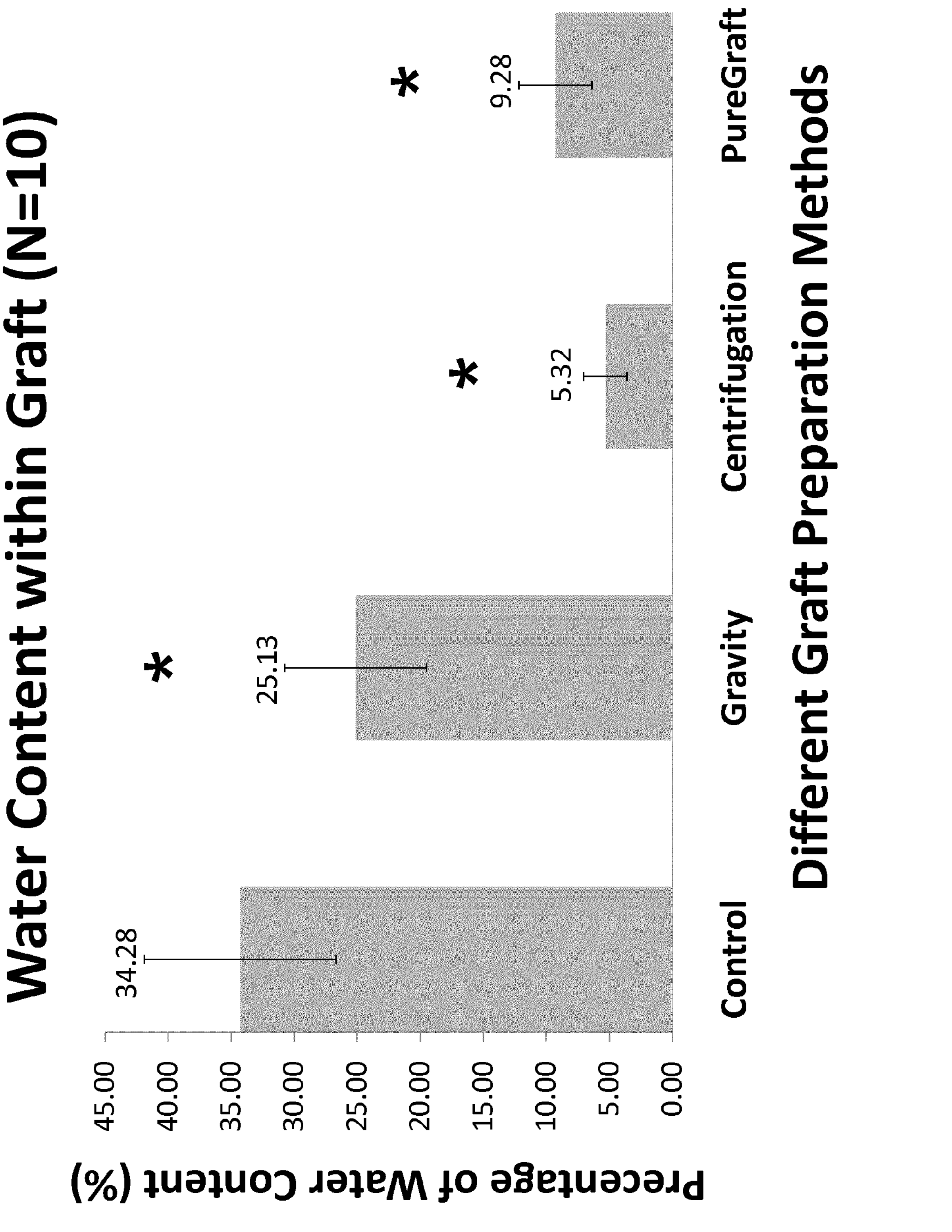
FIG. 15 is a bar graph showing the percent water content (v/v) of unprocessed adipose tissue (control), adipose tissue prepared by a gravity preparation method (Gravity), adipose tissue prepared by a centrifugation method (Centrifugation) and dried adipose tissue prepared according to the methods and systems described herein (PureGraft).
Figure 16:
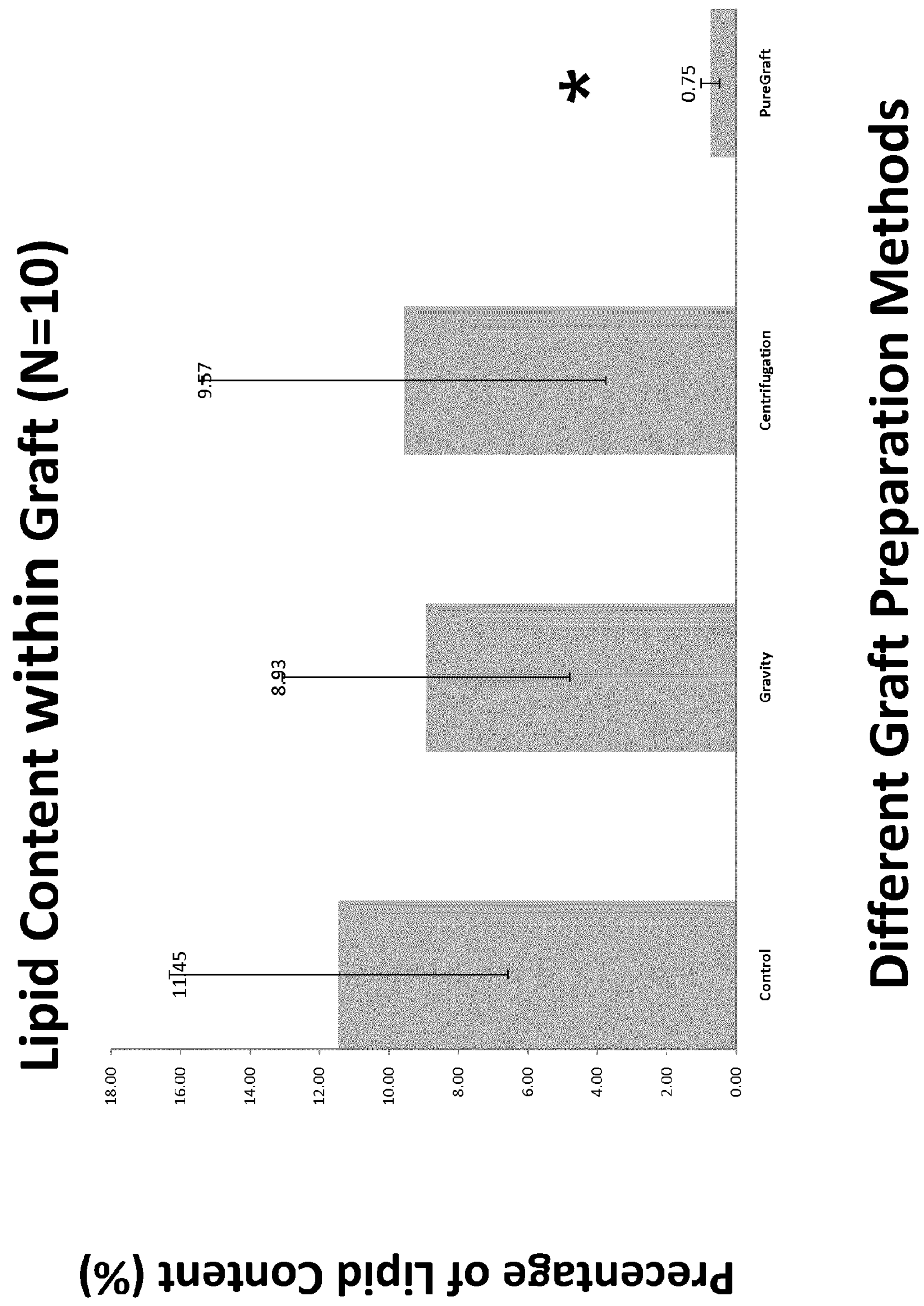
FIG. 16 is a bar graph showing the percent lipid content (v/v) of unprocessed adipose tissue (control), adipose tissue prepared by a gravity preparation method (Gravity), adipose tissue prepared by a centrifugation method (Centrifugation) and dried adipose tissue prepared according to the methods and systems described herein (PureGraft).

The graft tissues from each of the four groups were subsequently centrifuged at 400 g for five minutes in 15 ml conical tubes in triplicate in order to separate the grafts into four components; free lipid, adipose tissue, liquid, and a cell pellet comprising red and white blood cells. The volumes of lipid layer and liquid layer were recorded and calculated as percentage of total graft tissue. The volume of the lipid layer and the liquid layer of each sample was measured, and used to calculate the liquid content and lipid content of the different preparations. As shown in FIG. 15, adipose tissue prepared using the methods and systems described herein (PureGraft) had a significantly lower water content, when compared to unprocessed adipose tissue (Control), or adipose tissue processed by a conventional a gravity method (Gravity). Specifically, the mean liquid content of tissue prepared using the system of the current invention was 9.3±0.9%. This was significantly lower ($p<0.001$) than tissue prepared by gravity separation (25.1±1.8%). As shown in FIG. 16, adipose tissue prepared using the methods and systems described herein (PureGraft) had a significantly lower % content (v/v) of lipid compared to unprocessed adipose tissue (Control), adipose tissue prepared by a conventional gravity method (Gravity) and adipose tissue prepared by a conventional centrifugation method (Centrifugation). Specifically, the residual free lipid level in the samples prepared using the system of the current invention averaged 0.8±0.3% free lipid compared to control (unmanipulated) tissue (11.5±1.5%, $p<0.001$), gravity separation (8.9±1.3%, $p<0.001$), and centrifugation (9.6±1.8%, $p<0.001$). Note that the free lipid content observed in grafts prepared by centrifugation (average 9.6% of graft volume) was measured after removal of the free lipid observed during initial preparation of the graft. That is, the free lipid evident after separation of the graft into its component parts is newly released. This indicates that the graft material prepared by centrifugation contained damaged adipocytes that released their lipid during the second centrifugation applied to separate the graft into its four component parts. The fact that application of the same second centrifugation step to grafts prepared within system of the present invention revealed markedly less free lipid 0.8% of volume compared to 9.6%) demonstrates that grafts prepared within the system of the present invention contained fewer damaged adipocytes.

Figure 17:
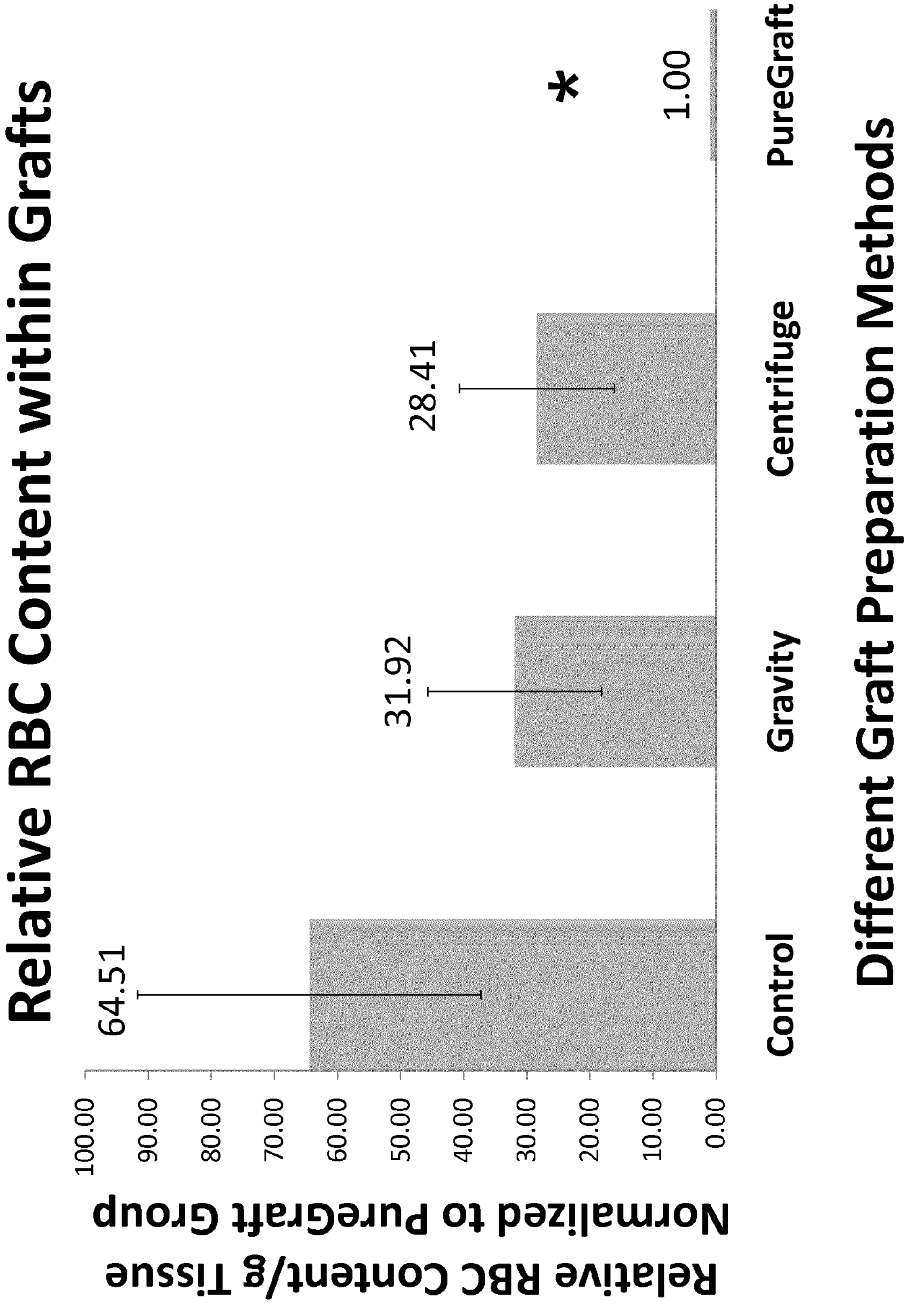
FIG. 17 is a bar graph showing the content of red blood cells (RBC) per gram of tissue normalized to the red blood cell content present per gram of tissue within grafts prepared according to the methods and systems described herein (PureGraft). Data are shown for unprocessed adipose tissue (control), adipose tissue prepared by a gravity preparation method (Gravity), and adipose tissue prepared by a centrifugation method (Centrifugation), and adipose tissue prepared according to the methods and systems described herein (PureGraft).

To assess the purity of the graft, samples from each tissue graft were removed from the tubes and analyzed for blood content by counting red blood cells and white blood cells per gram of tissue with a Coulter Counter. The data were normalized to control groups, and expressed as relative percentage of either RBC or WBC content per gram of unprocessed graft tissue. All data were expressed as average±SEM. A student t test was used to compare the differences between each graft preparation method. The data shown in FIG. 17 illustrate that adipose tissue prepared using the methods and systems disclosed herein (PureGraft) have significantly less red blood cells (RBCs) per gram of tissue, compared to unprocessed adipose tissue (Control), adipose tissue prepared by a conventional gravity preparation method (Gravity) and adipose tissue prepared by a conventional centrifugation method (Centrifugation). Thus, while gravity separation and centrifugation removed 47.8±7.0% and 53.2±5.4% of red blood cells respectively, preparation using the system of the present invention removed 98.1±0.01% red blood cells from the graft. Similarly, white blood cell content was reduced by 58.7±13.7% by gravity, 69.7±5.2% by centrifugation, and 96.80±0.01% using the system of the present invention.

The presence of water, lipid/mature adipocytes and blood cells can lead to loss of graft volume over time. The data shown in FIGS. 15-17 demonstrate that the systems described herein are useful for the preparation of dried or dehydrated adipose tissue grafts or implants.

The following example describes the production of an adipose tissue implant or graft supplemented with adipose-derived regenerative cells by the methods described herein.

Example 2

A patient in need of or desiring a breast implant is identified or selected. A unit of adipose tissue is removed from the patient and provided to an adipose-derived stem cell processing unit, which preferably, maintains a closed, sterile fluid/tissue pathway. For example, a cannula is connected to a tissue collection container or chamber (e.g., a flexible bag) of the adipose-derived stem cell processing unit while maintaining a sterile fluid/tissue pathway. Liposuction is performed by established techniques to remove adipose tissue from the subject and the removed unprocessed adipose tissue is drawn into the tissue collection container/chamber. A first portion of the adipose tissue is rinsed with PBS until substantially all of the saline, red blood cells, mature adipocytes are removed (e.g., successive washes until the tissue is no longer visibly red), and the wash effluent—the waste, e.g., saline, red blood cells, mature adipocytes, is aseptically removed through a port that is joined to the tissue collection container or chamber, while maintaining a closed, sterile fluid/tissue pathway. In some embodiments the waste port is connected to a waste collection container by a conduit and the waste collection container may be configured to attach to a vacuum source and the conduit and/or waste collection container may contain one or more valves. The first portion of washed adipose tissue can then be stored in the tissue collection container/chamber or transferred to a storage container or chamber for further processing.

A second portion of the unit of adipose tissue is rinsed with PBS until the tissue is no longer visibly red, as described above, in a second chamber. Alternatively, the adipose tissue obtained by liposuction is rinsed and washed, as described above, and afterward is split into a first and second portion. The first portion is retained for use as the substrate for the addition of adipose-derived regenerative cells and the second portion is used to create a suspension of adipose-derived regenerative cells as follows. An enzyme solution comprising collagenase is aseptically added to the second portion of tissue while maintaining a closed sterile fluid/tissue pathway. The tissue is incubated, while rocking, at 37° C. for approximately 1 hour. The mixture is allowed to settle, such that the lipo-digestate/adipose derived regenerative cell solution is physically separated from the undigested adipose tissue and lipid. The lipo-digestate created from the second portion of adipose tissue is removed through a conduit while maintaining a closed, sterile fluid/tissue pathway.

The separated lipo-digestate is then pumped through a conduit that is connected with the first chamber though a closed pathway. The lipo-digestate is pumped over and through the first portion of unprocessed adipose tissue in the first chamber. The non-cellular component of the lipo-digestate flows through the first portion of unprocessed adipose tissue into a waste container, while maintaining a closed sterile fluid/tissue pathway. The lipo-digestate can be filtered through the first portion of unprocessed adipose tissue using gravity or a vacuum source. In some embodiments, the lipo-digestate can be layered on top of the first portion of unprocessed adipose tissue and the adipose-derived regenerative cells present in the lipo-digestate can be forced into the matrix of the first portion of unprocessed adipose tissue using centrifugation (e.g., spinning bucket centrifugation at 100, 200, 300, 400, 500, 600, 700, or 800 g). The adipose-derived regenerative cells of the lipo-digestate are bound by the connective tissue fragments, producing a fat graft supplemented with adipose-derived regenerative cells. The supplemented or fortified fat graft can then be provided to the subject with or without an absorbable casing or capsular material that has a shape of a human breast.

Example 3

A fat graft supplemented with adipose-derived regenerative cells is prepared as described in Example 1. The fat graft supplemented with adipose-derived regenerative cells is administered to the face, buttocks, chest, or calves of a subject or to correct any soft tissue defect.

Example 4

A patient in need of or desiring a fat graft is identified or selected. A unit of adipose tissue is removed from the patient as described herein or as known in the art. To optimize the graft, the system 300 is oriented and a waste bag (not shown) connected to the system is dropped to the floor. Adipose tissue is introduced into the system 300 through tissue access port 600 which provides communication between the external environment and the interior of the first subsystem. A Toomey or other art recognized syringe may be used to inject the lipoaspirate through the port. This may be repeated until the desired amount of tissue has been added—taking care not to exceed the maximum volume of the first subsystem. Once the lipoaspirate has been added, the pinch clamp on the drain tubing (not shown) is closed. A washing and/or rinsing solution, such as Lactated Ringers or saline, is introduced into the system 300 by opening the wheel clamp (not shown) through a port or by way of sterile IV tubing. The amount of washing or rinsing solution to be added may vary. Generally, sufficient washing solution is introduced into the system such that the majority of the lipoaspirate or other tissue in the first subsystem is submerged. 150 mls of washing solution such as Lactated Ringers is added. Next, the wheel clamp is closed and the system is manually agitated for a brief period of time, e.g., 15 seconds. The agitation may be in the form of inversion, rotation, rocking, etc. The system is agitated by external means such as on a shaking platform, an orbital shaker etc. After the tissue is thoroughly washed (as determined by observation or a pre-established time interval), a drain pinch valve (not shown) or a port is opened and, under gravitational forces, the effluent passes through the filter material 320 and the separation screen 330. The effluent is allowed to drain for a period of time, e.g., 3 minutes. This cycle can be repeated a number of times. The cycle may be repeated for a total of four washes. After the last wash cycle, the waste should be allowed to drain for five to ten minutes. Generally, maximal draining of waste fluids occurs after about 10 minutes of draining. Accordingly, a dryer washed fat graft is created that is substantially free of blood, tumescent fluid and free lipid without the need for mechanical equipment and in a closed sterile system which is easy to operate. Also, this process can be completed in as little as 20 minutes and the surgeon can control the level of hydration desired by altering the length of time that the system is allowed to drain during the final step.

If enriching the fat graft obtained by using the system 300 with adipose derived regenerative cells (ADRCs) is desired, the ADRCs obtained by any method described herein or known in the art (such as by use of the CELUTION® System), may be added via a port near the bag of Lactated Ringers and chased with Lactated Ringers or other suitable solution for 5 seconds or more. The system can then be agitated as described herein, e.g., for 15 seconds, and the ADRC enhanced fat graft may then be injected or placed back into the patient as needed.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An adipose tissue processing device, comprising: a flexible, collapsible bag comprising a first outer shell and a second outer shell that are joined to form a bag, wherein the bag comprises:

a first port in communication with a first subsystem, which receives adipose tissue and, which is defined by a first outer shell of the bag and a filter disposed within the bag, wherein the filter comprises a plurality of pores that pass liquids, tumescent fluids, red blood cells, and wash solutions and retain mature adipocytes, regenerative cells, stem cells, progenitor cells and connective tissue; and a second port in communication with a second subsystem, which is defined by the filter and the second outer shell of the bag, wherein the second subsystem further comprises a separator that creates a space between the filter and the second outer shell of the bag, wherein said separator comprises a separation screen or mesh that comprises pores that are larger than the pores in the filter, wherein the first subsystem and second subsystem are configured to store tissue or cell samples within the bag as the flexible, collapsible bag expands, wherein the pore size of said filter is between about 30 μm and about 200 μm, and wherein the separator comprises pores that comprise a pore size that is between about 300 and 2000 μm.

2. The adipose tissue processing device of claim 1, wherein the separator has a degree of freedom.

3. The adipose tissue processing device of claim 1, wherein the separator is free floating within said second subsystem.

4. The adipose tissue processing device of claim 1, wherein the separator comprises on or more ribs.

5. The adipose tissue processing device of claim 1, wherein the separator comprises on or more struts.

6. The adipose tissue processing device of claim 1, wherein the first outer shell and the second outer shell are joined by a double heat seal.

7. The adipose tissue processing device of claim 6, wherein the filter is joined to the first outer shell and the second outer shell by a double heat seal.

8. The adipose tissue processing device of claim 1, wherein said separator comprises a mesh.

9. The adipose tissue processing device of claim 1, wherein said separator comprises a screen.

10. The adipose tissue processing device of claim 1, wherein said first port is configured to releasably connect with an adapter, said adapter being configured to releasably connect with a syringe barrel.

11. The adipose tissue processing device of claim 10, wherein the first port is configured to allow material to enter into the first port, but not to exit from the first port.

12. The adipose tissue processing device of claim 11, wherein said first port comprises a deformable plastic valve.

13. The adipose tissue processing device of claim 10, wherein the syringe barrel is a 60 mL catheter syringe barrel.

14. The adipose tissue processing device of claim 1, wherein the first port is configured to be attached to a cannula, while maintaining a sterile fluid/tissue pathway.

15. The adipose tissue processing device of claim 1, further comprising a third port in communication with the first subsystem, which exists between the first outer shell of the bag and the filter disposed within the bag.

16. The adipose tissue processing device of claim 15, wherein said third port is connected to a Y connector.

17. A method of making an adipose tissue graft, comprising:

(a) obtaining a first portion of unprocessed adipose tissue;

(b) introducing said first portion of unprocessed adipose tissue into the first subsystem of a first device of claim 1, (c) rinsing the first portion of unprocessed adipose tissue by adding a physiologic wash solution to the first subsystem; and (d) removing fluid from the second subsystem of the first device, wherein the fluid is selected from the group consisting of water, physiologic wash solution, blood and free lipid, or any combination thereof, thereby dehydrating the adipose tissue.

18. The method of claim 17, wherein the physiologic wash solution is selected from the group consisting of Lactated Ringer's solution, Hartmann's Solution, and saline.

19. The method of claim 17, wherein said dehydrated adipose tissue has a liquid content that is less than about ½, ⅓, or ¼ times that of said first portion of unprocessed adipose tissue prior to the introducing step.

20. The method of claim 17, wherein said dehydrated adipose tissue has a liquid content that is less than about ⅓ that of said first portion of unprocessed adipose tissue prior to the introducing step.

* * * * *